United States Patent [19]
Holt et al.

[11] Patent Number: 6,133,456
[45] Date of Patent: Oct. 17, 2000

[54] SYNTHETIC MULTIMERIZING AGENTS

[75] Inventors: Dennis A. Holt, Stow; Terence P. Keenan, Cambridge, both of Mass.; Tao Guo, Somerset, N.J.; Edgardo Laborde, Foster City, Calif.; Wu Yang, Chestnut Hill, Mass.

[73] Assignee: ARIAD Gene Therapeutics, Inc., Cambridge, Mass.

[21] Appl. No.: 08/808,276

[22] Filed: Feb. 28, 1997

Related U.S. Application Data

[63] Continuation-in-part of application No. 08/793,016, Aug. 18, 1995, abandoned, and application No. 08/479,694, Jun. 7, 1995, which is a continuation-in-part of application No. 08/292,598, Aug. 18, 1994, abandoned.

[60] Provisional application No. 60/033,035, Dec. 10, 1996, provisional application No. 60/024,861, Aug. 28, 1996, and provisional application No. 60/012,432, Feb. 28, 1996.

[51] Int. Cl.$^7$ ............. C07D 207/04; C07D 211/06; C07D 401/02; C07D 403/02

[52] U.S. Cl. .................... 548/533; 504/454; 544/82; 544/107; 544/129; 544/130; 544/175; 544/365; 544/372; 546/187; 546/189; 546/194; 546/197; 546/201; 546/208; 546/226; 546/245; 548/518; 548/537

[58] Field of Search ................. 546/187, 189, 546/194, 197, 201, 226, 245, 208; 544/107, 130, 175, 365, 372, 82, 129; 540/454; 548/533, 537, 518

[56] References Cited

U.S. PATENT DOCUMENTS

| | | | |
|---|---|---|---|
| 5,120,727 | 6/1992 | Kao et al. ................... | 514/183 |
| 5,162,333 | 11/1992 | Failli et al. ................. | 514/291 |
| 5,192,773 | 3/1993 | Armistead et al. .......... | 514/315 |
| 5,620,971 | 4/1997 | Armistead et al. .......... | 514/212 |
| 5,622,970 | 4/1997 | Armistead et al. .......... | 514/315 |
| 5,717,092 | 2/1998 | Armistead et al. .......... | 544/129 |
| 5,744,485 | 4/1998 | Zelle et al. .................. | 514/318 |
| 5,780,484 | 7/1998 | Zelle et al. .................. | 514/316 |
| 5,811,434 | 9/1998 | Zelle et al. .................. | 514/307 |
| 5,830,462 | 11/1998 | Crabtree et al. ............. | 424/93.21 |
| 5,834,266 | 11/1998 | Crabtree et al. ............. | 435/172.3 |
| 5,871,753 | 2/1999 | Crabtree et al. ............. | 424/280.1 |
| 5,994,313 | 11/1999 | Crabtree et al. ............. | 514/31 |

OTHER PUBLICATIONS

Spencer, D.M. et al., "Controlling Signal Transduction with Synthetic Ligands", Science, 262:1019–1024, Nov. 21, 1993.

Uchiyama, T. et al., "Synthesis of Hybrid Type of Anti–HIV Drugs", Peptide Chemistry 1993; 31(1):89–92, 1994.

CAS Online Printout for Mauger et al, Separation of Actinomycins and Biosynthetic Analogs by Normal and Reversed Phase High Performance Liquid Chromatography, Journal of Antibiotics, vol. 43, No. 2, pp. 220–221, 1990.

Babine and Bender, "Molecular Recongnition of Protein–Ligand Complexes: Applications to Drug Design", Chem. Rev. 97, 1359–1472, see esp. pp. 1437–1449, 1997.

Yamashita et al., "Design, Synthesis and Evaluation of Dual Domain FKBP Ligands", Bioorganic & Medicinal Chem Letters, vol. 4, No. 2, pp. 325–328, 1994.

Luengo et al., "Synthesis and Structure Activity Relationships of Macrocyclic FKBP Ligands", Bioorganic & Medicinal Chem Letters, vol. 4, No. 2, pp. 321–324, 1994.

Holt et al., "Structure Activity Studies of Synthetic FKBP Ligands as Peptidyl–prolyl Isomerase Inhibitors", Bioorganic & Medicinal Chem Letters, vol. 4, No.2, pp. 315–320, 1994.

Holt et al., "Design, Synthesis and Kinetic Evaluation of High–Affinity FKBP Ligands and The X–ray Crystal Structures of Their Complexes with FKBP12", J American Chem Society, vol. 115, pp. 9925–9938, 1993.

*Primary Examiner*—Mukund J. Shah
*Assistant Examiner*—Brenda Coleman
*Attorney, Agent, or Firm*—David L. Berstein; Sharon F. Hausdorff

[57] ABSTRACT

New compounds are disclosed for multimerizing immunophilins and proteins containing immunophilin or immunophilin-related domains. The compounds are of the formula $$M^1—L—M^2$$

where $M^1$ and $M^2$ are independently moieties of the formula:

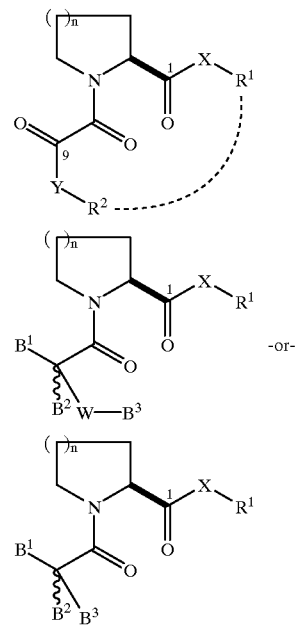

in which $B^1$, $B^2$, $B^3$, $R^1$, $R^2$, n, W, X and Y are as defined.

8 Claims, No Drawings

SYNTHETIC MULTIMERIZING AGENTS

This application is a continuation-in-part of each of the following applications, the full contents of which are expressly incorporated herein by reference: U.S. Ser. No. 60/033,035 filed Dec. 10, 1996; U.S. Ser. No. 60/024,861 filed Aug. 28, 1996; U.S. Ser. No. 60/012,432 filed Feb. 28, 1996; U.S. Ser. No. 08/793,016 filed Aug. 18, 1995 (now abandoned); and U.S. Ser. No. 08/479,694 filed Jun. 7, 1995 which was a CIP of U.S. Ser. No. 08/292,598 filed Aug. 18, 1994 (now abandoned).

BACKGROUND OF THE INVENTION

Aspects of the design, production and use of biological switches based on ligand-mediated multimerization of immunophilin-based recombinant proteins are disclosed in Spencer et al, Nov. 12, 1993, Science 262:1019–1024 and in International Patent Applications PCT/US94/01660 and PCT/US94/08008. One class of multimerizing agents is based on dimers of the macrocyclic natural product, FK506, covalently attached to each other via a synthetic linker moiety. The resultant dimers ("FK1012" molecules) are characterized by high binding affinities for immunophilin molecules. However, they are large, complex molecules which can be inconvenient to produce. New methods and materials for multimerizing chimeric proteins containing immunophilin moieties would be desirable, where the methods and materials involve smaller, simpler multimerizing agents which retain a high binding affinity for their coordinate immunophilins, but which are more convenient to produce and are more readily amenable to structural modification.

DESCRIPTION OF THE INVENTION

This invention provides a new method and materials for multimerizing immunophilins (including naturally occurring immunophilin proteins as well as chimeric proteins containing immunophilin-derived domains) based on N-oxalyl-pipecolyl and N-oxalyl-prolyl ligand moieties. ("Multimerization" as the term is used herein encompasses dimerization and higher order multimerization.)

The invention relates to immunophilin multimerizing agents of formula I, $$M^1\text{—}L\text{—}M^2 \qquad (I)$$

and pharmaceutically acceptable salts thereof, including their individual stereoisomers and mixtures of stereoisomers, where $M^1$ and $M^2$ are independently moieties of formula II:

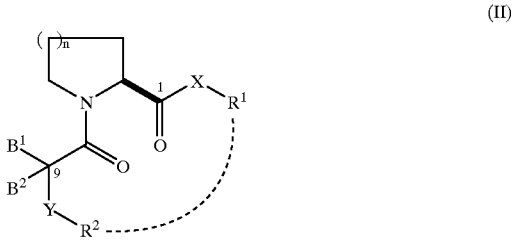

(II)

where
n=1 or 2;
X=O, NH or $CH_2$;
$B^1$ and $B^2$ are independently H, C1–C10 aliphatic, heteroaliphatic, aryl or heteroaryl as those terms are used elsewhere, or $B^1$ and $B^2$ taken together represent a carbonyl group, =O;
Y=O, NH, $NR^3$, or represents a direct, i.e. covalent, bond from $R^2$ to atom 9;
$R^1$, $R^2$, and $R^3$ are independently $C_1$–$C_{20}$ aliphatic, heteroaliphatic, aryl or heteroaryl;
wherein aliphatic and heteroaliphatic moieties include both saturated and unsaturated straight chain, branched, cyclic, or polycyclic aliphatic hydrocarbons which may contain oxygen, sulfur, or nitrogen in place of one or more carbon atoms, and which are optionally substituted with one or more functional groups selected from the group consisting of hydroxy, $C_1$–$C_8$ alkoxy, acyloxy, carbamoyl, amino, N-acylamino, ketone, halogen, cyano, carboxyl, and aryl (unless otherwise specified, the alkyl, alkoxy and acyl groups preferably contain 1–6 contiguous aliphatic carbon atoms);
aryl and heteroaryl moieties include stable cyclic, heterocyclic, polycyclic, and polyheterocyclic unsaturated $C_3$–$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$–$C_8$ alkoxy, $C_1$–$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry);
$R^1$ and $R^2$ may optionally be joined, i.e., covalently linked, together, forming a macrocyclic structure (as indicated by the dashed line in II), although compounds in which $R^1$ and $R^2$ are not covalently joined to form a macrocycle are currently of particular interest,; and
L is a linker moiety covalently linking monomers $M^1$ and $M^2$ through covalent bonds to either $R^1$ or $R^2$, not necessarily the same in each of $M^1$ and $M^2$.

Linker moieties (L), need not contain essential elements for binding to the immunophilin proteins, and may be selected from a very broad range of structural types. Linker moieties of particular interest include $C_2$–$C_{20}$ aliphatic, heteroaliphatic, aryl or heteroaryl structures as defined above. The linker moiety may be an ether, polyether, amine or polyamine, and/or may contain a variety of substituents. Linker moieties may be conveniently joined to monomers $M^1$ and $M^2$ through functional groups such as ethers, amides, ureas, carbamates, and esters; or through alkyl-alkyl, alkyl-aryl, or aryl-aryl carbon-carbon bonds.

Furthermore, linker moieties may be optimized (e.g., by modification of chain length and/or substituents) to enhance pharmacokinetic properties of the formula I multimerizing agent. Numerous linker moieties and classes of linker moieties of general applicability are exemplified in the various illustrative compounds disclosed herein.

Preferred compounds are compounds other than those disclosed in PCT/US95/10559 and/or which possess different functional properties from the compounds disclosed therein.

In one subset of compounds of this invention one or both of the monomers contain a —YR$^2$ substituent in which Y is either O or a covalent C—C bond, and R$^2$ comprises a branched, unbranched or cyclic aliphatic moiety, preferably of 1 to about 12 carbon atoms (including for example methyl, ethyl, n-propyl, isopropyl, cyclopropyl, allyl, n-butyl, sec-butyl, isobutyl, tert-butyl, cyclobutyl, n-pentyl, sec-pentyl, isopentyl, tert-pentyl, cyclopentyl, n-hexyl, sec-hexyl, cyclohexyl, —CH$_2$-cyclohexyl and the like), which aliphatic moiety may contain one or more unsaturated covalent bonds and may optionally be substituted with an —OH, NH$_2$ (or substituted amine or carbamate), ether (or thio-ether, in either case, aliphatic or aromatic), aryl, or heteroaryl moiety, and may optionally contain a heteroatom in place of one or more CH$_2$ or CH units; or R$^2$ comprises a substituted or unsubstituted aryl or heteroaromatic moiety. Illustrative R$^2$ moieties include those of the following sort:

| C1–C6 branched or unbranched alkyl, e.g. | C1–C8 branched or unbranched alcohols, e.g., —CH$_2$—OH, —CH$_2$CH$_2$— OH, or |
|---|---|
| 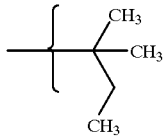 | 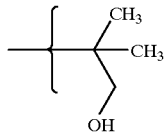 |

C1–C6 branched or unbranched alkoxyl, C3–C7 cycloalkyl phenyl and mono-, di- and tri-alkoxyphenyl

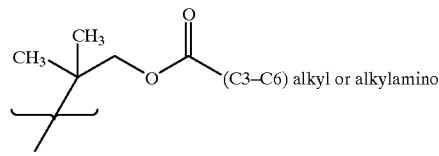

-continued

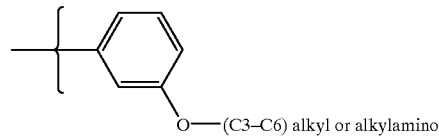

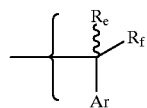

| Re | Rf |
|---|---|
| CH$_3$CH$_2$—O— | H |
| CH$_3$CH$_2$— | H |
| HO—CH$_2$— | H |
| CH$_3$— | H |
| cyclohexyl | cyclohexyl |

In such compounds, B$^1$ and B$^2$ are as defined above, and may for example, be independently selected from H or any of the candidate moieties for R$^2$, including without limitation, alkyl, cycloalkyl, phenyl or substituted phenyl moieties, including e.g. mono-, di- and tri-alkoxyphenyl substituents such as 3,4,5-trimethoxyphenyl. In some embodiments, B$^1$ and B$^2$, taken together, are a carbonyl moiety.

The following table illustrates a variety of monomers which we have prepared. Those compounds tested were found to bind to native and engineered variants of hFKBP12 with varying affinities. Dimers produced by covalently linking two such monomer moieties together using linker moieties as disclosed herein are capable of dimerizing fusion proteins containing native or engineered.FKBP domains over a range of EC50 values. For the purpose of the table, (subscripted) R$_1$ through R$_6$ represent moieties of the formula:

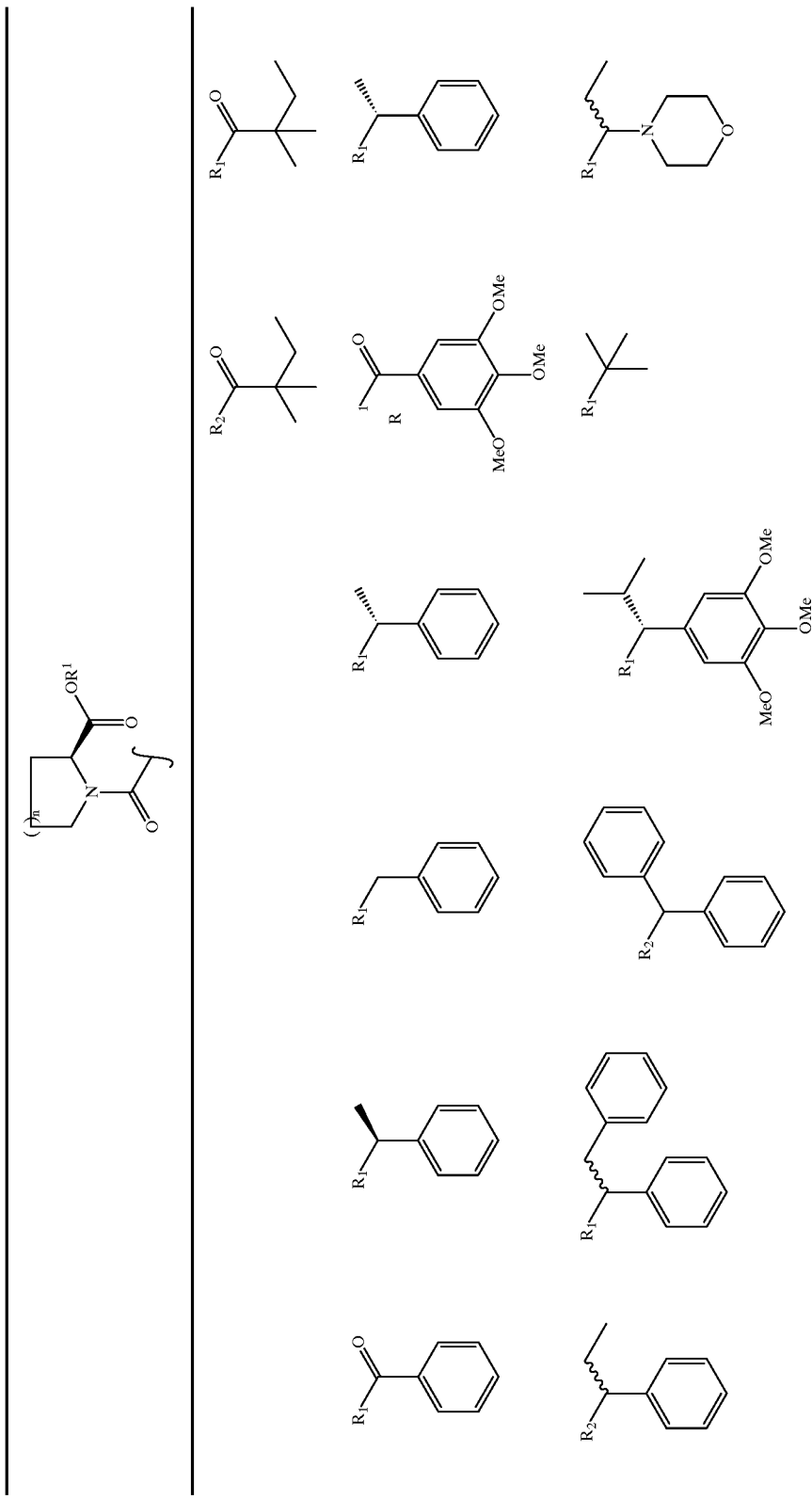

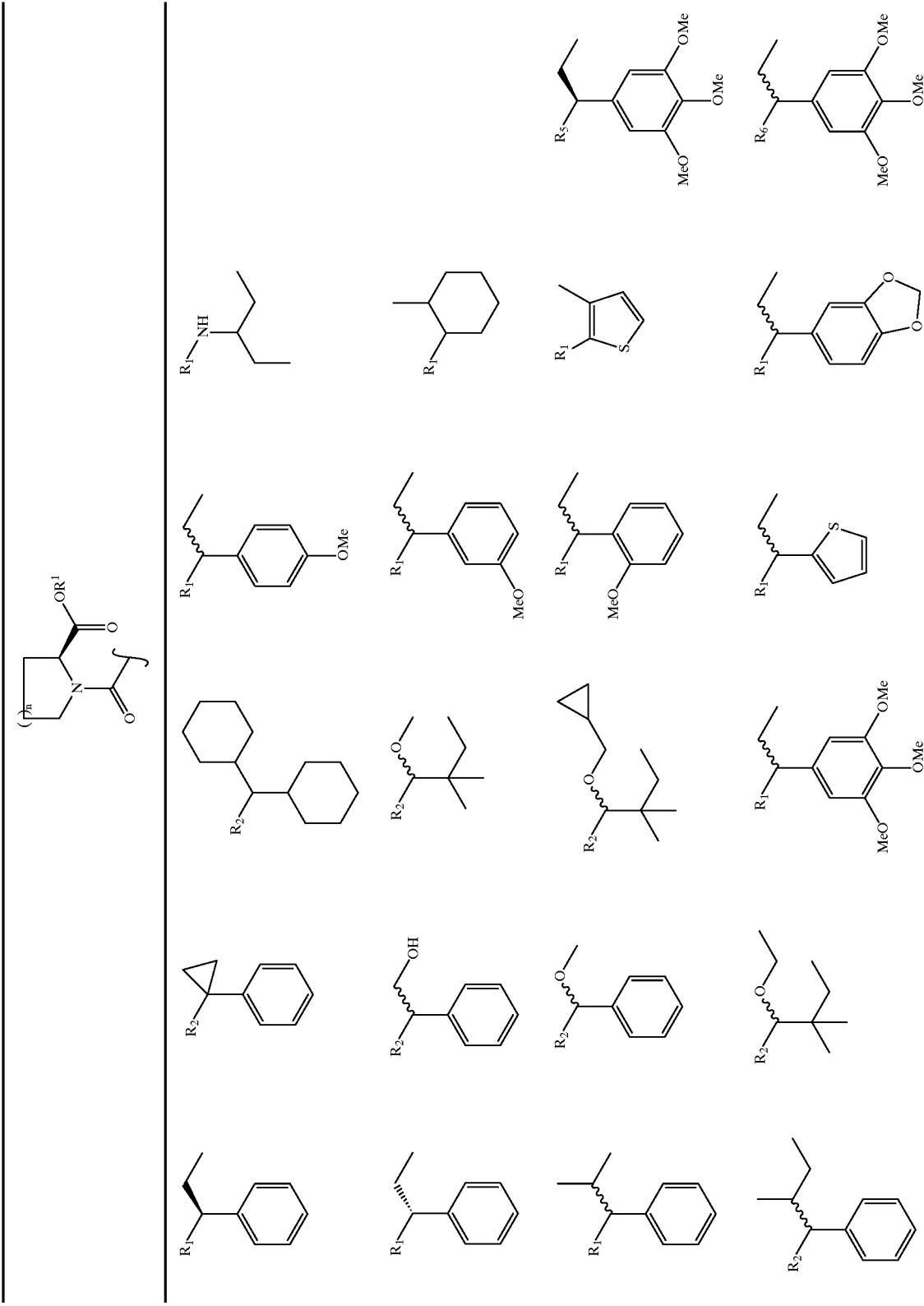

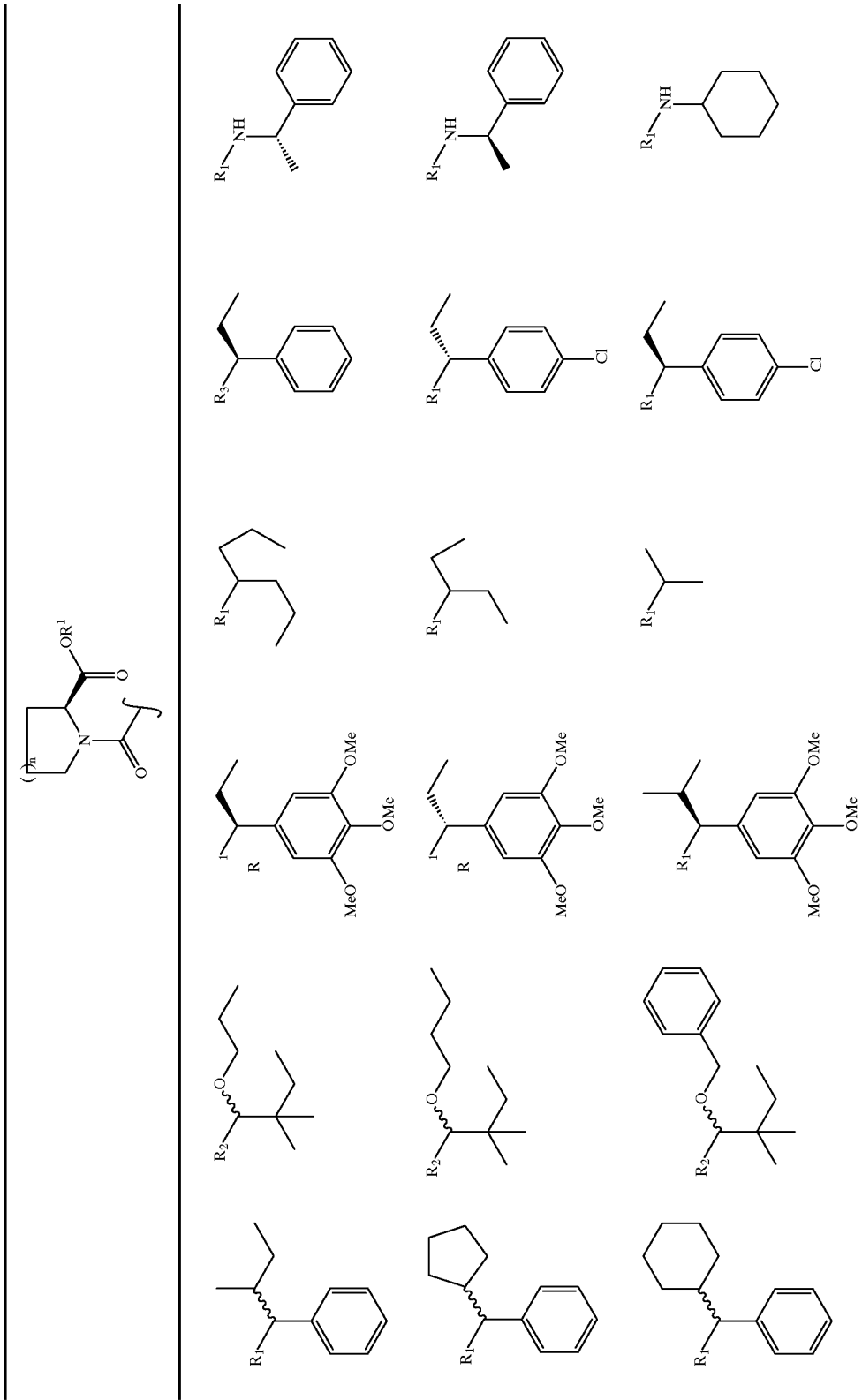

Examples of $R_1$ through $R_6$ include among others the following sorts of structures:

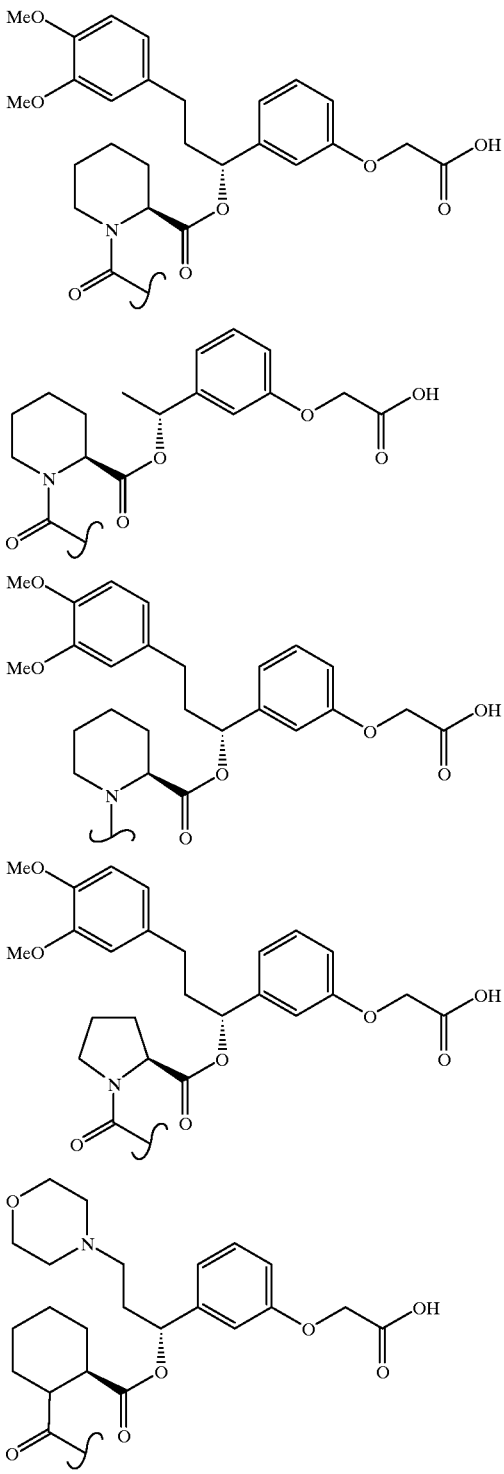

Other moieties suitable for linking to the —($B^1$)($B^2$)($YR^2$) moiety are disclosed elsewhere herein. Note that the —$CH_2CO_2H$ or —$OCH_2CO_2H$ moiety may alternatively be written as part of the linker moiety, as in the next table below.

In certain compounds of this invention, —$XR^1$ is a moiety of the formula

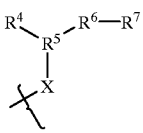

where $R^4$ is a H, aliphatic, heteroaliphatic, aryl or heteroaryl, e.g. phenyl, substituted phenyl, indolyl, pyridyl, etc.; $R^5$ is a branched, unbranched or cyclic aliphatic moiety of 1 to 8 carbon atoms, which may be optionally substituted, including —$CH_2$, —$CH_2CH_2$—, —$CH_2CH_2CH_2$—, —CH(CH3)$CH_2$—, and the like; $R^6$ is an aromatic, saturated or unsaturated heterocyclic or heteroaromatic moiety bearing a reactive functional group, $R^7$, permitting covalent attachment to a linker moiety. $R^7$ may be —CH=$CH_2$, —COOH, —CHO, —X"H or X"$R^8$, where X" is O, S or NH (which may bear an optional substituent such as an alkyl group of 1–8 carbon atoms) and $R^8$ is —$(CH_2)_z$—COOH where z is an integer from 1 through 4. Illustrative —XR1 moieties include the following:

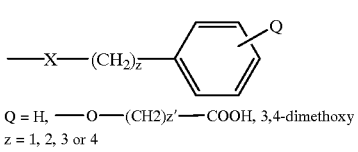

Q = H, —O—(CH2)z'—COOH, 3,4-dimethoxy
z = 1, 2, 3 or 4

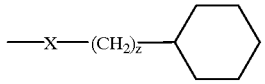

$R^9$ = H, alkyl, or —$CO_2$alkyl
z = 1, 2, 3 or 4

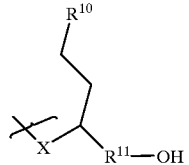

$R^{10}$ is a substituted or unsubstituted alicyclic, heterocyclic, heteroaromatic or aromatic moiety $R^{11}$ is a substituted or unsubstituted aryl or heteroaryl moiety Examples of —$XR^1$ moieties of the formula $R^{10}$—$CH_2CH_2$—CH—$R^{11}$—OH include:

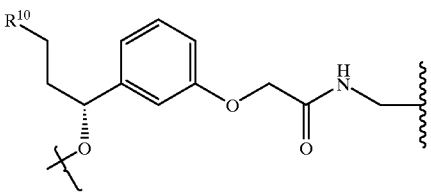

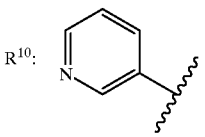

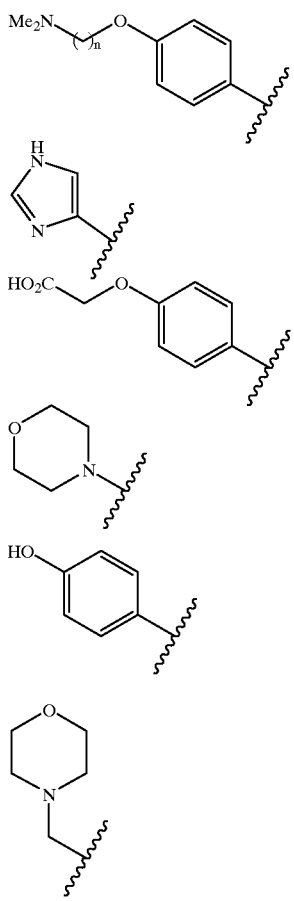
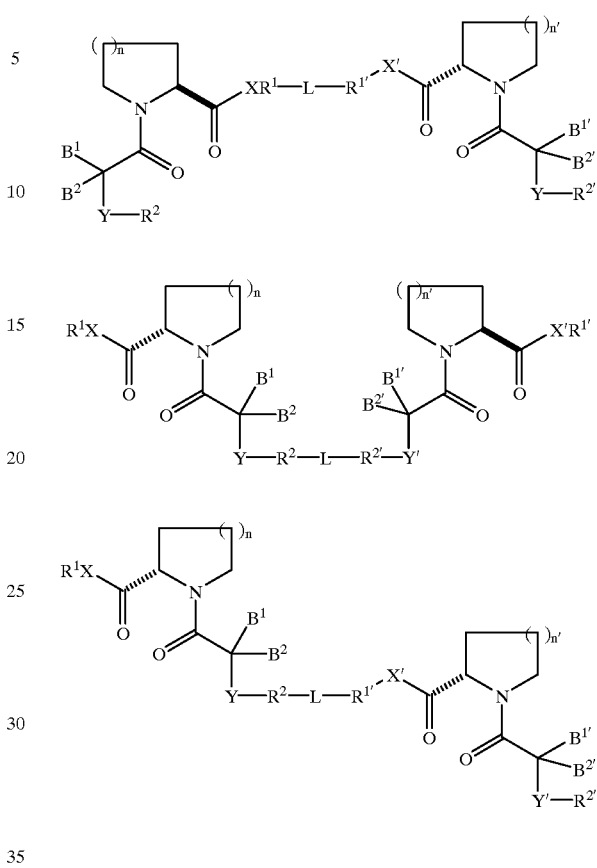
The following formulae provide three exemplary (and non-exclusive) classes of compounds of this invention:
Illustrating one series of compounds of the first such class, and various linker moieties (which may be used with other monomers of this invention), are compounds of the formula:
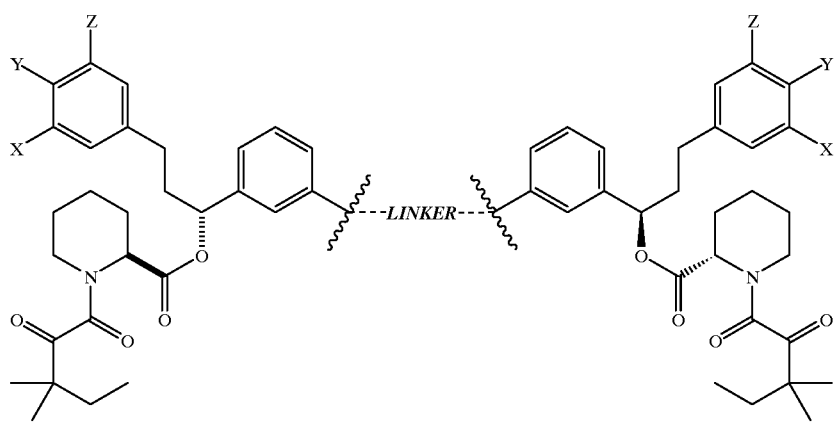

as depicted in the following table:

| Monomer | | | |
|---|---|---|---|
| X | Y | Z | Linker |
| MeO | MeO | H | ![linker structure] |
| MeO | MeO | H | ![linker structure with N-Me groups] |
| N | H | H | ![linker structure] |
| N | H | H | ![linker structure with N-Me groups] |
| MeO | MeO | H | ![piperazine linker] |
| N | H | H | ![piperazine linker] |
| MeO | MeO | H | ![triethylene glycol linker] |
| MeO | MeO | H | ![tetraethylene glycol linker] |
| H | H | H | ![butylene diamine linker] |
| MeO | MeO | H | ![butylene diamine linker] |

-continued
| Monomer | | | |
|---|---|---|---|
| X | Y | Z | Linker |
| —OCH₂O— | | H | 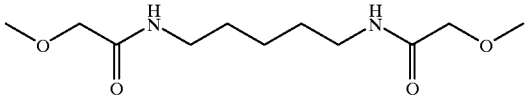 |
| MeO | MeO | MeO | 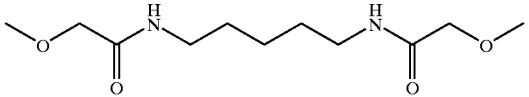 |
| N | H | H | 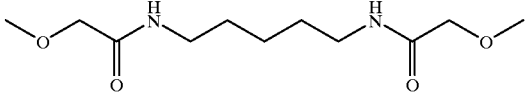 |
| H | H | H | 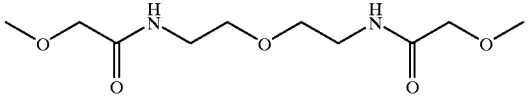 |
| MeO | MeO | H | 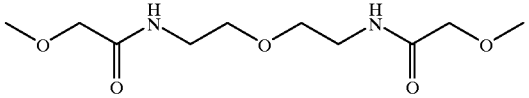 |
| —OCH₂O— | | H | 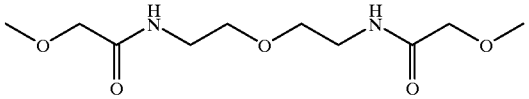 |
| MeO | MeO | MeO | 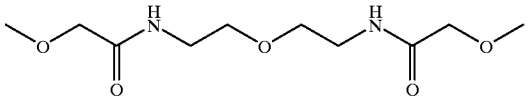 |
| N | H | H | 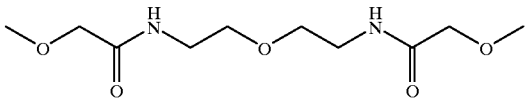 |
| H | H | H | 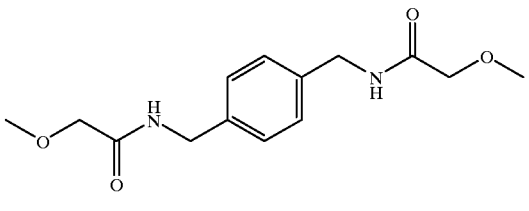 |
| H | H | H | 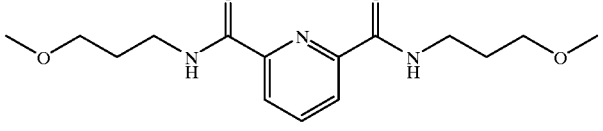 |
| H | H | H | 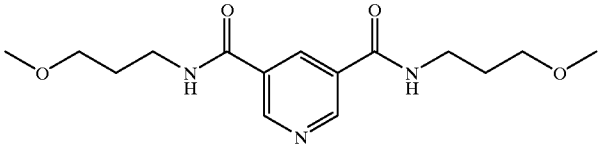 |

-continued

| Monomer | | | |
|---|---|---|---|
| X | Y | Z | Linker |
| H | H | H | (1-methylpyridinium-3,5-dicarboxamide with two N-(3-methoxypropyl) groups) |
| H | H | H | (5-aminobenzene-1,3-dicarboxamide with two N-(3-methoxypropyl) groups) |
| H | H | H | (benzene-1,3-disulfonamide with two N-(3-methoxypropyl) groups) |
| H | H | H | (bis[N-(3-(methoxyacetamido)propyl)]methylamine) |
| H | H | H | (1,4-phenylenebis(acetamide) with two N-(3-methoxypropyl) groups) |
| H | H | H | (1,4-bis[3-(methoxyacetamido)propyl]piperazine) |
| H | H | H | (2,6-diamino linker with two N-(3-methoxypropyl)amide termini) |
| H | H | H | (N,N'-bis(methoxyacetyl)-3,6-dioxa-1,8-octanediamine) |
| MeO | MeO | H | (N,N'-bis(methoxyacetyl)-3,6-dioxa-1,8-octanediamine) |

-continued
| Monomer | | | Linker |
|---|---|---|---|
| X | Y | Z | |
| —OCH$_2$O— | | H | 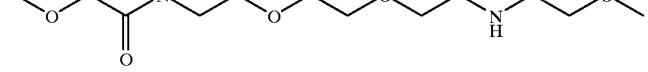 |
| MeO | MeO | MeO | 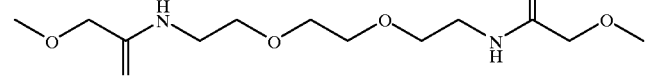 |
| N | H | H | 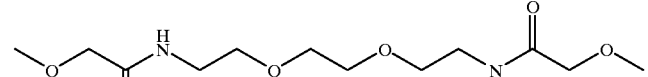 |
| H | H | H |  |
| H | H | H |  |
| MeO | MeO | H |  |
| —OCH$_2$O— | | H |  |
| MeO | MeO | MeO |  |
| N | H | H |  |
| H | H | H |  | noting that by X=N in the preceding formula we mean to designate a ring nitrogen in a pyridine ring:

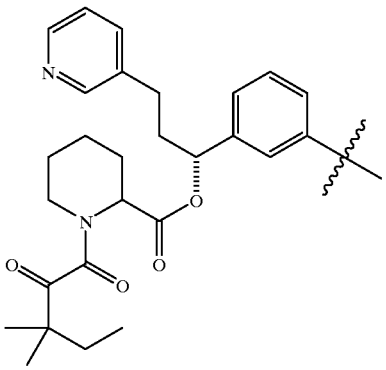

Other compounds of this invention include mixed multimerizing agents of the formula M—L—Q, in which M is a synthetic monomer such as described herein, covalently linked by linker, L, to Q, a natural product immunophilin ligand such as FK506, FK520, rapamycin, cyclosporin A, or an analog or derivative thereof. Numerous such ligands and analogs and derivatives thereof are known in the art which may be linked to synthetic monomers using materials and methods described e.g. in PCT/US94/01667.

The multimerizing agents of this invention preferably cannot participate in a ternary complex with both immunophilin and calcineurin, or with immunophilin and FRAP (Brown et al., Nature, 1994, 369, 756–758), and are therefore not immuno-suppressive like FK506 or rapamycin. Additionally, it will often be preferred that the multimerizing agent be physiologically acceptable (i.e., lack undue toxicity toward the cell or organism with which it is to be used), can be taken orally by animals (i.e., is orally active in applications in whole animals, including gene therapy), and/or can cross cellular and other membranes, as necessary for a particular application.

The multimerizing agents can be used as described in PCT/US94/01617 and PCT/US94/08008, e.g. to activate the transcription of a desired gene, actuate apoptosis, or trigger other biological events in engineered cells growing in culture or in whole organisms, including in gene therapy applications. The engineered cells contain and are capable of expressing DNAs encoding proteins containing one or more immunophilin domains, such as an FKBP domain or mutant FKBP domain, which are capable of binding to the monomers, M (formula II), or to multimerizing agents comprising such monomers such as depicted in formulas II and in the many examples disclosed herein. In such applications, the multimerizing agent is administered to the cell culture or to the organism containing the cells, as the case may be, in an amount effective to multimerize the proteins containing the corresponding ligand-binding domains (as may be observed by monitoring the transcription, apoptosis or other biological process so triggered). In the case of administration to whole organisms, the multimerizing agent may be administered in a composition containing the multimerizing agent and acceptable veterinary or pharmaceutical diluents and/or excipients. Monomers disclosed herein are also useful, both in the synthesis of dimerizing agents as disclosed in detail herein, and in their own right in view of their binding affinity for immunophilins or modified immunophilins. They may be administered to the engineered cells, or to organisms containing them (preferably in a composition as described above in the case of administration to whole animals), in an amount effective for reversing or blocking the effect of the multimerizing agent, i.e. for preventing, inhibiting or disrupting multimerization.

Compounds of this invention may be prepared by adaptation of known methods for the synthesis of N-oxalyl-pipecolyl, N-oxalyl-prolyl and related monomers. See e.g. Holt, et al., *J. Amer. Chem. Soc.*, 1993, 115, 9925–9938; Holt, et al., *Biomed. Chem. Lett.*, 1993, 4, 315–320; Luengo, et al., *Biomed. Chem. Lett.*, 1993, 4, 321–324; Yamashita, et al., *Biomed. Chem. Lett.*, 1993, 4, 325–328; Spencer et al, above; PCT/US94/01617; and PCT/US94/08008. See also EP 0 455 427 A1; EP 0 465 426 A1; U.S. Pat. No. 5,023,263 and WO 92/00278.

For example, monomers may be assembled and dimerized via a number of synthetic schemes and in various orders as illustrated in the following reaction schemes.

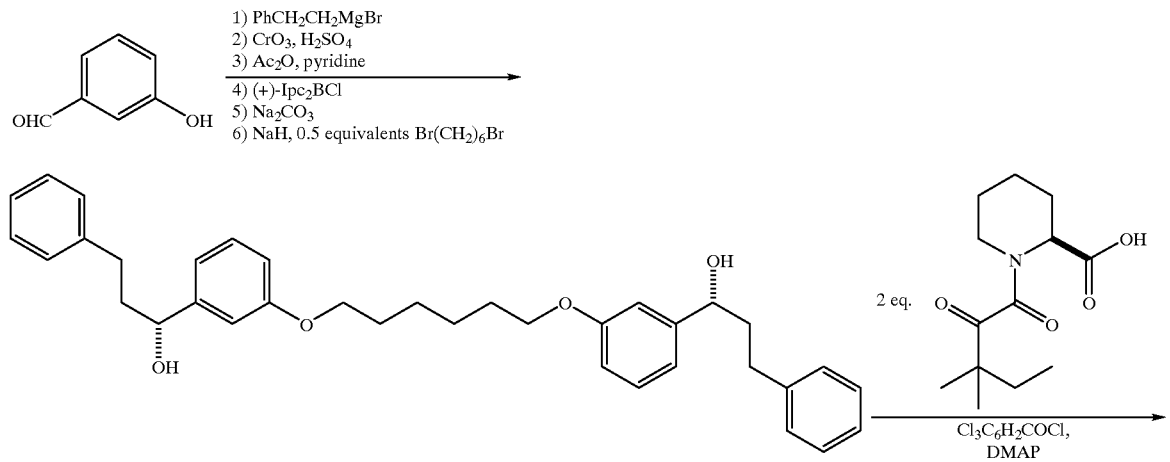

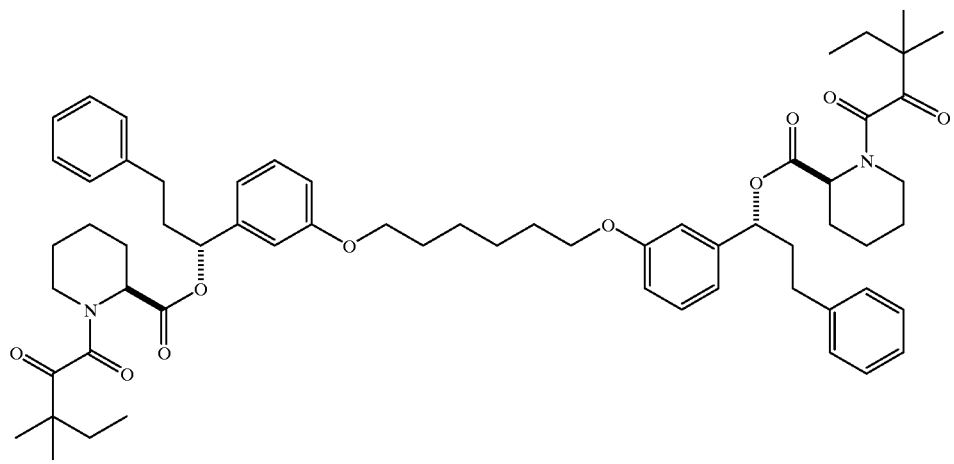
see: Holt, et al. *J. Amer. Chem. Soc*, 1993, 115, 9925–9938.
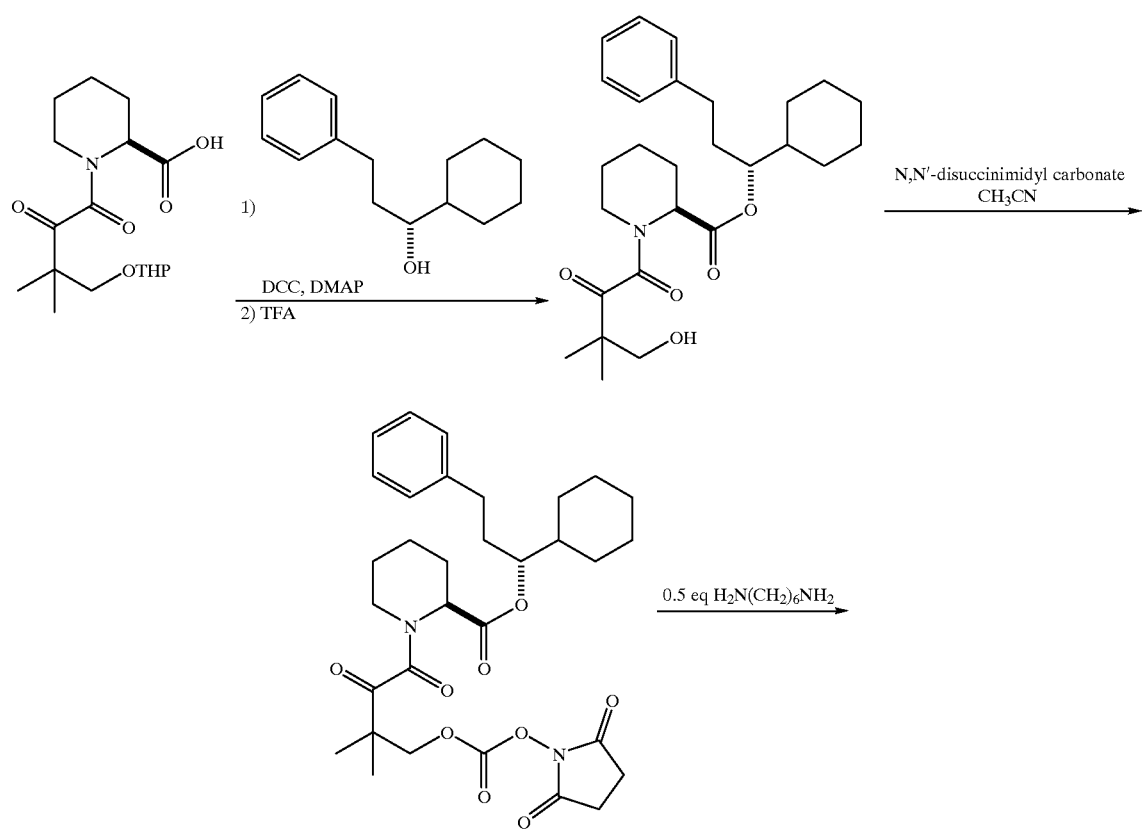

-continued
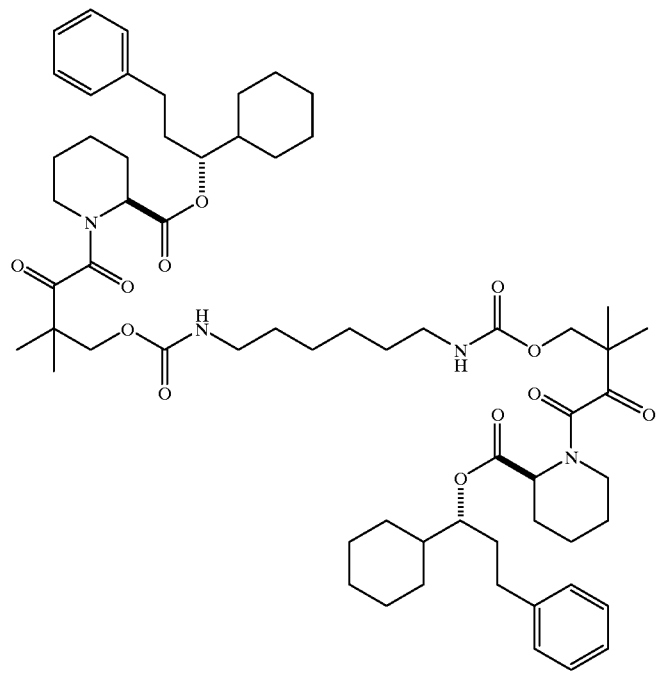
see: Holt, et al. *J. Amer. Chem. Soc.*, 1993, 115, 9925–9938.
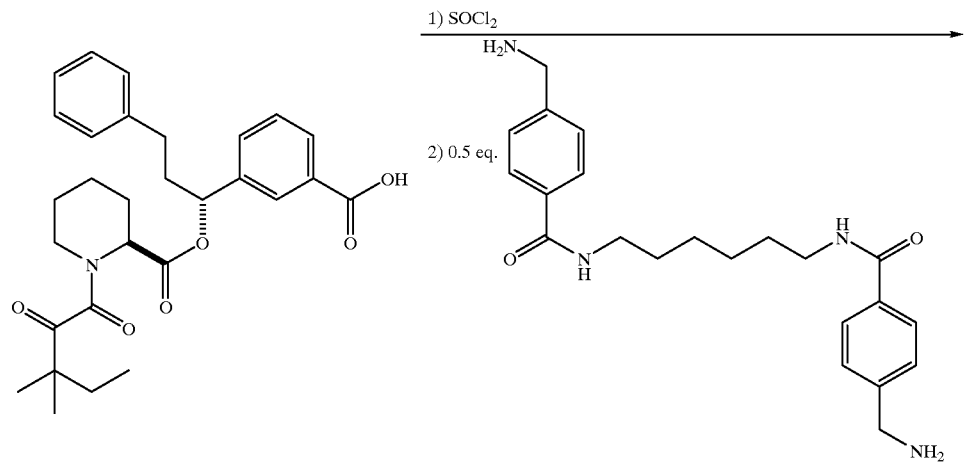

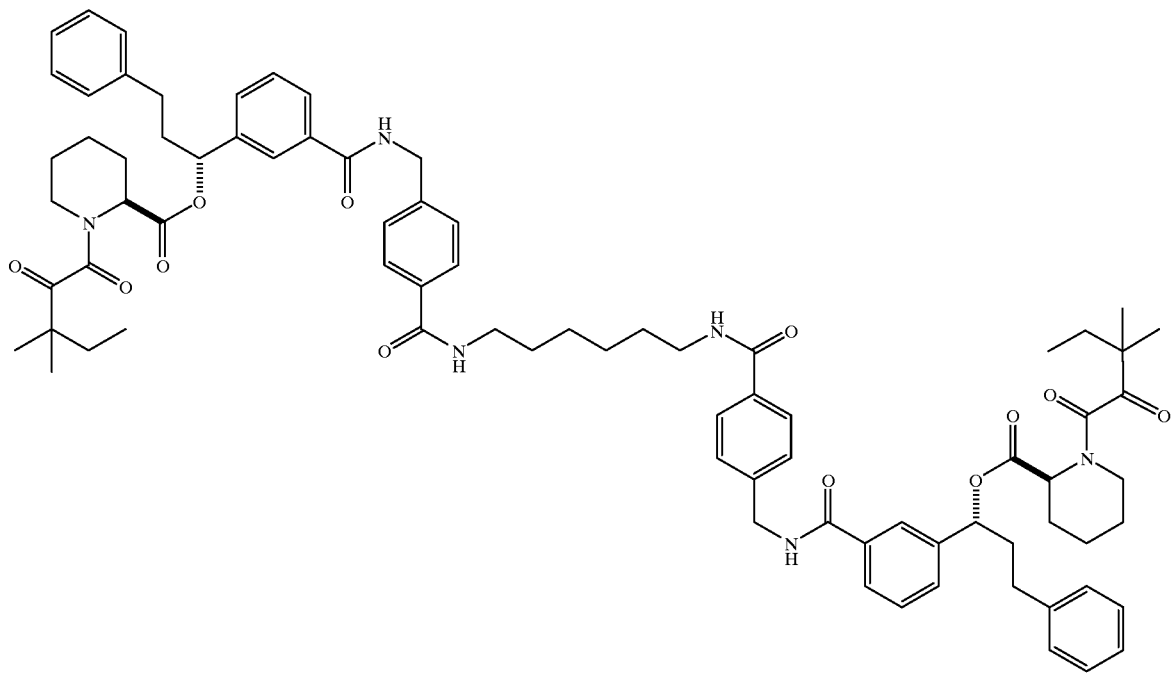
see: Yamashita, et al. *Biomed. Chem. Lett.*, 1993, 4, 325–328.
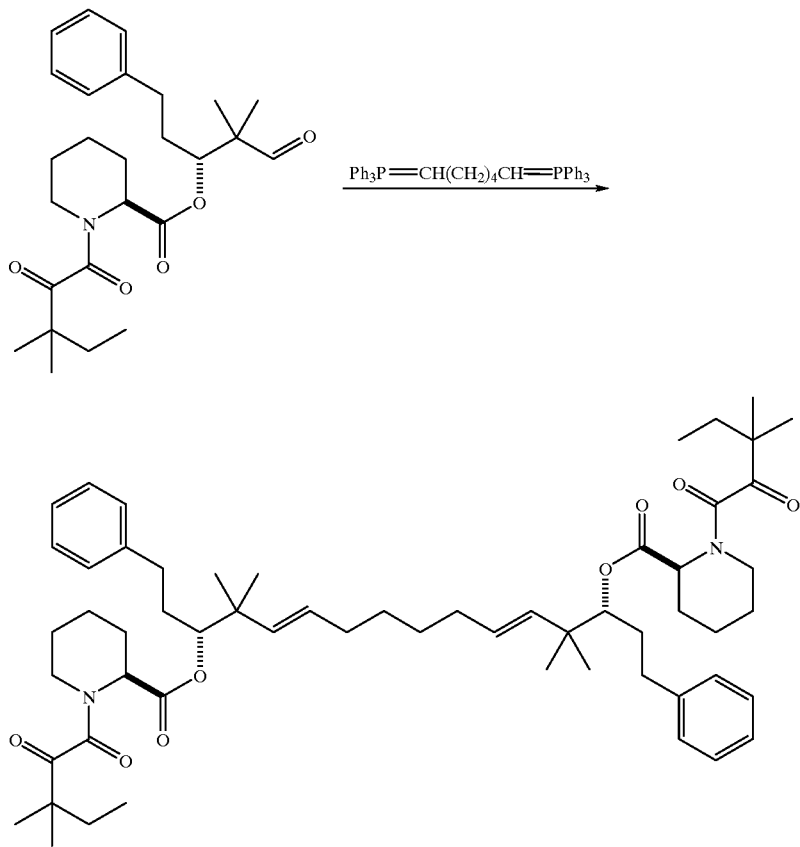

see: Yamashita, et al. *Biomed. Chem. Lett.*, 1993, 4, 325–328.

Bis-Wittig reagents are well known in the literature. See e.g., Paquette, et al, *J. Amer. Chem. Soc.*, 1985, 107, 6598; Nicolaides, *Synthesis*, 1977, 127.

see: Holt, et al. *J. Amer. Chem. Soc.*, 1993, 115, 9925–9938.

Bis-Grignard reagents are also well known in the literature. See e.g., Babudri, et al. *J. Orgmet. Chem.*, 1991, 405, 53–58; and Fujisawa et al. *Bull. Chem. Soc. Jpn.*, 1983, 56, 345.

Heterodimers (e.g., where $M^1 \neq M^2$) may be prepared by stepwise attachment of each monomer to the linker. Attachment methods may be different for each monomer and the linker may be non-symmetrical and/or differentially functionalized to facilitate stepwise attachment of monomers. By way of example, the following reaction schemes illustrate formation of heterodimers.

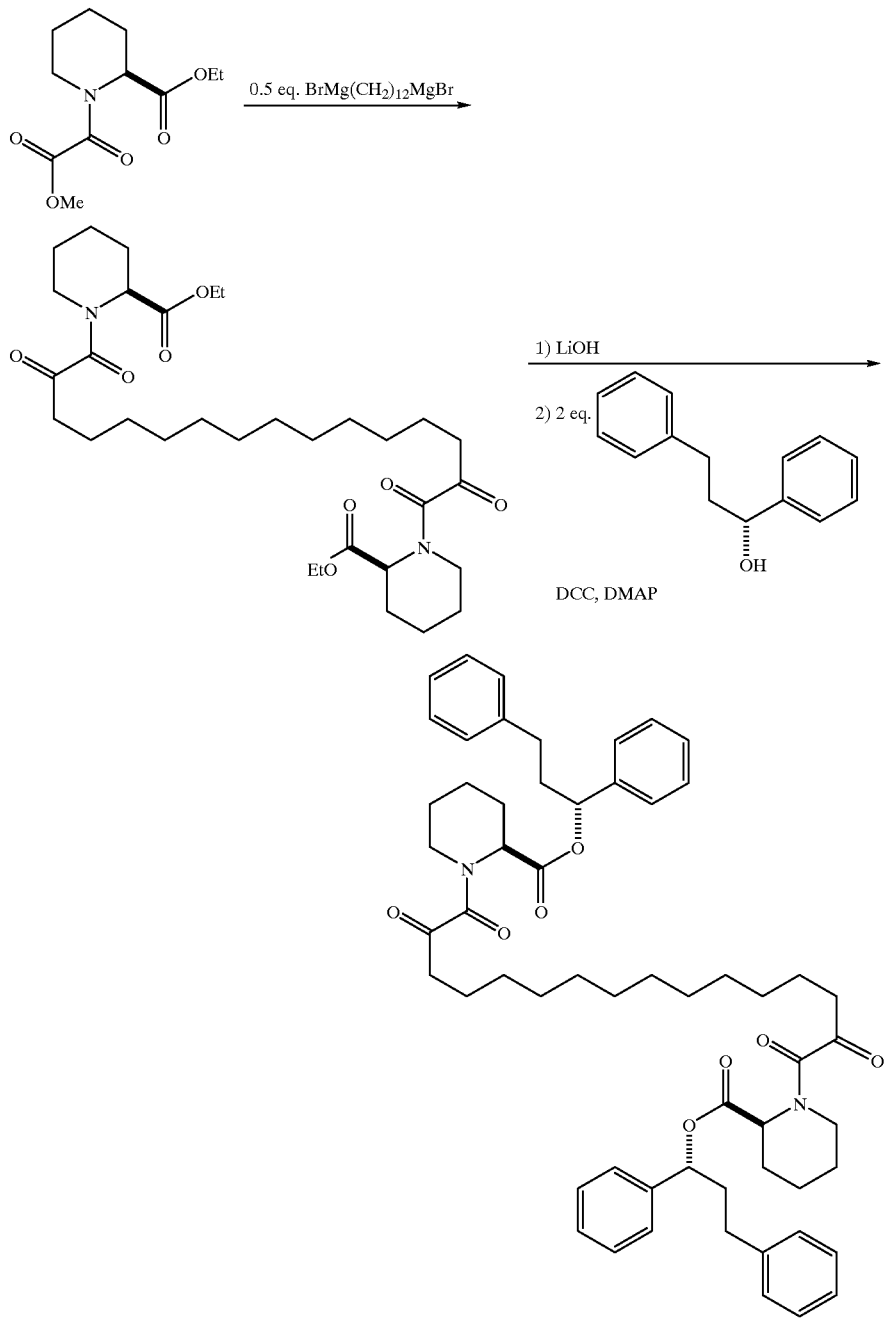

33 34
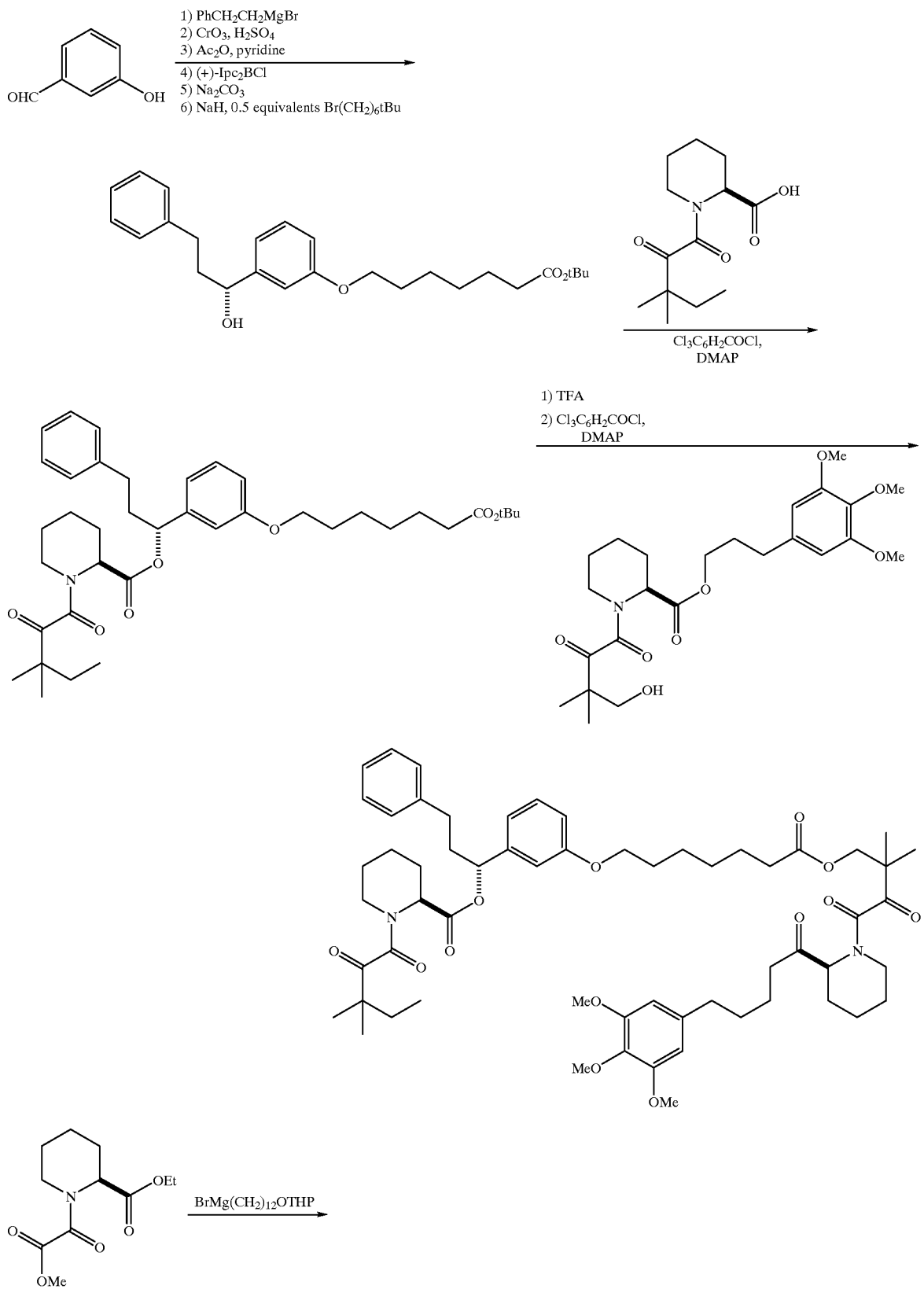

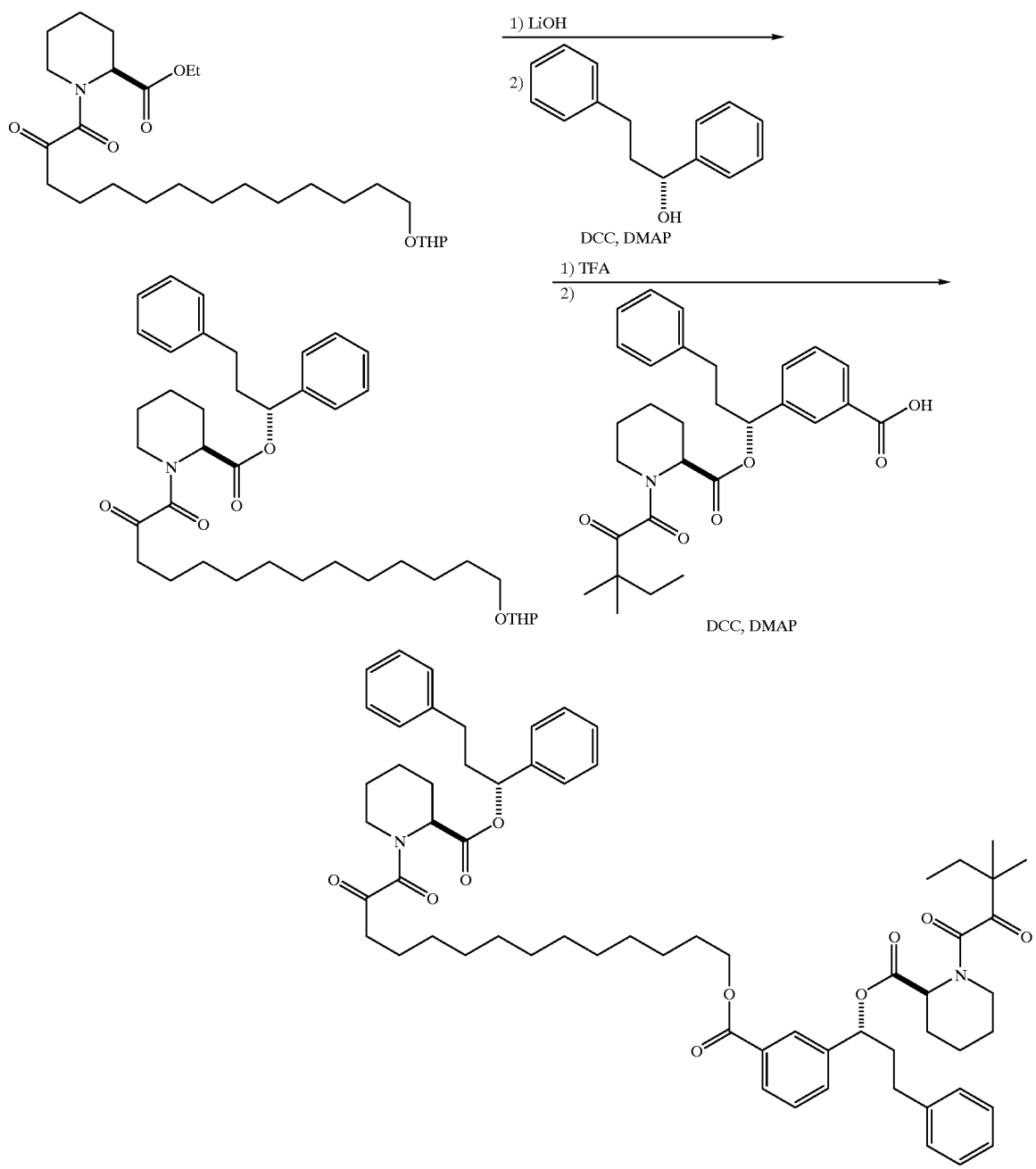

Also included in this invention are multimeric variants of formula I compounds wherein three to five formula II monomers are joined using one to four linker moieties, exemplified by but not limited to compounds of formula III and formula IV.

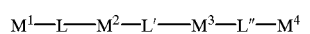 (III)

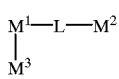 (IV)

Bumps

Certain compounds of this invention contain substituents ("bumps") which diminish, and preferably substantially preclude, their binding to native FKBP12 or other native immunophilins but which permit binding to mutant FKBPs. Mutant FKBPs may be obtained and screened for binding to a selected multimerizing compound as described in PCT/US94/01617 and PCT/US94/08008. Multimerizing agents containing such bumps permit more selective binding to mutant FKBPs or chimeras containing engineered FKBP domains without interference by indigenous pools of FKBP12, which is desirable for certain applications, especially uses in whole organisms. Preferably the bump-containing monomers and their related multimerizing agents of this invention bind to FKBP12 and/or inhibit rotamase activity of FKBP12 at least about an order of magnitude less than any of FK506, FK520 or rapamycin. Such assays are well known in the art. See e.g. Holt et al., *J. Amer. Chem Soc.*, supra. The diminution in inhibitory activity may be as great as about 2 orders of magnitude, and in some cases will exceed about three orders of magnitude. Useful bump substituents include but are not limited to alkyl, aryl, —O-alkyl, —O-aryl, substituted or unsubstituted amine, amide, carbamide and ureas, where alkyl and aryl are as previously defined. See e.g. PCT/US94/01617 and PCT/US94/08008.

One class of bumped compounds is of the formula $M^B$—L—$M^{B'}$ in which each monomer, $M^B$ (or $M^{B'}$), whether as a single isomeric form or mixture of stereoisomers is of the formula

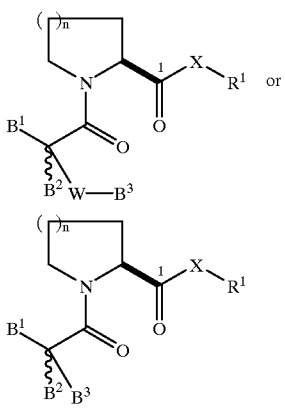

in which X, $R^1$ and n are as previously defined; $B^1$, $B^2$ and $B^3$ are independently H, C1–C10 aliphatic, heteroaliphatic, aryl or heteroaryl as those terms are used elsewhere; and W is O, S, NH, —NHC(═O)—, or —NHC(═O)—O—.

Briefly, n=1 or 2; X=O, NH or $CH_2$; and $R^1$ is $C_1$–$C_{20}$ aliphatic, heteroaliphatic, aryl or heteroaryl.

Aliphatic and heteroaliphatic moieties include both saturated and unsaturated straight chain, branched, cyclic, or polycyclic aliphatic hydrocarbons which may contain oxygen, sulfur, or nitrogen in place of one or more carbon atoms, and which are optionally substituted with one or more functional groups selected from the group consisting of hydroxy, $C_1$–$C_8$ alkoxy, acyloxy, carbamoyl, amino, N-acylamino, ketone, halogen, cyano, carboxyl, and aryl (unless otherwise specified, the alkyl, alkoxy and acyl groups preferably contain 1–6 contiguous aliphatic carbon atoms).

Aryl and heteroaryl moieties include stable cyclic, heterocyclic, polycyclic, and polyheterocyclic moieties having 3–14 carbon atoms, at least some of which are electronically unsaturated, exemplified but not limited to phenyl, biphenyl, naphthyl, pyridyl, furyl, thiophenyl, imidazoyl, pyrimidinyl, and oxazoyl; which may further be substituted with one to five members selected from the group consisting of hydroxy, $C_1$–$C_8$ alkoxy, $C_1$–$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry);

$R^1$ may optionally be joined, i.e., covalently linked, to $B^1$, $B^2$ or $B^3$ forming a macrocyclic structure (as indicated by the dashed line in II), although compounds in which $R^1$ and $B^1$, $B^2$ or $B^3$ are not covalently joined to form a macrocyle are currently of particular interest; and L is a linker moiety covalently linking monomers $M^1$ and $M^2$ through covalent bonds to either $R^1$ or $R^2$, not necessarily the same in each of $M^1$ and $M^2$.

$B^1$, $B^2$ and $B^3$ moieties other than H may contain a substituent such as a hydroxyl, carboxyl, aldehyde, allyl or amino moiety, for example, permitting covalent attachment to a linker. Examples of such compounds include the following:

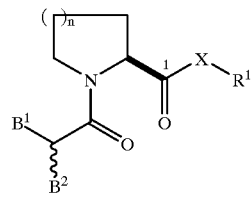

where B1 and B2 are independently branched, unbranched or cyclic aliphatic, preferably containing 1–10 carbon atoms (e.g. substituted methyl, ethyl, isopropyl, isobutyl, sec-butyl, isoamyl, cyclohexyl, etc.), alkylaryl (e.g. benzyl and substituted benzyl), alkylheterocyclic, or heterocyclic, where the heterocyclic moiety may be aromatic or not, and where any of the foregoing may contain a hydroxyl or amino group or other reactive substituent permitting covalent attachment of a linker. Note that $B^1$ and $B^2$ together may comprise a substituted or unsubstituted aliphatic, heteroaliphatic, aryl or heteroaryl ring. Additionally, in certain embodiments, $B^1$, $B^2$ or $B^3$ may be covalently linked to $R^1$ to form a macrocyclic structure.

One class of such monomers include compounds of the formula:

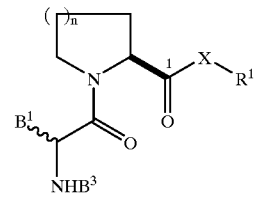

wherein —C(═O)CH($B^1$)$NHB^3$ moieties include among others D- or L- forms of naturally occurring or synthetic alpha amino acids as well as N-alkyl, N-acyl, N-aryl and N-aroyl derivatives thereof.

Examples of monomers $M^B$ include the following:

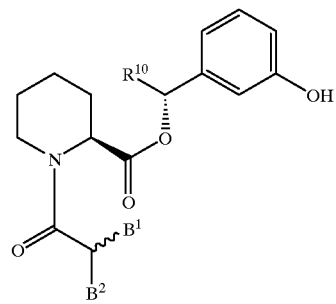

where $R^{10}$ is Ar-lower alkyl- in which Ar is a substituted or unsubstituted aryl or heteroaryl group (including, for the sake of illustration phenyl, loweralkoxyphenyl, and di-loweralkoxyphenyl such as 3,4-dimethoxyphenyl) and lower alkyl is a 1–6 carbon branched or unbranched aliphatic group; and $B^1$ and $B^2$ are independently a branched, unbranched or cyclic 2–8 carbon aliphatic or alkoxy moiety or an aryl or heteroaryl moiety, any of which may bear one or more hydroxy or amino substituents. Examples include the following:

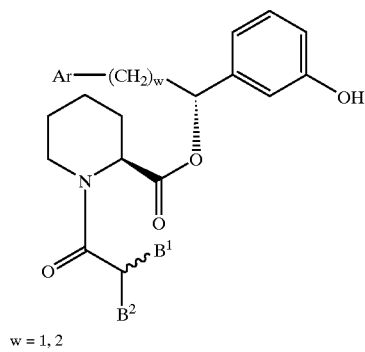

w = 1, 2 where Ar is as d efined above (e.g. Ar—(CH$_2$) is —CH$_2$CH$_2$-3,4-dimethoxyphenyl) and B1 and B2 are as indicated in the following table:

| B1 | B2 |
|---|---|
| —C(CH$_3$)$_2$(Et) | —OMe |
|  | —OEt |
|  | —O(n)Propyl |
|  | —O(n)butyl |
|  | —Obenzyl |
|  | —OCH$_2$CH(CH$_2$)$_2$ |
| -phenyl; 3- or 4-methoxyphenyl, 3,4- or 3,5-dimethoxyphenyl or 3,4,5-trimethoxyphenyl | —OMe, O-ethyl |
|  | -methyl, -ethyl, n-propyl, -allyl, i-propyl, n-butyl, or sec-butyl |
|  | -phenyl |
|  | -cyclopentyl or -cyclohexyl |
|  | —CH$_2$OH |
|  | —OCH$_2$CH$_3$ |
| -cyclohexyl | -cyclohexyl |

Such compounds may be prepared using the following synthetic approaches:

Scheme I

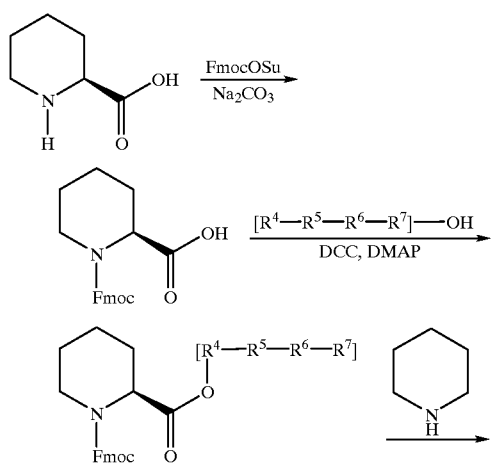

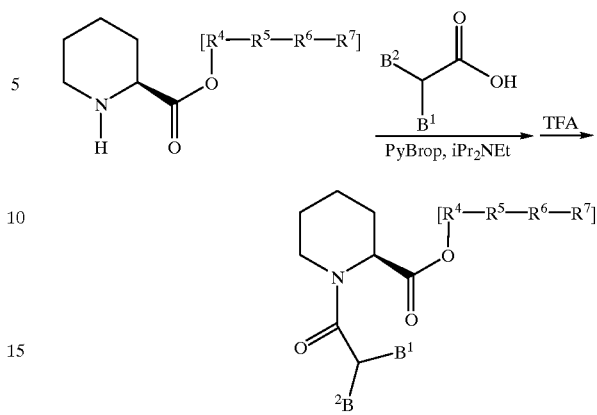

Scheme II

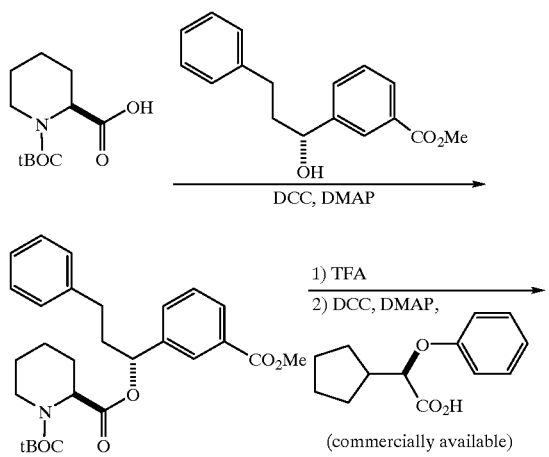

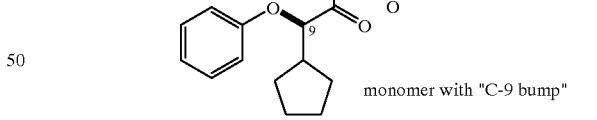

monomer with "C-9 bump"

In addition, compounds of this invention may comprise a substituted proline and pipecolic acid derivative, numerous examples of which have been described in the literature. Using synthetic procedures similar to those described above, substituted prolines and pipecolates can be utilized to prepare monomers with "bumps" at positions C-2 to C-6 as exemplified below.

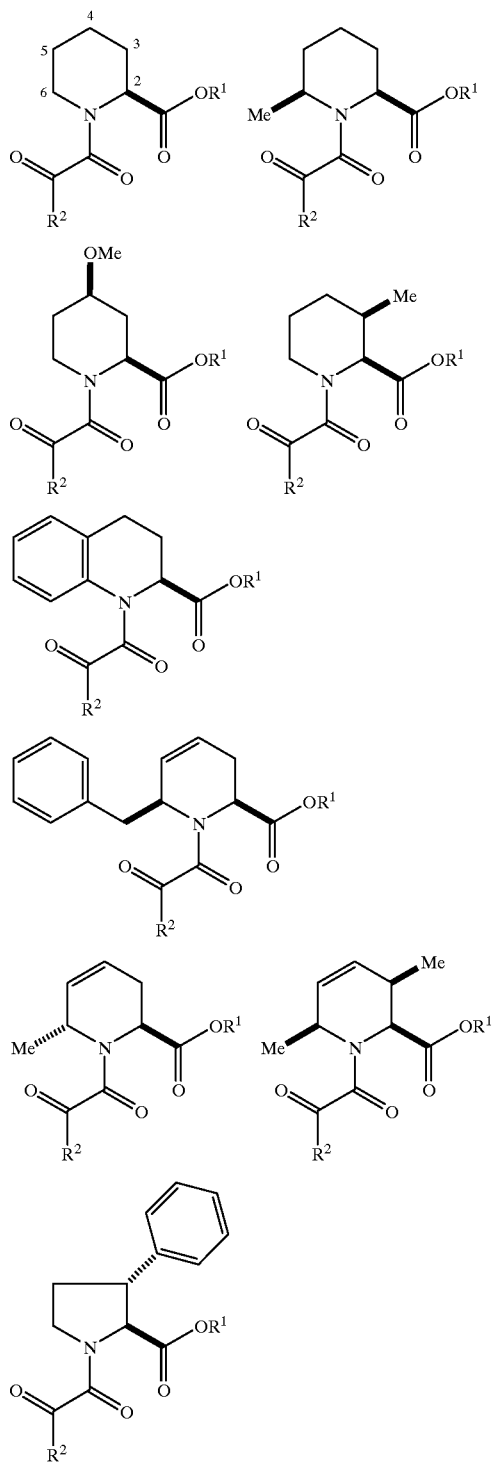

For representative examples of substituted prolines and pipecolic acids see: Chung, et al., *J. Org. Chem.*, 1990, 55, 270; Shuman, et al., *J. Org. Chem.*, 1990, 55, 738; Hanson, et al., *Tetrahedron Lett.*, 1989, 30, 5751; Bailey, et al., *Tetrahedron Lett.*, 1989, 30, 6781. Accordingly, substituted and unsubstituted 6-membered rings and fused ring systems such as the following:

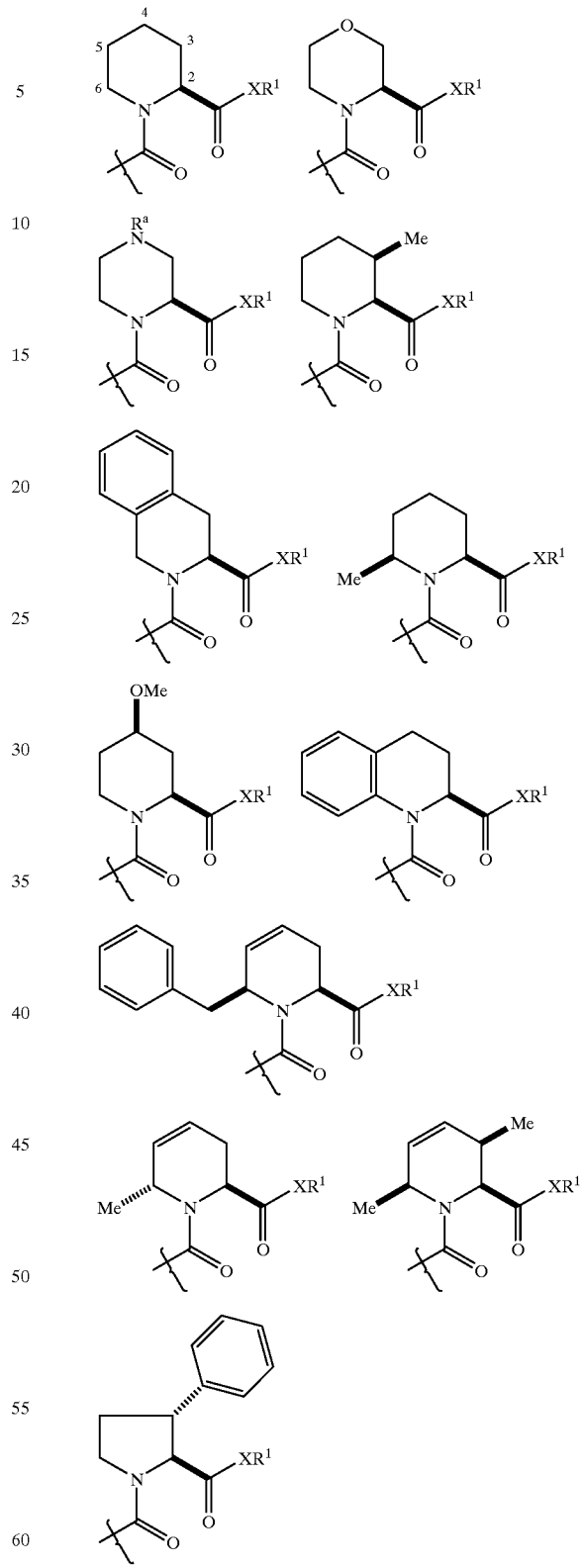

Ra = alkyl or acyl may be used in place of the substituted proline and pipecolate rings in the general formulas and specific enbodiments disclosed elsewhere herein.

Another group of compounds of this invention are based on a monomer of the formula

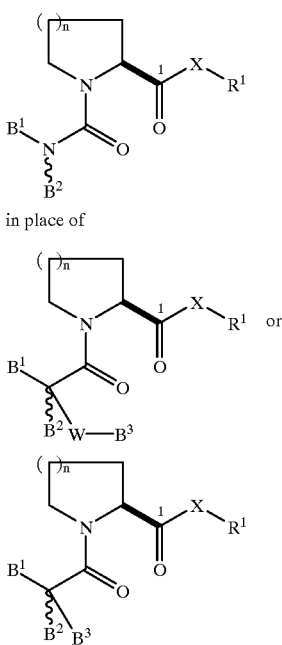

in place of or moieties of the sort depicted in the immediately preceding paragraph.

In certain applications, preferred multimerizers are those which bind, or comprise monomeric moieties, M, which bind, preferentially to mutant immunophilins (by way of non-limiting example, a human FKBP in which Phe36 is replaced with a different amino acid, preferably an amino acid with a less bulky R group such as valine or alanine) over native or naturally-ocurring immunophilins. For example, such compounds may bind preferentially to mutant FKBPs at least an order of magnitude better than they bind to human FKBP12, and in some cases may bind to mutant FKBPs greater than 2 or even 3 or more orders of magnitude better than they do to human FKBP12.

Binding affinities of various multimerizing agents of this invention or their component monomers with respect to FKBP or other immunophilin proteins may be determined by adaptation of conventional methods used in the case of FKBP. For instance, the practitioner may measure the ability of a compound of this invention to compete with the binding of a known ligand to the protein of interest. See e.g. Sierkierka et al, 1989, Nature 341, 755–757 (test compound competes with binding of labeled FK506 derivative to FKBP).

The ability of the multimerizing agents to multimerize chimeric proteins may be measured in cell-based assays by measuring the occurrence of an event triggered by such multimerization. For instance, one may use cells containing and capable of expressing DNAs encoding chimeric proteins comprising one or more immunophilin-derived ligand binding domains and one or more effector domains capable, upon multimerization, of actuating a biological response. We prefer to use cells which further contain a reporter gene under the transcriptional control of a regulatory element (i.e., promoter) which is responsive to the multimerization of the chimeric proteins. The design and preparation of illustrative components and their use in so engineering cells is described in PCT/US94/01617. The cells are grown or maintained in culture. A multimerizing agent is added to the culture medium and the presence of the reporter gene product is measured. Positive results, i.e., multimerization, correlates with transcription of the reporter gene as observed by the appearance of the reporter gene product.

Examples

Synthetic Overview, Part I:

The synthesis of functionalized chiral alcohols was carried out as follows. The unsubstituted chiral alcohol 1 was prepared from 3-hydroxybenzaldehyde in five steps following reported procedures by Holt et al. *J. Amer. Chem. Soc.*, 1993, 115, 9925–9938.

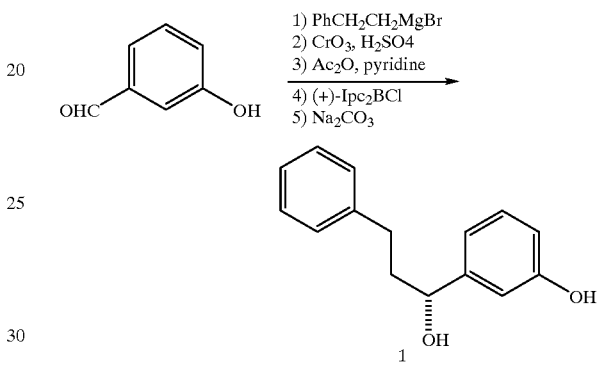

Alkylation of 1 with 3-N-Boc-aminopropylbromide in the presence of one equivalent of NaH gave 2 in good yield. Similarly, alkylation of 1 with tert-butyl bromoacetate provided 3.

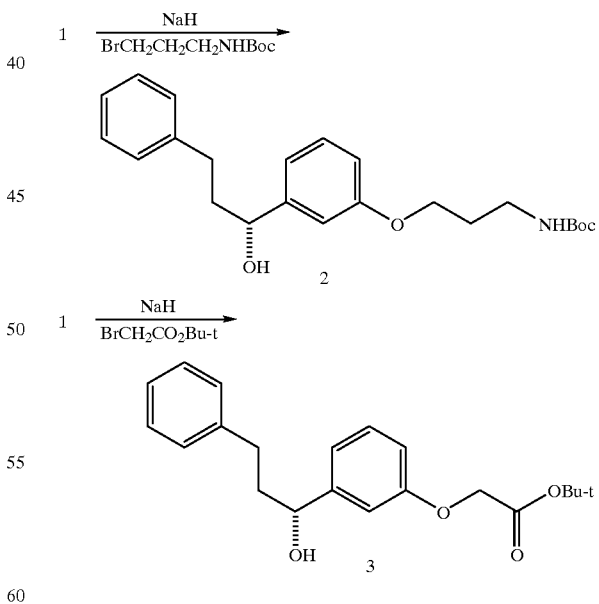

Chiral alcohols containing left-phenyl ring substitutions were prepared using a chalcone chemistry as shown in the following scheme.

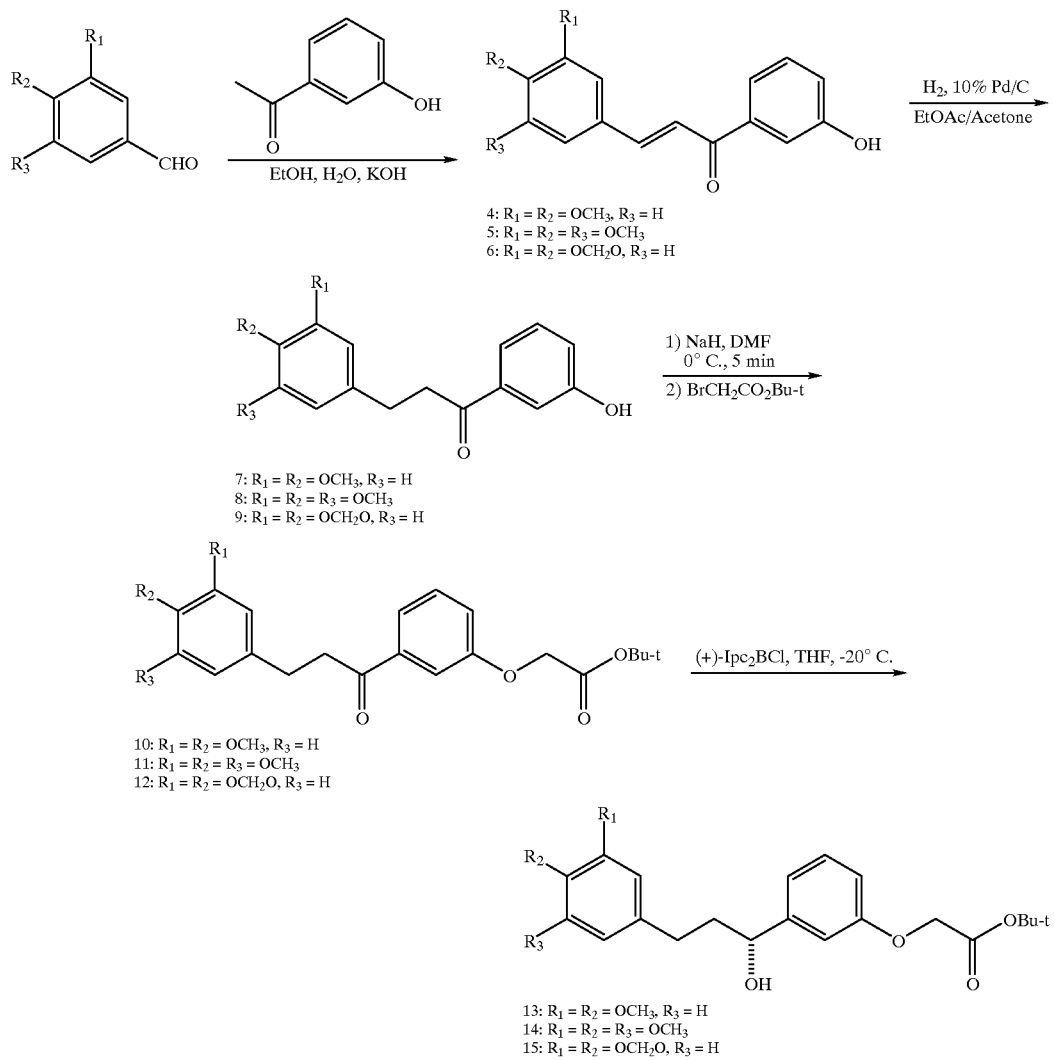
Pyridine and indole containing, chiral alcohols were prepared using a similar chalcone chemistry but with some minor modifications as shown below:
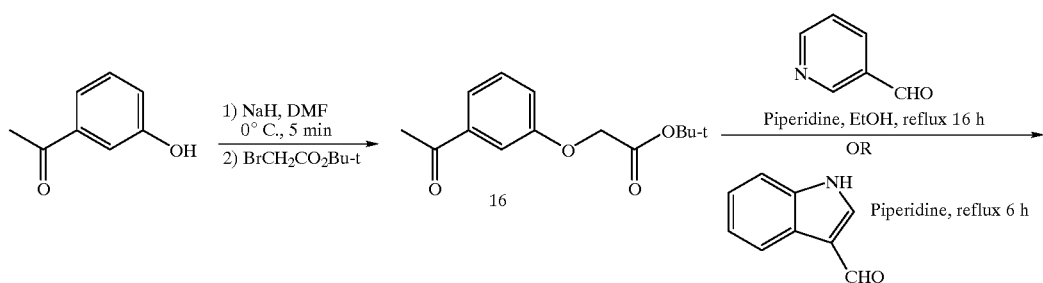

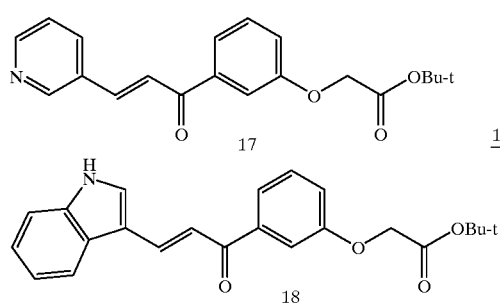
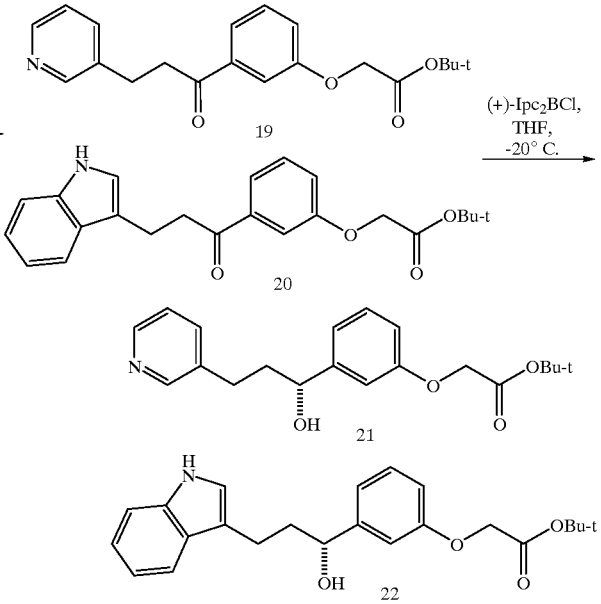

The carboxylic acid 23 was prepared from L-pipecolic acid in four steps following literature procedures by Holt et al. *J. Amer. Chem. Soc.*, 1993, 115, 9925–9938.

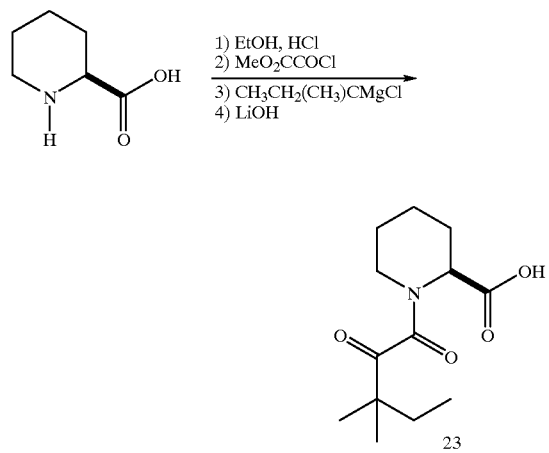

Coupling of 23 with 2 using DCC/DMAP and then removal of Boc-group with trifluoroacetic acid give the amine monomer 24 in good yield. The carboxylic acid monomers 25–30 were produced in a similar fashion.

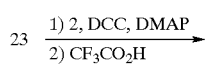

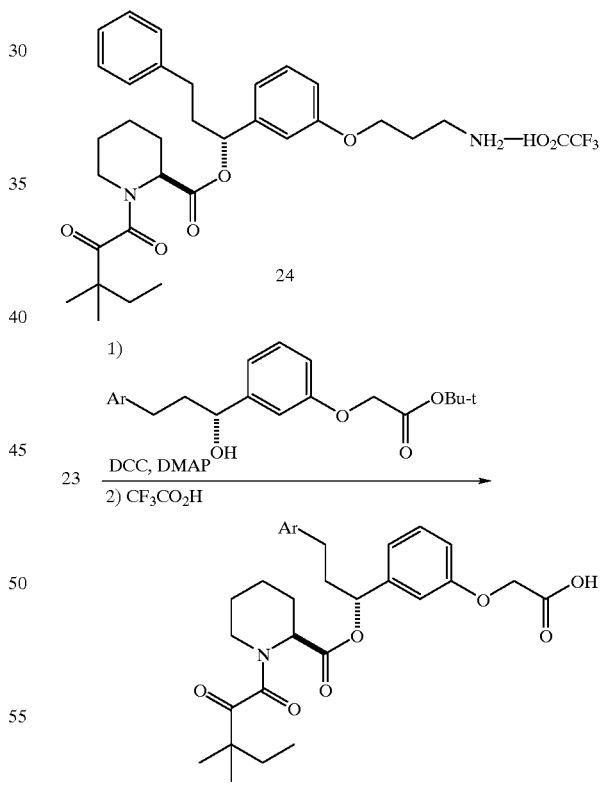

25: Ar = Ph
26: Ar = 3,4,-(OCH$_3$)$_3$Ph
27: Ar = 3,4,5-(OCH$_3$)$_3$Ph
28: Ar = 3,4-(OCH$_2$O)Ph
29: Ar = 3-pyridyl
30: Ar = 3-indolyl With monomers 24 and 25–30 in hand, various dimers were then synthesized. The amine 24 was treated with disuccinimidyl dicarboxylates to produce dimers 31–34 and 37, and 38. Reaction of 24 with benzene-1,3-disulfonyl chloride yielded 36. Coupling of 24 with triethylene glycol bis(chloroformate) yielded 39. Treatment of compound 34 with methyl iodide afforded 35 in quantitative yield.

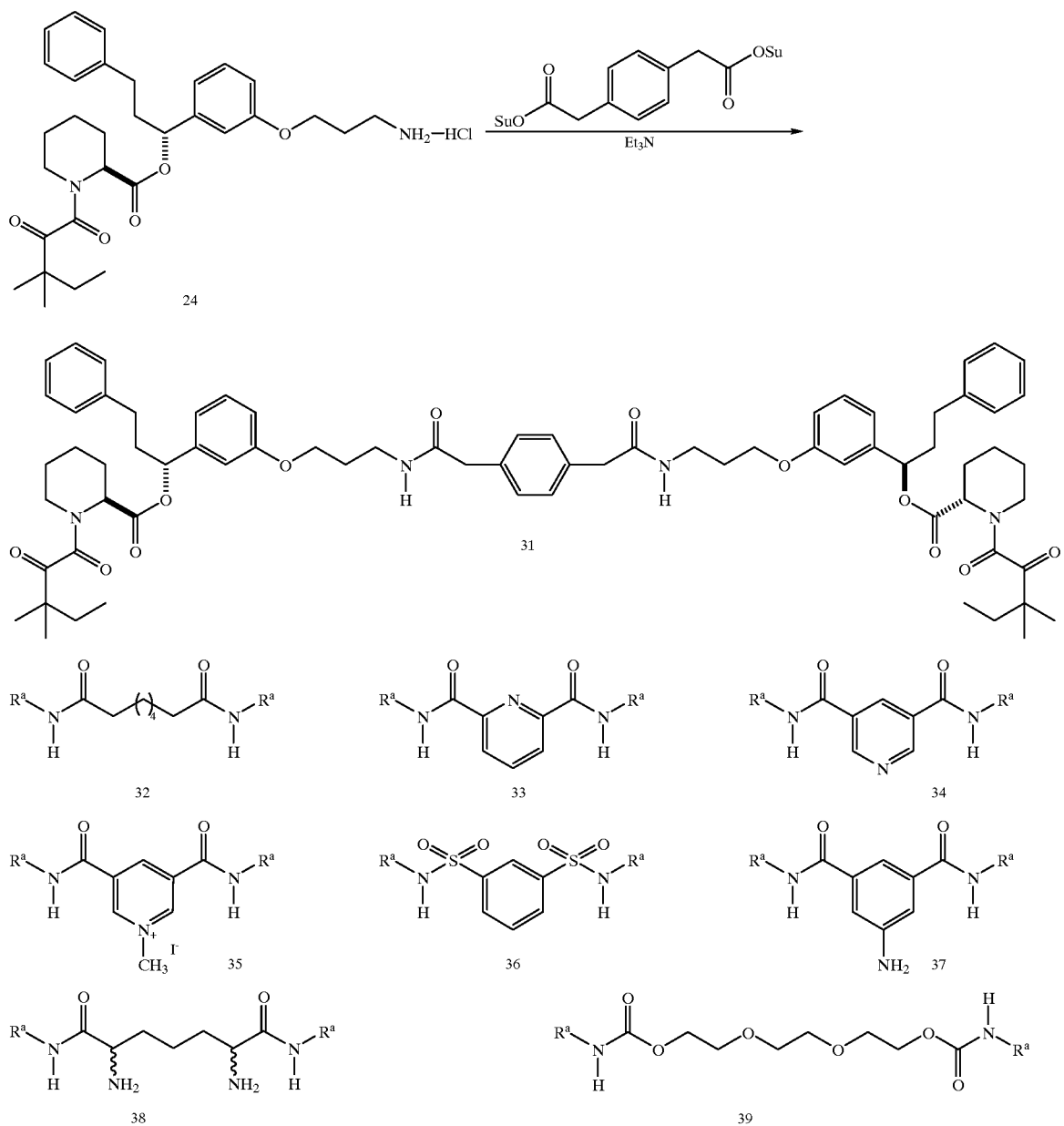

The acids 25–30 were converted to their activated succinimidyl esters and then coupled with various diamines to give dimers 40–63. ($R^a$ and $R^b$ groups represent the various monomers, M)

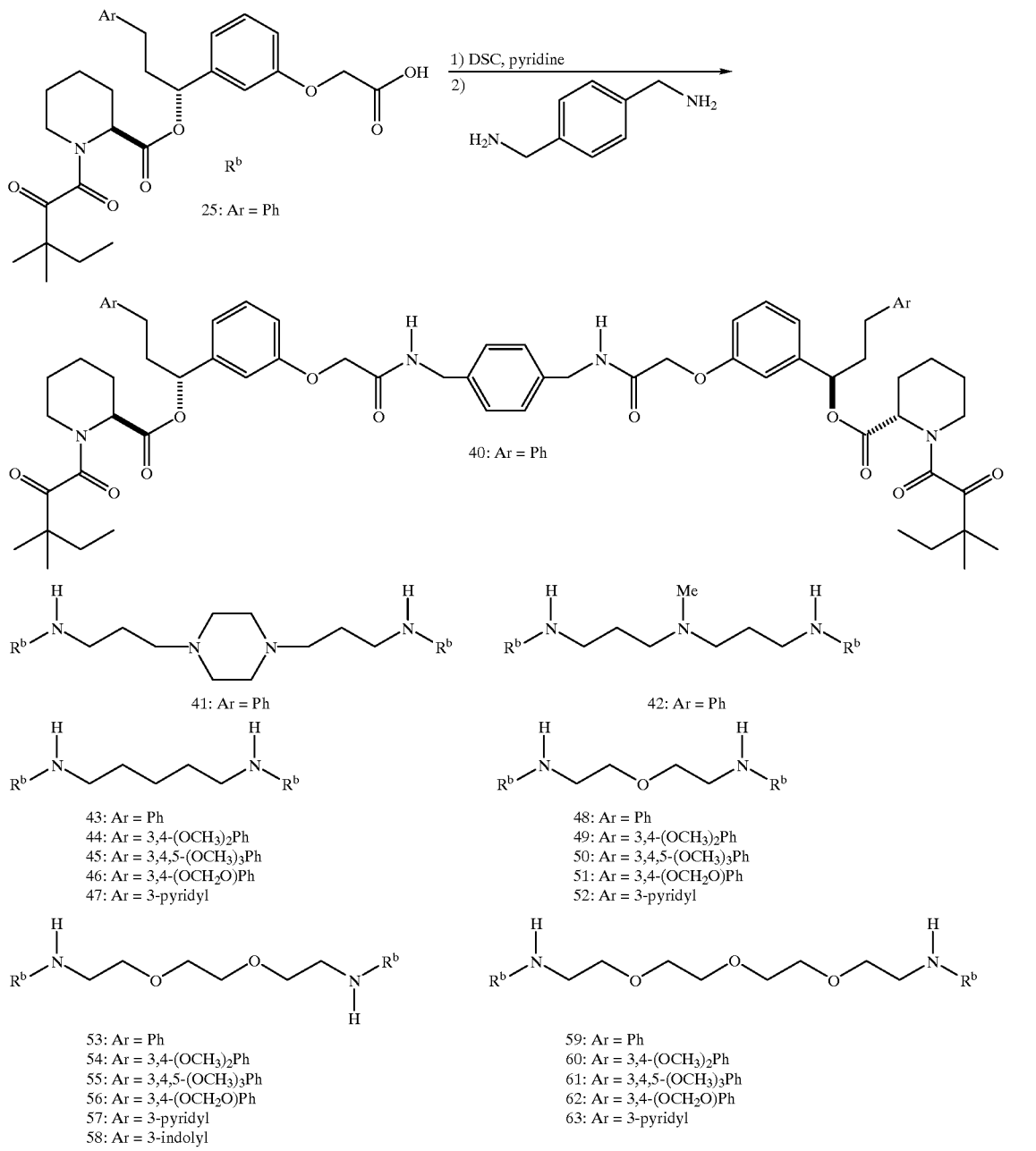

Compounds 64–67, based on the parent structure of 40 but containing the specified linkers and Ar moieties, were made by adaptation of methods described herein. The structure of the four compounds was confirmed by NMR and MS spectroscopy. All four were found to be active in cell-based transcription assays such as described infra.

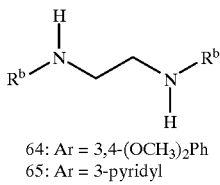

64: Ar = 3,4-(OCH₃)₂Ph
65: Ar = 3-pyridyl

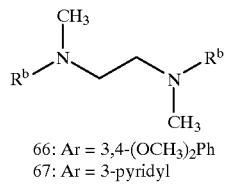

66: Ar = 3,4-(OCH₃)₂Ph
67: Ar = 3-pyridyl

Synthetic Details

General Methods

Proton and carbon magnetic resonance spectra ($^1$H, $^{13}$C NMR) were recorded on Bruker ARX-300 spectrometer. Chemical shifts are reported in parts per million (δ) relative to Me$_4$Si (δ0.0). All reagents were analytical grade and were used as received. Anhydrous solvents were purchased from Aldrich in sure-seal bottles. Chromatography refers to short column chromatography using TLC grade silica gel 60 G (Merck) and the indicated solvents as the mobile phase. HPLC was conducted using a 4.6 mm×250 mm Daicel Chiracel OD column and (unless otherwise noted) a mobile phase of 85:15 hexane-propanol, flow rate of 1 mL/min, and UV detection at 210 nm. Melting points are uncorrected.

Preparation of Functionalized Chiral Alcohols

(1R)-3-Phenyl-1-(3-(3-tert-butyloxycarbamylpropyl)oxyphenyl)propan-1-ol (2)

(1R)-3-Phenyl-1-(3-hydroxyphenyl)propan-1-ol (1, 98% ee, 1.47 g, 6.45 mmol, prepared in five steps from 3-hydroxybenzaldehyde following reported procedures by Holt et al. *J. Amer. Chem. Soc.*, 1993, 115, 9925–9938) was added to a suspension of NaH (60% dispersion in mineral oil, 310 mg, 7.74 mmol) in DMP (30 mL). 3-tert-Butyloxycarbamylpropyl bromide (3.07 g, 12.9 mmol) was then added and the resulting mixture was stirred at 40° C. under N$_2$ overnight The reaction was quenched with water (50 mL) and the mixture was extracted with EtOAc (250 mL). The organic layer was washed with saturated brine, dried (Na$_2$SO$_4$), and concentrated in vacuo. The mixture was redissolved in Et$_2$O (150 mL) and washed with 2 N NaOH (2×100 mL) to remove any unreacted 1 (which has the same R$_f$ as the product 2). The organic layer was then washed with saturated brine, dried (Na$_2$SO$_4$), and concentrated in vacuo. Chromatography (silica gel, 30% EtOAc/hexanes) afforded 2 (1.9 g, 77% yield, 96% ee by Chiracel HPLC: retention time 19.0 min for the (1R)-enantiomer and 15.7 min for the (1S)-enantiomer) as a colorless oil: $^1$H NMR (CDCl$_3$, 300 MHz) 7.40–6.85 (m, 9 H), 4.76 (t, J=5.3 Hz, 1 H), 4.12 (t, J=5.9 Hz, 2 H), 3.42 (t, J=6.3 Hz, 2 H), 2.80 (m, 2 H), 2.10–1.85 (m, 6 H), 1.53 (s, 9 H), ; $^{13}$C NMR (CDCl$_3$, 75 MHz) 159.4, 156.4, 146.8, 142.1, 129.9, 128.83, 128.78, 126.2, 118.8, 114.0, 112.4, 74.2, 66.1, 40.8, 32.4, 30.0, 28.8. MS(FAB): (M+Na)$^+$ 408.

(1R)-3-Phenyl-1-(3-(2-tert-butyloxy-2-oxoethyl)oxyphenyl)propan-1-ol (3)

(1R)-3-Phenyl-1-(3-hydroxyphenyl)propan-1-ol (1, 98% ee, 1.7 g, 7.46 mmol, prepared in five steps from 3-hydroxybenzaldehyde following reported procedures by Holt et al. *J. Amer. Chem. Soc.*, 1993, 115, 9925–9938) was added to a suspension of NaH (60% dispersion in mineral oil, 358 mg, 8.95 mmol) in DMF (50 mL). tert-Butyl bromoacetate (2.4 mL, 14.9 mmol) was then added and the resulting mixture was stirred at 40° C. under N$_2$ overnight. The reaction was quenched with water (50 mL) and the mixture was extracted with EtOAc (250 mL). The organic layer was washed with saturated brine, dried (Na$_2$SO$_4$), and concentrated in vacuo. Chromatography (silica gel, 20% EtOAc/hexanes) afforded 3 (1.64 g, 64% yield, 98% ee by Chiracel HPLC: retention time 42.2 min for the (1R)-enantiomer and 30.6 min for the (1S)-enantiomer) as a colorless oil: $^1$H NMR (CDCl$_3$, 300 MHz) 7.22–6.71 (m, 9 H), 4.58 (t, 1 H), 4.44 (s, 2 H), 2.68–2.59 (m, 2 H), 2.05–1.93 (m, 2 H), 1.41 (s, 9 H); $^{13}$C NMR (CDCl$_3$, 75 MHz) 168.4, 158.6, 146.8, 142.1, 130.0, 128.8, 128.7, 126.2, 119.5, 114.1, 112.6, 82.7, 74.1, 66.1, 40.8, 32.4, 28.4. HRMS(FAB): (M+Na)$^+$ calcd 365.1729, found 365.1721.

3,4-Dimethoxy-3'-hydroxy chalcone (4)

A solution of 3,4-Dimethoxybenzaldehyde (16.6 g, 100 mmol) in EtOH (75 mL) was treated with 3-Hydroxyacetaphenone (13.6 g, 100 mmol) and the resulting solution cooled to 0° C. in an ice bath. A 200 mL solution of aqueous KOH (28 g, 500 mmol) was added slowly and the resulting bright red solution was allowed to stir overnight (16 h) at room temperature. The mixture was then acidified to pH 5 by the dropwise addition of concentrated HCl and the resulting suspension extracted with EtOAc (2×200 mL). The combined organic extract was washed with a saturated NaCl solution (2×100 mL), dried over MgSO$_4$, filtered, evaporated, and flash chromatographed (silica gel, 30%→50% EtOAc/hexanes) to give crude material. The crude solid was crystallized from EtOAc to afford 13.9 g (49%) of a yellow colored solids: IR (neat) 3420, 1650, 1575, 1510, 1265, 1140 cm$^{-1}$; $^1$H NMR (CDCl$_3$, 300 MHz) 7.80 (d, J=15.6 Hz, 1H), 7.68 (s, 1H), 7.59, (d, J=7.7 Hz, 1H), 7.42–7.36 (m, 2H), 7.24 (dd, J=8.3, 1.8 Hz, 1H), 7.16–7.13 (m, 2H), 6.90 (d, J=8.3 Hz, 1H), 6.82 (s, 1H), 3.95 (s, 3H), 3.94 (s, 3H); $^{13}$C NMR (CDCl$_3$, 75 MHz) 191.3. 157.0, 152.0, 149.7, 146.1, 140.1, 130.2, 128.2, 123.8, 121.2, 120.7, 120.3, 115.7, 111.6, 110.7, 56.4.

3,4,5-Trimethoxy-3'-hydroxy chalcone (5)

Prepared in a similar manner as (4) from 3,4,5-trimethoxybenzaldehyde. Flash chromatography (silica gel, 30%→50% EtOAc/hexanes) afforded 2.61 g (17%) of yellow colored solids: $^1$H NMR (CDCl$_3$, 300 MHz) 9.80 (s, 1H), 7.82 (d, J=15.6 Hz, 1H), 7.70–7.63 (m, 2H), 7.48 (s, 1H), 7.39 (app t, J=7.9 Hz, 1H) 7.23 (s, 2H) 7.08 (d, J=7.6 Hz, 1H), 3.87 (s, 6H), 3.73 (s, 3H); $^{13}$C NMR (CDCl$_3$, 75 MHz) 189.5, 158.1, 153.5, 144.7, 140.1, 139.5, 130.6, 130.1, 121.8, 120.5, 119.9, 115.0, 106.9, 60.5, 56.5.

3'-Hydroxy-3,4-methylenedioxy chalcone (6)

Prepared in a similar manner as (4) from piperonal. Crude solids (26.7 g, 100%) were carried on directly to the next reaction step without chromatographic purification or characterization.

3-(3,4-Dimethoxyphenyl)-1-(3-hydroxyphenyl)propan-1-one (7)

A solution of 3,4-Dimethoxy-3'-hydroxy chalcone (4) (10 g, 35.2 mmol) in a 1:1 mixture of EtOAc:Acetone (40 mL) was treated with 10% Pd on Carbon (500 mg) and the mixture hydrogenated at 40–50 psi pressure of H$_2$ for 3 h. The reaction mixture was filtered through a pad of Celite with the aid of acetone and the filtrate concentrated to afford a crude solid. The crude solid was triturated with EtOAc and filtered to afford 7.83 g (78%) of white solids which proved to be of ~90% purity by $^1$H NMR analysis: $^1$H NMR (CDCl$_3$, 300 MHz) 7.56 (s, 1H), 7.55, (d, J=2.2 Hz, 1H), 7.53–7.33 (m, 1H), 7.10 (dd, J=7.9, 2.4 Hz, 1H), 6.80–7.79 (m, 3H), 6.61 (s, 1H), 3.86 (s, 3H), 3.86 (s, 3H), 3.28 (t, J=7.9 Hz, 2H), 3.02 (t, J=7.9 Hz, 2H); $^{13}$C NMR (CDCl$_3$, 75 MHz) 200.6, 156.9, 149.3, 147.8, 138.6, 134.2, 130.3, 121.1, 120.6, 115.0, 112.4, 111.8, 56.3, 41.2, 30.3.

1-(3-Hydroxyphenyl)-3-(3,4,5-trimethoxyphenyl)propan-1-one (8)

Prepared in a similar manner as (7) from 3,4,5-Trimethoxy-3'-hydroxy chalcone (5). Flash chromatography (silica gel, 40%→50% EtOAc/hexanes) of crude material afforded 1.37 g (68%) of white solids: IR (neat) 3395, 2940, 1680, 1590, 1505, 1455, 1240, 1125 cm$^{-1}$; $^1$H NMR (CDCl$_3$, 300 MHz) 7.54–7.52 (m, 2H), 7.34 (app t, J=8.1 Hz, 1H), 7.10 (dd, J=7.9, 2.2 Hz, 1H), 6.48 (s, 2H), 6.08 (s, 1H), 3.85 (s, 9H), 3.30 (t, J=7.3 Hz, 2H), 3.02 (t, J=7.77 Hz, 2H); $^{13}$C NMR (CDCl$_3$, 75 MHz) 200.0, 156.7, 153.6, 138.7, 137.4, 136.7, 130.3, 120.9, 115.0, 105.8, 61.3, 56.5, 41.0, 31.0.

1-(3-Hydroxyphenyl)-3-(3,4-methylenedioxyphenyl) propan-1-one (9)

Prepared in a similar manner as (7) from 3'-Hydroxy-3, 4-methylenedioxy chalcone (6). Crystallization of crude material from EtOAc/hexanes afforded 4.10 g (41%) of white solids: $^1$H NMR (CDCl$_3$, 300 MHz) 9.73 (s, 1H), 7.43 (d, J=7.8 Hz, 1H), 7.34–7.29 (m, 2H), 7.02 (dd, J=8.0 Hz, 1H), 6.88 (m, 1H), 6.80 (d, J=7.9 Hz, 1H), 6.71 (d, J=7.9 Hz, 1H), 5.96 (s, 2H), 3.26 (t, J=7.6 Hz, 2H), 2.84 (t, J=7.5 Hz, 2H); $^{13}$C NMR (CDCl$_3$, 75 MHz) 199.4 158.0, 147.5, 145.7, 138.4, 135.4, 130.1, 121.5, 120.5, 119.3, 114.4, 109.2, 108.4, 101.0, 40.2, 29.7.

1-(3-(tert-Butoxycarbonylmethoxy)phenyl)-3-(3,4-dimethoxyphenyl)propan-1-one (10)

A 60% mineral oil suspension of NaH (279 mg, 6.98 mmol) in anhydrous DMF (10 mL) was cooled to 0° C. in an ice bath and solid 3-(3,4-Dimethoxyphenyl)-1-(3-hydroxyphenyl)propan-1-one (7) (2 g, 6.98 mmol) added in one portion. The resulting yellow solution was stirred for 5 min after which time tert-butylbromoacetate (1.18 mL, 7.33 mmol) was added. Stirring was continued at 0° C. for 15 min after which time the reaction mixture was warmed to room temperature and partitioned between diethyl ether (50 mL) and water (50 mL). The organic layer was washed with a saturated NaCl solution (2×50 mL), dried over MgSO$_4$, filtered, evaporated, and flash chromatographed (silica gel, 30% EtOAc/hexanes) to afford 2.30 g (82%) of a clear colorless oil: IR (neat) 2980, 1750, 1685, 1590, 1515, 1260, 1155 cm$^{-1}$; $^1$H NMR (CDCl$_3$, 300 MHz) 7.59 (d, J=7.7 Hz, 1H), 7.49 (s, 1H), 7.39 (app t, J=8.0 Hz, 1H), 7.14 (dd, J=8.2, 2.6 Hz, 1H), 6.81–6.79 (m, 3H), 4.58 (s, 2H), 3.89 (s, 3H), 3.88 (s, 3H), 3.28 (t, J=7.3 Hz, 2H), 3.02 (t, J=7.8 Hz, 2H), 1.51 (s, 9H); $^{13}$C NMR (CDCl$_3$, 75 MHz) 199.2, 168.0, 158.6, 149.3, 147.8, 138.7, 134.2, 130.1, 121.8, 120.6, 113.5, 112.2, 111.8, 108.1, 83.0, 66.1, 56.2, 41.1, 30.2, 28.4.

1-(3-(tert-Butoxycarbonylmethoxy)phenyl)-3-(3,4,5-trimethoxyphenyl)propan-1-one (11)

Prepared in a similar manner as (10) from 1-(3-Hydroxyphenyl)-3-(3,4,5-trimethoxyphenyl)propan-1-one (8). Flash chromatography (silica gel, 30%→40% EtOAc/hexanes) of crude material afforded 1.30 g (96%) of a clear colorless oil: IR (neat) 2955, 1750, 1684, 1590, 1455, 1230, 1150, 1125 cm$^{-1}$; $^1$H NMR (CDCl$_3$, 300 MHz) 7.59 (d, J=7.7 Hz, 1H), 7.49 (s, 1H), 7.39 (app t, J=7.9 Hz, 1H), 7.14 (dd, J=8.2, 2.6 Hz, 1H), 6.47 (s, 2H), 4.58 (s, 2H), 3.86 (s, 6H), 3.84 (s, 3H), 3.28 (t, J=7.3 Hz, 2H), 3.01 (t, J=7.8 Hz, 2H), 1.50 (s, 9H); $^{13}$C NMR (CDCl$_3$, 75 MHz) 199.1, 168.0, 158.5, 153.6, 138.6, 137.4, 136.8, 130.1, 121.8, 120.4, 113.6, 105.8, 83.0, 66.1, 61.2, 56.5, 41.0, 31.0, 28.4.

1-(3-(tert-Butoxycarbonylmethoxy)phenyl)-3-(3,4-methylenedioxyphenyl)propan-1-one (12)

Prepared in a similar manner as (10) from 1-(3-Hydroxyphenyl)-3-(3,4-methylenedioxyphenyl)propan-1-one (9). Flash chromatography (silica gel, 20%→30% EtOAc/hexanes) of crude material afforded 5.04 g (89%) of a clear colorless oil: IR (neat) 2980, 1750, 1685, 1490, 1445, 1245, 1155, 1040 cm$^{-1}$; $^1$H NMR (CDCl$_3$, 300 MHz) 7.58 (dd, J=6.7, 1.1 Hz, 1H), 7.48 (s, 1H), 7.39 (app t, J=8.0 Hz, 1H), 7.17–7.13 (m, 1H), 6.89–6.69 (m, 4H), 5.94 (s, 2H), 4.58 (s, 2H), 3.25 (t, J=7.8 Hz, 2H), 2.99 (t, J=7.8 Hz, 2H), 1.51 (s, 9H); $^{13}$C NMR (CDCl$_3$, 75 MHz) 199.0, 168.0, 158.5, 148.1, 146.3, 138.6, 135.4, 130.1, 121.8, 121.5, 120.6, 113.4, 109.3, 108.7, 101.2, 83.0, 66.1, 41.1, 20.3, 28.4.

(R) 1-(3-(tert-Butoxycarbonylmethoxy)phenyl)-3-(3,4-dimethoxyphenyl)propan-1-ol (13)

A solution of 1-(3-(tert-Butoxycarbonylmethoxy)phenyl)-3-(3,4-dimethoxyphenyl)propan-1-one (10) (3.0 g, 7.49 mmol) in THF (5 mL) at −20° C. was treated with a solution of (+)-B-chlorodiisopinocamphenylborane (2.9 g, 8.99 mmol) in THF (10 mL) at −20° C. The resulting mixture was allowed to stand in a −20° C. freezer for 48 h after which time the mixture was evaporated and treated with diethyl ether (25 mL) followed by diethanolamine (8 mL). The viscous mixture was allowed to stir at room temperature for 3 h, after which time, was filtered through a pad of Celite with the aid of diethyl ether. The cloudy filtrate was evaporated and flash chromatographed (silica gel, 30%→40% EtOAc/hexanes) to afford 2.72 g (90%) of a clear colorless oil. (95% ee by Chiracel HPLC, 25% i-PrOH/hexanes, retention time 44.4 min for the R-enantiomer and 35.7 min for the S-enantiomer): IR (neat) 3525, 2935, 1750, 1515, 1150 cm$^{-1}$; $^1$H NMR (CDCl$_3$, 300 MHz) 7.30–7.25 (m, 2H), 6.99–6.73 (m, 5H), 4.68 (m, 1H), 4.53 (s, 2H), 3.88 (s, 3H), 3.87 (s, 3H), 2.72–2.63 (m, 2H), 2.12–1.97 (m, 2H), 1.50 (s, 9H); $^{13}$C NMR (CDCl$_3$, 75 MHz) 168.4, 158.5, 149.3, 147.6, 146.9, 134.8, 130.0, 120.6, 119.5, 114.0, 112.6, 112.2, 111.7, 82.7, 74.1, 66.1, 56.3, 56.2, 41.0, 32.0, 28.4.

(1R)-3-(3,4,5-Trimethoxyphenyl)-1-(3-(tert-butoxycarbonylmethoxy)phenyl)-propan-1-ol (14)

To a solution of 11 (1.30 g, 3.0 mmol) in THF (5 mL) at −23° C. under N$_2$ was added a cold (−23° C.) solution of (+)-B-chlorodiisopincampheylborane (1.64 g, 5.1 mmol) in THF (10 mL). The mixture was placed in a freezer for 3 days. Then, the mixture was concentrated in vacuo and the residue was redissolved in diethyl ether (60 mL). The ether solution was treated with diethanolamine (0.86 mL, 9.0 mmol) with vigorous stirring at room temperature for 3 h. The white precipitates were filtered off and the filtrate was concentrated in vacuo. Chromatography on silica (50–100% EtOAc/hexanes) provided 1.3 g (99%) of a colorless oil (98.1% ee by Chiracel HPLC, 20% i-PrOH/hexanes, retention time 46.4 min for the R-enantiomer and 40.0 min for the S-enantiomer). $^1$H NMR (CDCl$_3$, 300 MHz) 7.28 (t, J=7.8 Hz, 1 H), 6.96 (m, 2 H), 6.82 (m, 1 H), 6.41 (s, 2 H), 4.69 (t, J=6.2 Hz, 1 H), 4.52 (s, 2 H), 3.85 (s, 6 H), 3.83 (s, 3 H), 2.65 (m, 2 H), 2.05 (m, 2 H), 1.50 (s, 9 H); $^{13}$C NMR (CDCl$_3$, 75 MHz) 168.4, 158.6, 153.5, 146.8, 137.9, 136.6, 130.0, 119.5, 114.0, 112.7, 105.7, 82.8, 74.1, 66.0, 61.2, 56.5, 40.8, 32.8, 28.4.

(R) 1-(3-(tert-Butoxycarbonylmethoxy)phenyl)-3-(3,4-methylenedioxyphenyl)propan-1-ol (15)

Prepared in a similar manner as (13) from 1-(3-(tert-Butoxycarbonylmethoxy)phenyl)-3-(3,4-methylenedioxyphenyl)propan-1-one (12). Flash chromatography (silica gel, 20%→25% EtOAc/hexanes) of crude material afforded 3.84 g (96%) of a clear colorless oil: IR (neat) 3440, 1750, 1490, 1440, 1245, 1150, 1040 cm$^{-1}$; $^1$H NMR (CDCl$_3$, 300 MHz) 7.30–7.24 (m, 1H), 6.98–6.93 (m, 2H), 6.82 (dd, J=8.2, 2.5 Hz, 1H), 6.75–6.64 (m, 3H), 5.93 (s, 2H), 4.67–4.63 (m, 1H), 4.53 (s, 2H), 2.68–2.60 (mn, 2H), 2.10–1.95 (m, 3H), 1.51 (s, 9H); $^{13}$C NMR (CDCl$_3$, 75 MHz) 168.4, 158.5, 148.0, 146.9, 146.0, 136.0, 130.0, 121.5, 119.5, 114.1, 112.5, 109.3, 108.5, 101.1, 82.7, 73.9, 66.1, 41.1, 32.1, 28.4.

3'-(tert-Butoxycarbonylmethoxy)acetophenone (16)

To a suspension of NaH (60% dispersion in mineral oil, 1.47 g, 36.7 mmol) in anhydrous DMF (50 mL) at 0° C. was added solid 3'-hydroxyacetophenone (5.0 g, 36.7 mmol). The mixture was stirred under N$_2$ for 10 min and a clear yellow solution was formed. Then, tert-butylbromoacetate (6.23 mL, 38.5 mmol) was added and the mixture stirred at 0° C. for 5 min and then at room temperature for 20 min. TLC showed no starting material remaining. The mixture was partitioned between EtOAc (250 mL) and water (100 mL). The organic layer was separated, washed with saturated brine, dried (MgSO$_4$) and concentrated in vacuo. Chromatography on silica (20% EtOAc/hexanes) gave 7.6 g (83%) of a white crystal. $^1$H NMR (CDCl$_3$, 300 MHz) 7.60–7.14 (m, 4 H), 4.59 (s, 2 H), 2.60 (s, 3 H), 1.51 (s, 9 H); $^{13}$C NMR (CDCl$_3$, 75 MHz) 198.0, 168.0, 158.6, 138.9, 130.1, 122.3, 120.6, 113.5, 83.0, 66.1, 28.4, 27.0.

3-(3-Pyridyl)-1-(3-(tert-butoxycarbonylmethoxy)phenyl)-2-propen-1-one (17)

A mixture of 16 (4.0 g, 16 mmol), nicotinaldehyde (1.89 mL, 20 mmol), and piperidine (4.0 mL, 40 mmol) in absolute EtOH (65 mL) was heated at reflux for 16 h. The mixture was cooled and concentrated in vacuo. Chromatography on silica gel (30–60% EtOAc/hexanes) gave a mixture of unreacted nicotinaldehyde and 17 (both have the same R$_f$ on TLC). Washing of the mixture with hexane in a filter funnel provide 1.73 g (32%) of pure 17 as a yellow crystal. $^1$H NMR (CDCl$_3$, 300 MHz) 8.87 (d, J=2.1 Hz, 1 H), 8.66 (dd, J=4.8, 1.5 Hz, 1 H), 7.97 (d, J=7.9 Hz, 1 H), 7.80 (d, J=16.7 Hz, 1 H), 7.66 (d, J=7.6 Hz, 1 H), 7.60 (d, J=15.9 Hz, 1 H), 7.55 (s, 1 H), 7.46 (t, J=7.8 Hz, 1 H), 7.38 (dd, J=7.9, 4.8 Hz, 1 H), 7.20 (dd, J=8.2, 2.6 Hz, 1 H), 4.62 (s, 2 H), 1.52 (s, 9 H); $^{13}$C NMR (CDCl$_3$, 75 MHz) 189.7, 175.0, 168.0, 158.7, 151.6, 150.5, 141.4, 139.5, 134.9, 131.0, 130.2, 124.2, 122.3, 120.6, 114.1, 83.1, 66.2, 28.4.

1-(3-(tert-Butoxycarbonylmethoxy)phenyl)-3-(3-indoyl)-2-propen-1-one (18)

A mixture of 16 (2.0 g, 8.0 mmol) and 3-indolecarboxaldehyde (967 mg, 6.66 mmol) in piperidine (4 mL) was heated at reflux for 6 h. The reaction mixture was cooled and treated with pH 7 phosphate buffer (25 mL) and EtOAc (50 mL). The organic portion was washed with a saturated NaHCO$_3$ solution (2×50 mL) followed by a saturated NaCl solution (2×25 mL) solution. The organic layer was then dried over MgSO$_4$, filtered, evaporated, and flash chromatographed (silica gel, 50% EtOAc/hexanes) to afford 1.47 g (59%) of yellow solids. IR (neat) 1730, 1650, 1560, 1240, 1150 cm$^{-1}$; $^1$H NMR (MeOH, 300 MHz) 8.06 (d, J=15.5 Hz, 1 H), 7.94–7.91 (m, 1 H), 7.76 (s, 1H), 7.62 (dd, J=6.7, 1.1 Hz, 1H), 7.52–7.42 (m, 4H), 7.40–7.17 (m, 3H), 4.61 (s, 2H), 1.42 (s, 9H); $^{13}$C NMR (MeOH, 75 MHz) 192.9, 170.5, 160.2, 142.4, 142.1, 139.8, 134.2, 131.3, 127.2, 124.5, 123.0, 121.7, 120.7, 117.4, 115.3, 113.7, 84.0, 67.2, 28.7.

3-(3-Pyridyl)-1-(3-(tert-butoxycarbonylmethoxy)phenyl)-propan-1-one (19)

A mixture of 17 (1.70 g, 5.0 mmol) and 10% Pd/C (85 mg) in EtOAc (70 mL) was hydrogenated in a Parr under H$_2$ at 42 psi for 15 h. The mixture was filtered through Celite and the filtrate was concentrated in vacuo. Chromatography on silica (50–60% EtOAc/hexanes) gave 1.70 g (100%) of a colorless oil. $^1$H NMR (CDCl$_3$, 300 MHz) 8.54 (d, J=2.0 Hz, 1 H), 8.48 (dd, J=4.8, 1.5 Hz, 1 H), 7.70–7.10 (m, 6 H) 4.58 (s, 2 H), 3.31 (t, J=7.3 Hz, 2 H), 3.09 (t, J=7.4 Hz, 2 H), 1.50 (s, 9 H); $^{13}$C NMR (CDCl$_3$, 75 MHz) 198.3, 168.0, 158.6, 150.4, 148.1, 138.4, 136.9, 136.4, 130.2, 123.7, 121.8, 120.7, 113.5, 83.0, 66.1, 40.2, 28.4, 27.5.

1-(3-(tert-Butoxycarbonylmethoxy)phenyl)-3-(3-indoyl)propan-1-one (20)

Prepared in a similar manner as (19) from 1-(3-(tert-Butoxycarbonylmethoxy)phenyl)-3-(3-indoyl)-2-propen-1-one (18). Flash chromatography (silica gel, 20%→30% EtOAc/hexanes) afforded 468 mg (80%) of a white solid: IR (neat) 1735, 1680, 1230, 1150 cm$^{-1}$; $^1$H NMR (MeOH, 300 MHz) 7.60–7.55 (m, 2 H), 7.43–7.32 (m, 3H), 7.16–6.99 (m, 4H), 4.57 (s, 2H), 3.39–3.32 (obs t, 2H), 3.16 (t, J=7.2 Hz, 2H), 1.47 (s, 9H); $^{13}$C NMR (MeOH, 75 MHz) 202.5, 170.4, 160.0, 140.2, 138.6, 131.3, 129.0, 123.5, 122.9, 122.7, 121.5, 120.0, 119.7, 115.6, 114.6, 112.6, 84.0, 67.1, 41.0, 28.7, 21.6.

(1R)-3-(3-Pyridyl)-1-(3-(tert-butoxycarbonylmethoxy)phenyl)-propan-1-ol (21)

To a solution of 19 (1.70 g, 4.98 mmol) in THF (10 mL) at −23° C. under N$_2$ was added a cold (−23° C.) solution of (+)-B-chlorodiisopinocamphenylborane (3.2 g, 9.97 mmol) in THF (20 mL). The mixture was placed in a freezer for 3 days. Then, the mixture was concentrated in vacuo and the residue was redissolved in diethyl ether (100 mL). The ether solution was treated with diethanolamine (1.44 mL, 15.0 mmol) with vigorous stirring at room temperature for 3 h. The white precipitates were filtered off and the filtrate was concentrated in vacuo. Chromatography on silica (50–100% EtOAc/hexanes) provided 1.41 g (82%) of a colorless oil (97.5% ee by Chiracel HPLC, 25% i-PrOH/hexanes, retention time 78.5 min for the R-enantiomer and 52.1 min for the S-enantiomer). $^1$H NMR (CDCl$_3$, 300 MHz) 8.42 (m, 2 H), 7.55–6.80 (m, 6 H), 4.65 (dd, J=7.8, 5.1 Hz,1 H), 4.52 (s, 2 H), 2.75 (m, 2 H), 2.05 (m, 2 H), 1.49 (s, 9 H); $^{13}$C NMR (CDCl$_3$, 75 MHz) 175.1, 168.4, 158.6, 150.3, 147.7, 146.8, 137.5, 136.3, 130.0, 123.7, 119.4, 114.1, 112.5, 108.0, 82.8, 73.5, 66.0, 40.5, 29.5, 28.4.

(R) 1-(3-(tert-Butoxycarbonylmethoxy)phenyl)-3-(3-indoyl)propan-1-ol (22)

Prepared in a similar manner as (21) from 1-(3-(tert-Butoxycarbonylmethoxy)phenyl)-3-(3-indoyl)propan-1-one (20). Flash chromatography (silica gel, 20%→30% EtOAc/hexanes) afforded 258 mg (55%) of yellowish oil (+95% ee by Chiracel HPLC, 20% i-PrOH/hexanes, retention time 54.2 min for the R-enantiomer and 50.7 min for the S-enantiomer): IR (neat) 3410, 2930, 1735, 1455, 1230, 1150, 1080 cm$^{-1}$; $^1$H NMR (MeOH, 300 MHz) 7.51 (d, J=7.8 Hz, 1 H), 7.33 (d, J=8.1, 1H), 7.25 (app t, J=7.9, 1H), 7.11–6.92 (m, 5H), 6.82–6.78 (m, 1H), 4.67 (t, J=5.8 Hz, 1H), 4.54 (s, 2H), 2.85–2.77 (m, 2H), 2.18–2.06 (m, 2H), 1.47 (s, 9H); $^{13}$C NMR (MeOH, 75 MHz) 170.8, 159.9, 148.9, 138.6, 130.8, 129.2, 123.2, 122.6, 120.8, 119.9, 116.4, 114.9, 113.7, 112.6, 83.8, 75.0, 67.0, 41.3, 28.7, 22.9.

Preparation of Functionalized Monomers (1R)-3-Phenyl-1-[3-((3-aminopropyl)oxy)phenyl]-1-propyl (2S)-1-(3,3-dimethyl-1,2-dioxopentyl)-2-piperidinecarboxylate trifluroacetic acid salt (24)

A solution of alcohol 2 (385 mg, 1.0 mmol) in CH$_2$Cl$_2$ (3 mL) was treated with (2S)-1-(1,2-dioxo-3,3-dimethylpentyl)-2-piperidinecarboxylic acid (23, 255 mg, 1.0 mmol, prepared from L-pipercolic acid in 4 steps following literature procedures by Holt et al. *J. Amer. Chem. Soc.*, 1993, 115, 9925–9938), followed by 1,3-dicyclohexylcarbodiimide (DCC, 247 mg, 1.2 mmol), and 4-(dimethylamino)-pyridine (DMAP, 85 mg, 0.70 mmol) under a nitrogen atmosphere. The resulting bright yellow suspension was allowed to stir overnight. The mixture was then filtered through glass wool and chromatographed (silica gel, 20% EtOAc/hexanes) to give (1R)-3-Phenyl-1-[3-9(3-tert-butyloxycarbamylpropyl)oxy)phenyl]-1-propyl (2S)-1-(3,3-dimethyl-1,2-dioxopentyl)-2-piperidinecarboxylate (524 mg, 84%) as a colorless oil: $^1$H NMR (CDCl$_3$, 300 MHz) (single diastereomer, mixture of rotamers) 7.35–6.90 (m, 9 H), 5.80 (t, J=5.9 Hz, 1 H), 5.32 (d, J=5.0 Hz, 0.82 H, pipercolate α-H of rotamer A), 4.80 (br. s, 1 H), 4.02 (t, J=6.1 Hz, 2 H), 3.40–3.25 (m, 3 H), 3.12 (td, J=13.0, 3.3 Hz, 1 H), 2.60 (m, 2 H), 2.35 (d, J=14 Hz, 1 H), 2.28 (m, 1 H), 2.07 (m, 1 H), 1.96 (t, J=6.3 Hz, 2 H), 1.80–1.60 (m, 5 H), 1.43 (s, 9 H), 1.22 (s, 3 H), 1.20 (s, 3 H), 0.88 (t, J=7.4 Hz, 3 H); $^{13}$C NMR (CDCl$_3$, 75 MHz) (single diastereomer, mixture of rotamers) 208.2, 170.1, 167.6, 159.4, 156.4, 141.7, 141.3, 130.1, 128.9, 128.7, 126.5, 119.4, 114.7, 113.2, 113.0, 66.1, 57.1, 51.7, 47.1, 44.5, 38.3, 32.9, 32.1, 30.0, 28.8, 26.8, 25.4, 24.9, 24.0, 23.8, 23.5, 21.6, 9.1. MS(FAB): (M+Na)$^+$ 645, (M+H)$^+$ 623.

A solution of the above compound (200 mg, 0.32 mmol) in $CH_2Cl_2$ (5.0 mL) was treated with trifluoroacetic acid (1.0 mL) and the mixture was stirred at room temperature for 1 h. The reaction mixture was diluted with toluene (150 mL) and concentrated in vacuo to give 24 (203 mg, 100%) as a colorless gum: $^1$H NMR (CDCl$_3$, 300 MHz) (single diastereomer, mixture of rotamers) 7.90 (br. s, 3 H), 7.30–6.70 (m, 9 H), 5.70 (t, J=5.4 Hz, 1 H), 5.23 (d, J=4.8 Hz, 1 H), 4.01 (m, 2 H), 3.30 (d, J=12.8 Hz, 1 H), 3.13 (m, 3 H), 2.58 (m, 2 H), 2.40–2.00 (m, 4 H), 1.75–1.50 (m, 5 H), 1.35 (m, 2 H), 1.13 (s, 3 H), 1.12 (s, 3 H), 0.80 (t, J=7.4 Hz, 3 H); $^{13}$C NMR (CDCl$_3$, 75 MHz) (single diastereomer, mixture of rotamers) 208.4, 175.3, 175.2, 170.1, 167.8, 158.8, 142.0, 141.2, 130.2, 128.9, 128.7, 126.5, 119.8, 114.6, 113.0, 108.0, 66.1, 51.8, 47.1, 44.6, 38.6, 38.3, 32.8, 32.1, 27.3, 26.8, 25.3, 23.8, 23.4, 21.5, 9.0. HRMS(FAB): (M+Na)$^+$ calcd: 523.3172 found: 523.3162.

(1R)-3-Phenyl-1-(3-(hydroxycarbonylmethoxy)phenyl)-1-propyl (2S)-1-(3,3-dimethyl-1,2-dioxopentyl)-2-piperidinecarboxylate (25)

A solution of alcohol 3 (342 mg, 1.0 mmol) in $CH_2Cl_2$ (3 mL) was treated with (2S)-1-(1,2-dioxo-3,3-dimethylpentyl)-2-piperidinecarboxylic acid (23, 255 mg, 1.0 mmol, prepared from L-pipecolic acid in 4 steps following literature procedures by Holt et al. *J. Amer. Chem. Soc.*, 1993, 115, 9925–9938), followed by 1,3-dicyclohexylcarbodiimide (DCC, 247 mg, 1.2 mmol), and 4-(dimethylamino)-pyridine (DMAP, 85 mg, 0.70 mmol) under a nitrogen atmosphere. The resulting bright yellow suspension was allowed to stir overnight. The mixture was then filtered through glass wool and chromatographed (silica gel, 20% EtOAc/hexanes) to give (1R)-3-Phenyl-1-(3-(tert-butoxycarbonylmethoxy)phenyl]-1-propyl (2S)-1-(3,3-dimethyl-1,2-dioxopentyl)-2-piperidinecarboxylate (470 mg, 82%) as a colorless oil: $^1$H NMR (CDCl$_3$, 300 MHz) (single diastereomer, mixture of rotamers) 7.50–6.90 (m, 9 H), 5.93 (t, J=6.0 Hz, 1 H), 5.46 (d, J=3.4 Hz, 0.83 H, pipercolate α-H of rotamer A), 4.67 (s, 2 H), 3.50 (d, J=12.9 Hz, 1 H), 3.32 (td, J=12.5, 3.0 Hz, 1 H), 2.75 (m, 2 H), 2.53 (d, J=13.6 Hz, 1 H), 2.41 (m, 1 H), 2.22 (m, 1 H), 2.97–2.71 (m, 6 H), 1.62 (s, 9 H), 1.38 (s, 3 H), 1.35 (s, 3 H), 1.03 (t, J=7.4 Hz); $^{13}$C NMR (CDCl$_3$, 75 MHz) (single diastereomer, mixture of rotamers) 208.3, 175.0, 170.0, 168.0, 167.5, 158.5, 141.7, 141.2, 130.2, 128.9, 128.7, 126.5, 120.2, 114.7, 113.6, 82.8, 66.1, 51.6, 47.1, 44.5, 38.2, 32.9, 32.0, 28.4, 26.8, 25.3, 24.0, 23.4, 21.6, 9.2. HRMS (FAB): (M+Na)$^+$ calcd: 602.3094, found: 602.3090.

A solution of the above tert-butyl ester (200 mg, 0.34 mmol) in $CH_2Cl_2$ (5.0 mL) was treated with trifluoroacetic acid (1.0 mL) and the mixture was stirred at room temperature for 1 h. The reaction mixture was diluted with toluene (150 mL) and concentrated in vacuo to give 25 (177 mg, 99%) as a colorless gum: $^1$H NMR (CDCl$_3$, 300 MHz) (single diastereomer, mixture of rotamers) 7.30–6.80 (m, 9 H), 5.75 (m, 1 H), 5.30 (d, J=4.8 Hz, 1 H), 4.66 (s, 2 H), 3.35 (d, J=9.27 Hz, 1 H), 3.19 (td, J=12.4, 2.9 Hz, 1 H), 2.69 (m, 2 H), 2.39 (d, J=16.2 Hz, 1 H), 2.30 (m, 1 H), 2.10 (m, 1 H), 1.90–1.60 (m, 6 H), 1.50 (m, 1 H), 1.19 (s, 3 H), 1.17 (s, 3 H), 0.85 (t, J=7.4 Hz, 3 H); $^{13}$C NMR (CDCl$_3$, 75 MHz) (single diastereomer, mixture of rotamers) 208.0, 172.3, 169.8, 167.9, 158.2, 142.2, 141.1, 130.2, 128.9, 128.7, 126.5, 120.3, 115.5, 111.8, 65.5, 57.2, 52.0, 47.2, 44.6, 38.3, 33.0, 32.9, 32.1, 27.0, 25.3, 25.2, 23.9, 23.4, 21.5, 9.1. HRMS(FAB): (M+Na)$^+$ calcd: 546.2468, found: 546.2461.

(1R)-3-(3,4-Dimethoxyphenyl)-1-[3-(hydroxycarbonylmethoxy)phenyl]-1-propyl (2S)-1-(3,3-dimethyl-1,2-dioxopentyl)-2-piperidinecarboxylate (26)

A solution of (R) 1-(3-(tert-Butoxycarbonylmethoxy) phenyl)-3-(3,4-dimethoxyphenyl) propan-1-ol (13) (805 mg, 2.0 mmol) in $CH_2Cl_2$ (4 mL) at 0° C. was treated with (2S)-1-(1,2-dioxo-3,3-dimethylpentyl)-2-piperidinecarboxylic acid (23, 511 mg, 2.0 mmol, prepared from L-pipecolic acid in 4 steps following literature procedures by Holt et al. *J. Amer. Chem. Soc.*, 1993, 115, 9925–9938) followed by 4-(dimethylamino)pyridine (DMAP 1 mg) and 1,3-dicyclohexyl carbodiimide (DCC, 413 mg, 2 mmol) under a nitrogen atmosphere. The resulting bright yellow suspension was allowed to stir for 2 h then diluted with diethyl ether (20 mL). The reaction mixture was then filtered, evaporated, and flash chromatographed (silica gel, 25%→30% EtOAc/hexanes) to afford 993 mg (78%) of a clear colorless viscous oil: IR (neat) 2940, 1735, 1645, 1515, 1455, 1225, 1150 cm$^{-1}$; $^1$H NMR (CDCl$_3$, 300 MHz) 7.20–7.17 (m, 2H), 6.91–6.69 (m, 5H), 5.73–5.68 (m, 1H). 5.24 (br s, 1H), 4.46 (s, 2H), 3.79 (s, 3H), 3.78 (s, 3H), 3.29 (br d, J=13.2 Hz, 1H), 3.07 (td, J=12.7, 3.0 Hz, 1H), 2.52–2.44 (m, 2H), 2.29 (br d, J=13.6 Hz, 1H), 2.20–2.13 (m, 1H), 2.04–1.95 (m, 1H), 1.71–1.51 (m, 7H), 1.41 (s, 9H), 1.16, (s, 3H), 1.14 (s, 3H), 0.82 (t, J=7.4 Hz, 3H); $^{13}$C NMR (CDCl$_3$, 75 MHz) 208.2, 168.3, 167.6, 158.5, 149.3, 147.8, 141.8, 133.9, 130.1, 120.5, 120.3, 114.7, 113.7, 112.2, 111.7, 82.7, 66.2, 56.2, 51.7, 47.1, 44.6, 38.3, 32.9, 31.6, 28.8, 26.8, 25.3, 23.8, 23.5, 21.6, 9.1. HRMS(FAB): (M+Na)$^+$ calcd: 662.3305, found 662.3301.

A solution of the above tert-butyl ester (460 mg, 0.72 mmol) in $CH_2Cl_2$ (5.0 mL) was treated with trifluoroacetic acid (1.0 mL) and the mixture was stirred at room temperature for 1 h. The reaction mixture was diluted with toluene (150 mL) and concentrated in vacuo to give 26 (420 mg, 100%) as a yellowish foam: $^1$H NMR (CDCl$_3$, 300 MHz) (single diastereomer, mixture of rotamers) 8.00 (br. s, 1 H), 7.35–6.70 (m, 7H), 5.82 (m, 1 H), 5.33 (d, J=4.5 Hz, 1 H), 4.71 (m, 2 H), 3.89 (s, 3 H), 3.87 (s, 3 H), 3.38 (d, J=12.6 Hz, 1 H), 3.24 (td, J=12.3, 2.7 Hz, 1 H), 2.60 (m, 2 H), 2.45–2.05 (m, 3 H), 1.70 (m, 6 H), 1.45 (m, 2 H), 1.23 (s, 3 H), 1.21 (s, 3H), 0.89 (t, J=7.4 Hz, 3 H); $^{13}$C NMR (CDCl$_3$, 75 MHz) (single diastereomer, mixture of rotamers) 208.0, 172.0, 169.8, 167.8, 158.2, 149.4, 147.8, 142.2, 133.7, 130.2, 129.4, 128.6, 125.7, 120.6, 120.3, 115.5, 112.2, 111.8, 111.7, 108.2, 65.5, 56.3, 51.9, 47.2, 44.6, 38.5, 32.9, 31.7, 28.4, 27.0, 25.3, 23.9, 23.4, 21.8, 21.5, 9.1. HRMS(FAB): (M+Na)$^+$ calcd: 606.2679, found: 606.2692.

(1R)-3-(3,4,5-Trimethoxyphenyl)-1-[3-(hydroxycarbonylmethoxy)phenyl]-1-propyl (2S)-1-(3,3-dimethyl-1,2-dioxopentyl)-2-piperidinecarboxylate (27)

A solution of alcohol 14 (650 mg, 1.5 mmol) in $CH_2Cl_2$ (5 mL) was treated with (2S)-1-(1,2-dioxo-3,3-dimethylpentyl)-2-piperidinecarboxylic acid (23, 382 mg, 1.5 mmol, followed by 1,3-dicyclohexylcarbodiimide (370 mg, 1.8 mmol), and 4-(dimethylamino)-pyridine (128 mg, 1.0 mmol) under a nitrogen atmosphere. The resulting bright yellow suspension was allowed to stir overnight. The mixture was then filtered through glass wool and chromatographed (silica gel, 20–30% EtOAc/hexanes) to give (1R)-3-(3,4,5-trimethoxyphenyl)-1-[3-(tert-butoxycarbonylmethoxy)phenyl]-1-propyl (2S)-1-(3,3-dimethyl-1,2-dioxopentyl)-2-piperidinecarboxylate (776 mg, 78%) as a colorless oil: $^1$H NMR (CDCl$_3$, 300 MHz) (single diastereomer, mixture of rotamers) 7.30–6.80 (m, 4

H), 6.37 (s, 2 H), 5.82 (t, J=6.1 Hz, 1 H), 5.33 (d, J=5.2 Hz, 1 H), 4.54 (s, 2 H), 3.85 (s, 6 H), 3.83 (s, 3 H), 3.38 (d, J=12.6 Hz, 1 H), 3.16 (td, J=12.8, 3.1 Hz, 1 H), 2.60 (m, 2 H), 2.45–2.05 (m, 3 H), 1.70 (m, 6 H), 1.50 (s, 9 H), 1.45 (m, 2 H), 1.25 (s, 3 H), 1.23 (s, 3 H), 0.90 (t, J=7.4 Hz, 3 H); $^{13}$C NMR (CDCl$_3$, 75 MHz) (single diastereomer, mixture of rotamers) 208.2, 175.1, 170.1, 168.2, 167.6, 158.5, 153.6, 141.7, 137.0, 130.1, 120.9, 120.2, 114.6, 113.7, 105.7, 82.7, 66.2, 61.2, 56.5, 51.7, 47.1, 44.6, 38.2, 32.9, 32.4, 28.4, 26.8, 25.3, 23.9, 23.5, 21.6, 9.1.

A solution of the above tert-butyl ester (400 mg, 0.60 mmol) in CH$_2$Cl$_2$ (5.0 mL) was treated with trifluoroacetic acid (1.0 mL) and the mixture was stirred at room temperature for 1 h. The reaction mixture was diluted with toluene (150 mL) and concentrated in vacuo to give 27 (358 mg, 98%) as a white foam: $^1$H NMR (CDCl$_3$, 300 MHz) (single diastereomer, mixture of rotamers) 7.30–6.80 (m, 4 H), 6.39 (s, 2 H), 5.82 (m, 1 H), 5.33 (d, J=4.6 Hz, 1 H), 4.70 (m, 2 H), 3.86 (s, 6 H), 3.84 (s, 3 H), 3.38 (d, J=12.6 Hz, 1 H), 3.22 (td, J=12.8, 3.1 Hz, 1 H), 2.60 (m, 2 H), 2.45–2.05 (m, 3 H), 1.70 (m, 6 H), 1.45 (m, 2 H), 1.23 (s, 3 H), 1.21 (s, 3 H), 0.89 (t, J=7.4 Hz, 3 H); $^{13}$C NMR (CDCl$_3$, 75 MHz) (single diastereomer, mixture of rotamers) 208.0, 175.0, 171.7, 169.8, 167.8, 158.2, 153.6, 142.1, 136.9, 130.2, 129.4, 128.6, 125.7, 120.3, 115.5, 111.8, 107.9, 105.8, 65.6, 61.2, 56.5, 52.0, 47.2, 44.6, 38.3, 32.9, 32.5, 27.0, 25.3, 23.8, 23.4, 21.5, 9.1. MS(FAB): (M+Na)$^+$ calcd: 636.2785, found: 636.2756.

(R) 1-(3-(Hydroxycarbonylmethoxy)phenyl)-3-(3,4-methylendioxyphenyl)-1-propyl (2S)-1-(3,3'-dimethyl-1,2-dioxopentyl)-2-piperdinecarboxylate (28)

A solution of (R) 1-(3-(tert-Butoxycarbonylmethoxy) phenyl)-3-(3,4-methylenedioxyphenyl) propan-1-ol (15) (500 mg, 1.29 mmol) in CH$_2$Cl$_2$ (4 mL) at 0° C. was treated with (2S)-1-(1,2-dioxo-3,3-dimethylpentyl)-2-piperidinecarboxylic acid (23, 330 mg, 1.29 mmol, prepared from L-pipecolic acid in 4 steps following literature procedures by Holt et al. *J. Amer. Chem. Soc.*, 1993, 115, 9925–9938) followed by 4-(dimethylamino)pyridine (DMAP 1 mg) and 1,3-dicyclohexyl carbodiimide (DCC, 267 mg, 1.29 mmol) under a nitrogen atmosphere. The resulting bright yellow suspension was allowed to stir for 2 h then diluted with diethyl ether (20 mL). The reaction mixture was filtered, evaporated, and flash chromatographed. Flash chromatography (silica gel, 20%→30%% EtOAc/hexanes) of crude material afforded 556 mg (69%) of a clear colorless oil: IR (neat) 2970, 1745, 1700, 1640, 1490, 1440, 1245, 1150 cm$^{-1}$ ; $^1$H NMR (CDCl$_3$, 300 MHz) (single diastereomer, mixture of rotamers) 7.32–7.26 (m, 1H), 6.99–6.84 (m, 6H), 5.93 (s, 2H). 5.80–76 (m, 1H), 5.33 (d, J=4.9 Hz, 1H), 4.55 (s, 2H), 3.38 (br d, J=12.9 Hz, 1H), 3.16 (td, J=12.3, 3.1 Hz, 1H), 2.63–2.50 (m, 2H), 2.38 (br d, J=13.7 Hz, 1H), 13.7 Hz, 1H), 2.26–2.16 (m, 1H), 2.09–2.04 (m, 1H), 1.81–1.57 (m, 7H), 1.51 (s, 9H), 1.26, (s, 3H), 1.23 (s, 3H), 0.91(t, J=7.4 Hz, 3H); $^{13}$C NMR (CDCl$_3$, 75 MHz) (single diastereomer, mixture of rotamers) 208.2, 170.0, 168.3, 167.6, 158.5, 148.1, 146.2, 141.7, 135.0, 130.1, 121.5, 120.2, 114.9, 113.6, 109.2, 108.6, 101.2, 82.7, 66.2, 51.7, 47.1, 44.5, 38.3, 32.9, 31.6, 28.4, 26.8, 25.3, 23.8, 23.5, 21.6, 9.1. HRMS(FAB): (M+Na)$^+$ calcd: 646.2992, found 646.3021.

A solution of the above tert-butyl ester (625 mg, 1.00 mmol) in CH$_2$Cl$_2$ (4.0 mL) was treated with trifluoroacetic acid (1.5 mL) and the mixture was stirred at room temperature for 1 h. The reaction mixture was diluted with toluene (150 mL) and concentrated in vacuo to give 28 (483 mg, 85%) as a clear colorless oil: IR (neat) 3420, 2940, 1735, 1700, 1640, 1490, 1440, 1245, 1040 cm$^{-1}$; $^1$H NMR (CDCl$_3$, 300 MHz) (single diastereomer, mixture of rotamers) 7.12 (t, J=6.7 Hz, 1H), 6.92–6.81 (m, 3H), 6.68–6.52 (m, 3H), 5.86 (s, 2H), 5.73 (t, J=7.2 Hz, 1H), 5.33 (s, 1H), 4.40 (s, 2H), 3.34 (d, J=12.2 Hz, 1H), 3.19 (t, J=12.0 Hz, 1H), 2.54–2.46 (m, 2H), 2.34 (d, J=12.6 Hz, 1H), 2.24–2.00 (m, 2H), 1.73–1.32 (m, 7H), 1.18 (s, 3H), 1.16 (s, 3H), 0.84 (t, J=7.3 Hz, 3H); $^{13}$C NMR (CDCl$_3$, 75 MHz) (single diastereomer, mixture of rotamers) 208.0, 169.9, 167.79, 158.3, 148.0, 146.2, 141.9, 135.0, 130.1, 121.5, 109.1, 108.6, 107.2, 101.2, 77.0, 51.9, 47.0, 44.6, 38.6, 32.9, 31.8, 26.9, 25.3, 23.9, 23.3, 21.6, 9.1.

(1R)-3-(3-Pyridyl)-1-(3-(hydroxycarbonylmethoxy) phenyl)-1-propyl (2S)-1-(3,3-dimethyl-1,2-dioxopentyl)-2-piperidinecarboxylate (29)

A solution of alcohol 21 (530 mg, 1.54 mmol) in CH$_2$Cl$_2$ (5 mL) was treated with (2S)-1-(1,2-dioxo-3,3-dimethylpentyl)-2-piperidinecarboxylic acid (23, 393 mg, 1.54 mmol, followed by 1,3-dicyclohexylcarbodiimide (381 mg, 1.85 mmol), and 4-(dimethylamino)-pyridine (132 mg, 1.08 mmol) under a nitrogen atmosphere. The resulting bright yellow suspension was allowed to stir overnight. The mixture was then filtered through glass wool and chromatographed (silica gel, 20–60% EtOAc/hexanes) to give (1R)-3-(3-Pyridyl)-1-[3-(tert-butoxycarbonylmethoxy)phenyl]-1-propyl (2S)-1-(3,3-dimethyl-1,2-dioxopentyl)-2-piperidinecarboxylate (860 mg, 96%) as a colorless oil: $^1$H NMR (CDCl$_3$, 300 MHz) (single diastereomer, mixture of rotamers) 8.46 (m, 2 H), 7.50–6.80 (m, 6 H), 5.80 (t, J=6.1 Hz, 1 H), 5.32 (d, J=5.0 Hz, 1 H), 4.54 (s, 2 H), 3.38 (d, J=12.8 Hz, 1 H), 3.14 (td, J=12.6, 3.0 Hz, 1 H) 2.60 (m, 2 H), 2.36 (d, J=13.7 Hz, 1 H), 2.25 (m, 1 H), 2.10 (m, 1 H), 1.75 (m, 4 H), 1.49 (s, 9 H), 1.45 (m, 2 H), 1.24 (s, 3 H), 1.22 (s, 3 H), 0.90 (t, J=7.4 Hz, 3 H); $^{13}$C NMR (CDCl$_3$, 75 MHz) (single diastereomer, mixture of rotamers) 208.2, 175.1, 170.0, 168.2, 167.7, 158.6, 150.2, 148.1, 141.3, 136.6, 130.2, 123.8, 120.1, 115.0, 113.6, 107.9, 82.8, 66.1, 51.7, 47.1, 44.6, 39.2, 37.8, 34.4, 33.0, 29.2, 28.4, 26.7, 25.3, 23.9, 23.5, 21.6, 21.4, 9.1.

A solution of the above tert-butyl ester (400 mg, 0.69 mmol) in CH$_2$Cl$_2$ (5.0 mL) was treated with trifluoroacetic acid (1.0 mL) and the mixture was stirred at room temperature for 1 h. The reaction mixture was diluted with toluene (150 mL) and concentrated in vacuo to give 29 (424 mg, 96%, trifluoroacetic acid salt) as a white foam: $^1$H NMR (CDCl$_3$, 300 MHz) (single diastereomer, mixture of rotamers) 8.75 (s, 1 H), 8.67 (d, J=10.4 Hz, 1 H), 8.23 (t, J=5.6 Hz, 1 H), 7.79 (dd, J=7.9, 5.6 Hz, 1 H), 7.35–6.75 (m, 4 H), 5.80 (t, J=6.1 Hz, 1 H), 5.25 (d, J=5.0 Hz, 1 H), 4.75 (m, 2 H), 3.35 (d, J=13.2 Hz, 1 H), 3.14 (td, J=12.6, 3.0 Hz, 1 H) 2.75 (m, 2 H), 2.30 (m, 3 H), 1.70 (m, 6 H), 1.40 (m, 2 H), 1.22 (s, 6 H), 0.92 (t, J=7.4 Hz, 3 H); $^{13}$C NMR (CDCl$_3$, 75 MHz) (single diastereo-mer, mixture of rotamers) 208.3, 172.3, 169.9, 167.8, 158.6, 145.5, 142.5, 142.0, 139.8, 139.5, 130.6, 129.4, 128.6, 120.2, 117.1, 111.8, 65.2, 51.8, 47.1, 44.8, 36.7, 32.8, 28.4, 26.6, 25.2, 23.7, 21.4, 9.1. HRMS(FAB): (M+Na)$^+$ calcd: 547.2420, found: 547.2415.

(1R)-3-(3-Indolyl)-1-(3-(hydroxycarbonylmethoxy) phenyl)-1-propyl (2S)-1-(3,3-dimethyl-1,2-dioxopentyl)-2-piperidinecarboxylate (30)

The tert-butyl ester was prepared in a similar manner as the ester of 28 from (R) 1-(3-(tert-Butoxycarbonylmethoxy) phenyl)-3-(3-indoyl)propan-1-ol (22). Flash chromatography (silica gel, 30% EtOAc/hexanes) afforded 492 mg (76%) of clear colorless oil: IR (neat) 3410, 2970, 1735, 1700, 1635, 1455, 1225, 1150 cm$^{-1}$; $^1$H NMR (CDCl$_3$, 300

MHz) 8.04 (br s, 1H), 7.53 (d, J=7.8 Hz, 1 H), 7.37 (d, J=8.0 Hz, 1H), 7.30–7.11 (m, 3H), 7.01–6.84 (m, 4H), 5.91–5.86 (m, 1H), 5.35 (d, J=4.8 Hz, 1H), 4.54 (s, 2H), 3.39 (d, J=13.3 Hz, 1H), 3.18 (td, J=12.6, 3.0 Hz, 1H), 2.87–2.74 (m, 2H), 2.41–2.18 (m, 3H), 1.82–1.57 (m, 7H), 1.50 (s, 9H), 1.27 (s, 3H), 1.24 (s, 3H), 0.92 (t, J=7.4 Hz, 3H); $^{13}$C NMR (CDCl$_3$, 75 MHz) 208.3, 170.1, 168.3, 167.7, 158.5, 141.9, 136.8, 130.1, 127.7, 122.3, 121.8, 120.3, 119.6, 119.1, 115.4, 114.7, 113.7, 111.5, 82.7, 66.2, 51.7, 47.1, 44.5, 36.8, 32.9, 28.4, 26.9, 25.4, 24.0, 23.4, 21.6, 9.1. HRMS(FAB): (M+Na)$^+$ calcd: 641.3203, found: 641.3193.

A solution of the above tert-butyl ester (112 mg, 0.18 mmol) in CH$_2$C12 (5.0 mL) was treated with trifluoroacetic acid (1.0 mL) and the mixture was stirred at room temperature for 1 h. The reaction mixture was diluted with toluene (150 mL) and concentrated in vacuo to give 30 (102 mg, 100%) as a brown foam: $^1$H NMR (CDCl$_3$, 300 MHz) (single diastereomer, mixture of rotamers) 7.90–6.70 (m, 10 H), 5.85 (m, 1 H), 5.35 (m, 1 H), 4.62 (mn, 2 H), 3.40 (m, 1 H), 3.25 (mn, 1 H), 2.80 (mn, 2 H), 2.40–2.05 (m, 3 H), 1.85–1.45 (mn, 12 H), 1.23 (s, 3 H), 1.21 (s, 3 H), 0.88 (t, J=7.4 Hz, 3 H); $^{13}$C NMR (CDCl$_3$, 75 MHz) (single diastereomer, mixture of rotamers) 208.0, 175.0, 169.8, 167.9, 158.2, 142.3, 130.2, 129.4, 128.6, 125.7, 122.5, 119.7, 119.1, 115.3, 111.6, 108.0, 65.5, 52.0, 47.2, 44.6, 32.9, 27.0, 25.3, 23.9, 23.4, 21.6, 9.1. HRMS(FAB): (M+Na)$^+$ calcd: 585.2577, found: 585.2561.

PREPARATION OF DIMERIZERS

EXAMPLE 1

N,N'-Bis[3-(3-((1R)-1-((2S)-(3,3-dimethyl-1,2-dioxopentyl)piperidine-2-carbonyloxo)-3-phenyl) propylphenoxy)propyl] 1,4-phenylenediacetamide (31)

A mixture of 1,4-phenylenediacetic acid (194 mg, 1.0 mmol) and disuccinimidyl carbonate (512 mg, 2.0 mg) in anhydrous acetonitrile (5.0 mL) was treated with pyridine (243 μL, 3.0 mmol). The mixture was stirred at room temperature under nitrogen overnight. The resulting suspension was partitioned between EtOAc (70 mL) and water (50 mL). The organic layer was separated, washed with 1 M Na$_2$CO$_3$, water, 0.5 N HCl, saturated brine, dried (Na$_2$SO$_4$), and concentrated in vacuo to give disuccinimidyl 1,4-phenylenediacetate (144 mg, 37%) as a white solid. $^1$H NMR (DMSO-d$_6$, 300 MHz) 7.34 (s, 4 H), 4.10 (s, 4 H), 2.80 (s, 8 H).

A solution of 24 (102 mg, 0.16 mmol) in CH$_2$Cl$_2$ (2.0 mL) was treated with the above activated diester (31 mg, 0.080 mmol) and Et$_3$N (67 μL, 0.48 mmol). The mixture was stirred at room temperature overnight. The resulting clear solution was impregnated on silica gel and evaporated to dryness. Chromatography (silica gel, 50–100% EtOAc/hexanes) provided 31 (60 mg, 62%) as a white solid: mp 55–57° C.; $^1$H NMR (CDCl$_3$, 300 MHz) (single diastereomer, mixture of rotamers) 7.32–7.15 (m, 16 H), 6.95 (d, J=7.7 Hz, 2 H), 6.83 (s, 2 H), 6.74 (m, 2 H), 6.01 (br. s, 2 H), 5.80 (t, J=5.8 Hz, 2 H), 5.32 (d, J=4.9 Hz, 2 H), 3.98 (t, J=5.7 Hz, 4 H), 3.52 (s, 4 H), 3.50–3.30 (m, 6 H), 3.22 (td, J=12.4, 2.6 Hz, 2 H), 2.67 (m, 4 H), 2.38 (d, J=13.6 Hz, 2 H), 2.30 (m, 2 H), 2.12 (m, 2 H), 1.95 (t, J=6.1 Hz, 4 H), 1.85–1.60 (m, 10 H), 1.50 (m, 4 H), 1.23 (s, 6 H), 1.21 (s, 6 H), 0.89 (t, J=7.4 Hz, 6 H); $^{13}$C NMR (CDCl$_3$, 75 MHz) (single diastereomer, mixture of rotamers) 208.2, 208.0, 171.3, 170.1, 169.9, 167.8, 159.2, 141.8, 141.6, 141.2, 134.4, 130.3, 130.1, 128.9, 128.7, 126.5, 119.3, 115.0, 114.7, 113.1, 112.8, 57.1, 51.7, 47.1, 44.5, 43.7, 39.3, 38.3, 38.2, 37.8, 33.0, 32.8, 32.1, 29.3, 26.9, 25.3, 23.9, 23.5, 21.6, 21.4, 9.17, 9.13. MS(FAB): (M+Na)$^+$ 1225, (M+H)$^+$ 1203.

EXAMPLE 2

N,N'-Bis[3-(3-((1R)-1-((2S)-(3,3-dimethyl-1,2-dioxopentyl)piperidine-2-carbonyloxo)-3-phenyl) propylphenoxy)propyl] suberamide (32)

Following the same procedure as in Example 1 except replacing suberic acid for 1,4-phenylenediacetic acid, obtained 32 (54 mg, 56%) as a white solid. mp 44–46° C.; $^1$H NMR (CDCl$_3$, 300 MHz) (single diastereomer, mixture of rotamers) 7.35–6.85 (m, 18 H), 6.18 (br. s, 2 H), 5.86 (t, J=5.9 Hz, 2 H), 5.39 (d, J=4.9 Hz, 2 H), 4.12 (t, J=5.9 Hz, 4 H), 3.60–3.40 (m, 6 H), 3.28 (td, J=12.6, 2.8 Hz, 2 H), 2.70 (m, 4 H), 2.47 (d, J=13.8 Hz, 2 H), 2.35 (m, 2 H), 2.30–2.00 (m, 12 H), 1.95–1.70 (m, 14 H), 1.55–1.35 (m, 6 H), 1.30 (s, 6 H), 1.28 (s, 6 H), 0.96 (t, J=7.5 Hz, 6 H); $^{13}$C NMR (CDCl$_3$, 75 MHz) (single diastereomer, mixture of rotamers) 208.3, 170.0, 167.8, 159.3, 141.8, 141.2, 130.2, 128.9, 128.7, 126.5, 119.4, 114.7, 113.0, 66.4, 51.7, 47.1, 44.5, 38.3, 37.7, 32.8, 32.1, 29.3, 28.7, 26.9, 25.8, 25.3, 23.9, 21.6, 9.1. MS(FAB): (M+Na)$^+$ 1205.

EXAMPLE 3

N,N'-Bis[3-(3-((1R)-1-((2S)-(3,3-dimethyl-1,2-dioxopentyl)piperidine-2-carbonyloxo)-3-phenyl) propylphenoxy)propyl] pyridine-2,6-dicarboxamide (33)

Following the same procedure as in Example 1 except replacing pyridine-2,6-dicarboxylic acid for 1,4-phenylenediacetic acid, obtained 33 (44 mg, 54%) as a white solid. mp 60–62 ° C.; $^1$H NMR (CDCl$_3$, 300 MHz) (single diastereomer, mixture of rotamers) 8.34 (d, J=7.7 Hz, 2 H), 8.00 (t, J=7.7 Hz, 1 H), 7.99 (br. s, 2 H, NHs), 7.30–6.75 (m, 18 H), 5.77 (t, J=5.7 Hz, 2 H), 5.30 (d, J=4.8 Hz, 2 H), 4.02 (m, 4 H), 3.63 (m, 4 H), 3.35 (d, J=12.7 Hz, 2 H), 3.20 (td, J=12.7, 2.8 Hz, 2 H), 2.60 (m, 4 H), 2.36 (d, J=13.3 Hz, 2 H), 2.24 (m, 2 H), 2.05 (m, 6 H), 1.80–1.65 (m, 10 H), 1.50 (m, 4 H), 1.20 (s, 6 H), 1.18 (s, 6 H), 0.85 (t, J=7.4 Hz, 6 H); $^{13}$C NMR (CDCl$_3$, 75 MHz) (single diastereomer, mixture of rotamers) 208.2, 170.1, 167.7, 164.0, 159.3, 149.1, 142.0, 141.2, 139.3, 130.2, 128.9, 128.7, 126.5, 125.4, 119.4, 115.1, 113.2, 107.9, 67.0, 57.1, 51.6, 47.1, 44.5, 38.3, 37.9, 32.8, 32.1, 29.6, 28.0, 26.9, 25.4, 23.9, 23.5, 21.6, 9.1. MS(FAB): (M+Na)$^+$ 1198, (M+H)$^+$ 1176.

EXAMPLE 4

N,N'-Bis[3-(3-((1R)-1-((2S)-(3,3-dimethyl-1,2-dioxopentyl)piperidine-2-carbonyloxo)-3-phenyl) propylphenoxy)propyl] pyridine-3,5-dicarboxamide (34)

Following the same procedure as in Example 1 except replacing pyridine-3,5-dicarboxylic acid for 1,4-phenylenediacetic acid, obtained 34 (32 mg, 39%) as a white solid. mp 62–64° C.; $^1$H NMR (CDCl$_3$, 300 MHz) (single diastereomer, mixture of rotamers) 9.09 (d, J=1.8 Hz, 2 H), 8.42 (d, J=1.9 Hz, 1 H), 7.30–6.80 (m, 20 H), 5.78 (t, J=5.6 Hz, 2 H), 5.28 (d, J=4.7 Hz, 2 H), 4.12 (t, J=5.6 Hz, 4 H), 3.68 (m, 4 H), 3.36 (d, J=13.0 Hz, 2 H), 3.18 (td, J=13.4, 3.4 Hz, 2 H), 2.60 (m, 4 H), 2.35 (d, J=13.2 Hz, 2 H), 2.25 (m, 2 H), 2.05 (m, 6 H), 1.80–1.65 (m, 10 H), 1.50 (m, 4 H), 1.18 (s, 6 H), 1.16 (s, 6 H), 0.84 (t, J=7.4 Hz, 6 H); $^{13}$C NMR (CDCl$_3$, 75 MHz) (single diastereomer, mixture of rotamers) 208.3, 170.1, 167.8, 165.2, 159.1, 150.9, 141.9, 141.3, 130.3, 130.2, 128.9, 128.7, 126.5, 119.5, 115.0, 112.7, 107.9, 67.0, 51.7, 47.1, 44.5, 38.7, 38.2, 32.8, 32.1, 26.8, 25.3, 23.9, 23.5, 21.5, 9.1. MS(FAB): (M+Na)$^+$ 1198, (M+H)$^+$ 1176.

EXAMPLE 5

N,N'-Bis[3-(3-((1R)-1-((2S)-(3,3-dimethyl-1,2-dioxopentyl)piperidine-2-carbonyloxo)-3-phenyl)propylphenoxy)propyl] N-methyl-pyridinium-3,5-dicarboxarnide iodide (35)

A solution of 34 (10 mg, 8.5 μmol) in acetone (1.0 mL) was treated with MeI (60 μL, 10.2 mmol). The mixture was left to stand at room temperature under dark for 3 d and TLC (100% EtOAc) showed all starting material converted to a baseline compound. The resulting deep yellow solution was concentrated in vacuo to afford 35 (11 mg, 100%) as a yellow solid. $^1$H NMR (Acetone-$d_6$, 300 MHz) (single diastereomer, mixture of rotamers) 9.98 (s, 1 H), 9.62 (s, 2 H), 9.14 (br. s, 2 H), 7.20–6.70 (m, 20 H), 5.83 (t, J=5.2 Hz, 2 H), 5.27 (d, J=4.5 Hz, 2 H), 4.75 (s, 3 H), 4.18 (t, J=6.4 Hz, 4 H), 3.67 (q, J=6.1 Hz, 4 H), 3.45 (d, J=13.4 Hz, 2 H), 3.25 (m, 2 H), 2.75 (m, 4 H), 2.20–1.90 (m, 10 H), 1.75 (m, 10 H), 1.50 (m, 4 H), 1.21 (s, 6 H), 1.19 (s, 6 H), 0.85 (t, J=7.5 Hz, 6 H); $^{13}$C NMR (Acetone-$d_6$, 75 MHz) (single diastereomer, mixture of rotamers) 208.7, 170.8, 168.2, 162.1, 160.6, 148.7, 143.3, 142.6, 130.8, 129.6, 127.2, 119.8, 115.6, 113.9, 104.0, 77.8, 67.2, 52.5, 47.6, 45.3, 39.4, 38.1, 33.6, 32.8, 27.6, 26.1, 24.2, 23.8, 22.4, 9.5. MS(FAB): M+ 1190.

EXAMPLE 6

N,N'-Bis[3-(3-((1R)-1-((2S)-(3,3-dimethyl-1,2-dioxopentyl)piperidine-2-carbonyloxo)-3-phenyl)propylphenoxy)propyl] benzene-1,3-disulfonarnide (36)

A solution of 24 (106 mg, 0.17 mmol) in $CH_2Cl_2$ (2.0 mL) was treated with $Et_3N$ (71 μL, 0.51 mmol) and benzene-1,3-disulfonyl chloride (23 mg, 0.085 mnmol). The mixture was stirred at room temperature overnight. The resulting yellow solution was then impregnated on silica gel and evaporated to dryness. Chromatography (silica gel, 50% EtOAc/hexanes) afforded 36 (64 mg, 61%) as a white solid. mp 58–60° C.; $^1$H NMR ($CDCl_3$, 300 MHz) (single diastereomer, mixture of rotamers) 8.39 (d, J=6.3 Hz, 1 H), 8.03 (dd, J=7.8, 1.6 Hz, 2 H), 7.57 (td, J=7.9, 4.4 Hz, 1 H), 7.35–6.80 (m, 18 H), 5.81 (m, 2 H), 5.50 (m, 2 H), 5.36 (d, J=4.4 Hz, 2 H), 3.95 (m, 4 H), 3.43 (d, J=12.6 Hz, 2 H), 3.22 (m, 6 H), 2.65 (m, 4 H), 2.43 (d, J=13.6 Hz, 2 H), 2.30 (m, 2 H), 2.15 (m, 2 H), 1.95 (m, 4 H), 1.90–1.65 (m, 12 H), 1.50 (m, 4 H), 1.25 (s, 6 H), 1.23 (s, 6 H), 0.90 (t, J=7.4 Hz, 6 H); $^{13}$C NMR ($CDCl_3$, 75 MHz) (single diastereomer, mixture of rotamers) 208.5, 170.1, 167.8, 159.0, 142.1, 141.9, 141.3, 131.1, 130.5, 130.1, 128.9, 128.7, 126.5, 125.8, 119.5, 114.8, 112.7, 65.7, 57.2, 51.8, 47.1, 44.6, 41.2, 38.4, 32.9, 32.8, 32.1, 29.5, 26.8, 25.3, 23.9, 23.4, 21.6, 9.2, 9.1. MS(FAB): (M+Na)+ 1269.

EXAMPLE 7

N,N'-Bis[3-(3-((1R)-1-((2S)-(3,3-dimethyl-1,2-dioxopentyl)piperidine-2-carbonyloxo)-3-phenyl)propylphenoxy)propyl] 5-aminobenzene-1,3-dicarboxamide (37)

A mixture of 5-aminoisophthalic acid (1.81 g, 10 mmol) and dioxane (60 mL) was treated with a solution of $Na_2CO_3$ (4.24 g, 40 mmol) in water (60 mL) and then with $(Boc)_2O$ (3.5 mL, 15 mmol). The mixture was stirred at room temperature for 16 h. EtOAc (100 mL) was added to the mixture and 10% $KHSO_4$ (ca. 100 mL) added to bring the pH to 2. The organic layer was separated and the aqueous layer was extracted with EtOAc (2×100 mL). The combined EtOAc solution was washed with saturated brine, dried ($Na_2SO_4$), and concentrated in vacuo to give 5-tert-butyloxycarbamyl-benzene-1,3-dicarboxylic acid (2.8 g, 100%).

A mixture of the above diacid (422 mg, 1.5 mmol) and disuccinimidyl carbonate (768 mg, 3.0 mmol) in acetonitrile (20 mL) was treated with pyridine (364 μL, 4.5 mmol). The mixture was stirred vigorously at room temperature for 20 h. The resulting suspension was partitioned between EtOAc (150 mL) and 0.5 N HCl (50 mL). The organic layer was separated and then washed with water (50 mL), 10% $NaHCO_3$ (2×50 mL), saturated brine, dried ($Na_2SO_4$), and concentrated in vacuo. Chromatography (silica gel, 70% EtOAc/hexanes) afforded disuccinimidyl (5-tert-butyloxycarbamyl)benzene-1,3-dicarboxylate (193 mg, 27%) as a white solid. $^1$H NMR ($CDCl_3$, 300 MHz) 8.50 (s, 1 H), 8.44 (s, 2 H), 6.91 (s, 1 H), 2.89 (s, 8 H), 1.54 (s, 9 H.

To a solution of 24 (81 mg, 0.127 mmol) in $CH_2Cl_2$ (2.0 mL) was added the above activated diester (30 mg, 0.064 mmol), followed by dropwise addition of $Et_3N$ (53 μL, 0.38 mmol). The mixture was stirred at room temperature for 4 h. The resulting clear solution was impregnated on silica gel and evaporated to dryness. Chromatography (silica gel, 50–70% EtOAc/hexanes) provided N-Boc-37 (56 mg, 68%) as a white solid. $^1$H NMR ($CDCl_3$, 300 MHz) (single diastereomer, mixture of rotamers) 8.01 (s, 2 H), 7.93 (s, 1 H), 7.35–6.85 (m, 21 H), 5.83 (t, J=6.0 Hz, 2 H), 5.34 (d, J=4.6 Hz, 2 H), 4.14 (t, J=5.2 Hz, 4 H), 3.70 (m, 4 H), 3.42 (d, J=12.8 Hz, 2 H), 3.22 (t, J=10.2 Hz, 2 H), 2.65 (m, 4 H), 2.40 (d, J=13.0 Hz, 2 H), 2.30 (m, 2 H), 2.15 (m, 6 H), 1.85–1.65 (m, 10 H), 1.57 (s, 9 H), 1.50 (m, 4 H), 1.25 (s, 6 H), 1.23 (s, 6 H), 0.91 (t, J=7.4 Hz, 6 H); $^{13}$C NMR ($CDCl_3$, 75 MHz) (single diastereomer, mixture of rotamers) 208.4, 170.1, 167.8, 166.8, 159.3, 153.1, 141.7, 141.3, 139.9, 136.1, 130.1, 128.8, 128.7, 126.5, 119.7, 119.4, 115.0, 112.8, 66.7, 51.7, 47.1, 44.5, 38.4, 38.2, 32.8, 32.1, 29.4, 28.7, 26.8, 25.3, 23.4, 21.5, 9. 1.

A solution of N-Boc-37 (20 mg, 0.016 mmol) in $CH_2Cl_2$ (4.0 mL) was treated with trifluoroacetic acid (0.8 mL) and the mixture was stirred at room temperature for 1 h. The mixture was diluted with toluene (150 mL) and concentrated in vacuo to give 37 trifluoroacetic acid salt (20 mg, 96%) as a colorless gum. $^1$H NMR ($CDCl_3$, 300 MHz) (single diastereomer, mixture of rotamers) 7.67 (s, 1 H), 7.45–6.90 (m, 22 H), 5.88 (m, 2 H), 5.40 (d, J=4.6 Hz, 2 H), 4.80 (br. s, 4 H), 4.20 (m, 4 H), 3.75 (m, 4 H), 3.45 (d, J=12.7 Hz, 2 H), 3.32 (m, 2 H), 2.75 (m, 4 H), 2.50–2.30 (m, 4 H), 2.20 (m, 6 H), 1.78 (m, 10 H), 1.50 (m, 4 H), 1.32 (s, 6 H), 1.30 (s, 6 H), 0.98 (t, J=7.4 Hz, 6 H). MS(FAB): (M+H)+ 1190.

EXAMPLE 8

N,N'-Bis[3-(3-((1R)-1-((2S)-(3,3-dimethyl-1,2-dioxopentyl)piperidine-2-carbonyloxo)-3-phenyl)propylphenoxy)propyl] (±)-2,6-diaminopimelamide (38)

Following the same procedures as in Example 7 except replacing (±)-2,6-diaminopimelic acid for 5-aminoisophthalic acid, obtained di-Boc-38 (51 mg, 54%) as a white solid. $^1$H NMR ($CDCl_3$, 300 MHz) (single diastereomer, mixture of rotamers) 7.35–6.50 (m, 20 H), 5.84 (t, J=5.8 Hz, 2 H), 5.45–5.20 (m, 4 H), 4.08 (t, J=5.4 Hz, 4 H), 3.55–3.30 (m, 6 H), 3.24 (t, J=12.5 Hz, 2 H), 2.70 (m, 4 H), 2.42 (d, J=13.0 Hz, 2 H), 2.35 (m, 2 H), 2.20 (m, 2 H), 2.05 (m, 4 H), 2.00–1.65 (m, 14 H), 1.50 (m, 4 H), 1.47 (s, 18 H), 1.28 (s, 6 H), 1.25 (s, 6 H), 0.94 (t, J=7.4 Hz, 6 H); $^{13}$C NMR ($CDCl_3$, 75 MHz) (single diastereomer, mixture of rotamers) 208.3, 170.1, 159.3, 141.8, 141.3, 130.1, 128.9, 128.7, 126.5, 119.3, 113.1, 80.4, 66.7, 51.7, 47.1, 44.5, 38.3, 32.8, 32.1, 29.5, 28.74, 28.72, 26.9, 25.3, 24.0, 23.4, 21.6, 9.1.

A solution of di-Boc-38 (20 mg, 0.014 mmol) in $CH_2Cl_2$ (4.0 mL) was treated with trifluoroacetic acid (0.8 mL) and the mixture was stirred at room temperature for 1 h. The mixture was diluted with toluene (150 mL) and concentrated in vacuo to give 38 di-(trifluoroacetic acid) salt (18.9 mg, 94%) as a colorless gum. $^1$H NMR (CDCl$_3$, 300 MHz) (single diastereomer, mixture of rotamers) 7.40–6.85 (m, 20 H), 5.85 (m, 2 H), 5.38 (m, 2 H), 4.05 (m, 6 H), 3.45–3.25 (m, 8 H), 2.70 (m, 4 H), 2.45 (m, 2 H), 2.40 (m, 2 H), 2.20 (m, 2 H), 2.05 (m, 4 H), 1.95–1.60 (m, 14 H), 1.50 (m, 4 H), 1.28 (s, 6 H), 1.27 (s, 6 H), 0.95 (t, J=7.4 Hz, 6 H), MS(FAB): (M+H)$^+$ 1199.

EXAMPLE 9

N,N'-Bis[3-(3-((1R)-1-((2S)-(3,3-dimethyl-1,2-dioxopentyl)piperidine-2-carbonyloxo)-3-phenyl)propylphenoxy)propyl] triethyleneglycol-1,10-biscarbamate (39)

To a solution of 24 (85 mg, 0.13 mmol) in CH$_2$Cl$_2$ at 0° C. was added Et$_3$N, followed by triethylene glycol bis (chloroformate). The mixture was stirred at 0° C. for 1 h, and TLC showed no starting material left. The mixture was concentrated in vacuo and the residue was chromatographed on silica (70–80% EtOAc/hexanes) to give 39 as a colorless gum, 40 mg (48%). $^1$H NMR (CDCl$_3$, 300 MHz) (single diastereomer, mixture of rotamers) 7.25–6.70 (m, 18 H), 5.71 (t, J=5.8 Hz, 2 H), 5.25 (d, J=4.7Hz, 2 H), 5.12 (br. s, 2 H), 4.15 (t, J=4.4 Hz, 4 H), 3.95 (t, J=5.9 Hz, 4 H), 3.60 (t, J=4.8 Hz, 4 H), 3.57 (s, 4 H), 3.30 (m, 6 H), 3.10 (td, J=12.7, 3.0 Hz, 2 H), 2.50 (m, 4 H), 2.30 (d, J=13.7 Hz, 2 H), 2.20 (m, 2 H), 2.05 (m, 2 H), 1.92 (t, J=6.2 Hz, 4 H), 1.75–1.50 (m, 10 H), 1.35 (m, 4H), 1.16 (s, 6 H), 1.13 (s, 6 H), 0.81 (t, J=7.4 Hz, 6 H); $^{13}$C NMR (CDCl$_3$, 75 MHz) (single diastereomer, mixture of rotamers) 208.2, 170.1, 167.6, 159.3, 159.9, 156.9, 141.7, 141.3, 130.1, 128.9, 128.7, 126.5, 119.4, 114.8, 113.2, 71.0, 70.1, 66.0, 64.3, 51.7, 47.1, 44.5, 39.2, 38.8, 38.3, 33.0, 32.9, 32.1, 29.9, 26.8, 25.4, 23.9, 23.8, 23.5, 21.6, 9.1. MS(FAB): (M+Na)$^+$ 1269.

EXAMPLE 10

1,4-Xylyldiamine N,N'-bis[2-(3-((1R)-1-((2S)-(3,3-dimethyl-1,2-dioxopentyl)piperidine-2-carbonyloxo)-3-phenyl)propy)phenoxyacetamide] (40)

A solution of carboxylic acid 25 (104 mg, 0.20 mmol) in acetonitrile (2.0 mL) was treated with disuccinimidyl carbonate (56 mg, 0.22 mmol) and pyridine (48 μL, 0.60 mmol). The mixture was stirred at room temperature overnight. The mixture was then partitioned between EtOAc (70 mL) and water (50 mL). The organic phase was separated, washed with saturated brine, dried (Na$_2$ SO$_4$), and concentrated in vacuo to give a white foam (115 mg, 93%). The activated succinimidyl ester was redissolved in anhydrous acetonitrile (2.0 mL). The solution was then treated with triethylamine (75 μL, 0.54 mmol) followed by a solution of 1,4-xylyldiamine in DMF (0.32 M, 288 μL, 0.092 mmol). The resulting suspension was stirred at room temperature for 1 h and TLC showed no starting material left. The mixture was partitioned between EtOAc (50 mL) and water (20 mL). The organic layer was separated, washed with 0.5 N HCl (aq.), saturated brine, dried (Na$_2$SO$_4$) and concentrated in vacuo. Chromatography (silica gel, 70% EtOAc/hexanes) afforded 40 (42 mg, 40%) as a white solid: mp 59–61° C.; $^1$H NMR (CDCl$_3$, 300 MHz) (single diastereomer, mixture of rotamers) 7.25–6.70 (m, 22 H), 5.69 (m, 2 H), 5.22 (d, J=4.8 Hz, 2 H), 4.46 (s, 4 H), 4.43 (d, J=3.9 Hz, 4 H), 3.27 (d, J=13.2 Hz, 2 H), 3.06 (td, J=12.6, 2.6 Hz, 2 H), 2.50 (m, 4 H), 2.27 (d, J=13.4 Hz, 2 H), 2.16 (m, 2 H), 2.00 (m, 2 H), 1.75–1.50 (m, 10 H), 1.35 (m, 4 H), 1.12 (s, 6 H), 1.10 (s, 6 H), 0.78 (t, J=7.4 Hz, 6 H); $^{13}$C NMR (CDCl$_3$, 75 MHz) (single diastereomer, mixture of rotamers) 208.3, 170.0, 168.4, 168.3, 167.6, 157.7, 142.2, 142.1, 141.1, 137.6, 130.4, 128.9, 128.7, 128.5, 126.6, 120.6, 114.3, 113.8, 67.7, 57.0, 51.6, 47.1, 44.5, 43.0, 39.2, 38.4, 38.1, 32.9, 32.1, 32.0, 26.8, 25.3, 23.9, 23.5, 21.6, 9.2. MS(FAB): (M+Na)$^+$ 1169, (M+H)$^+$ 1147.

EXAMPLE 11

1,4-Bis(3-aminopropyl)piperazine N,N'-bis[2-(3-((1R)-1-((2S)-(3,3-dimethyl-1,2-dioxopentyl)piperidine-2-carbonyloxo)-3-phenyl)propyl)phenoxyacetamide] (41)

Following the same method as in Example 10 except replacing 1,4-bis(3-aminopropyl)piperazine for 1,4-xylyldiamine, obtained 41 (35 mg, 53%) as a white solid. $^1$H NMR (CDCl$_3$, 300 MHz) (single diastereomer, mixture of rotamers) 7.55–6.90 (m, 20 H), 5.93 (t, J=5.6 Hz, 2 H), 5.46 (d, J=4.8 Hz, 2 H), 4.63 (s, 4 H), 3.70–3.50 (m, 6 H), 3.37 (m, 2 H), 2.95–2.20 (m, 24 H), 1.90 (m, 16 H), 1.60 (m, 4 H), 1.37 (s, 6 H), 1.35 (s, 6 H), 1.03 (t, J=7.5 Hz, 6 H); $^{13}$C NMR (CDCl$_3$, 75 MHz) (single diastereomer, mixture of rotamers) 208.2, 170.0, 168.4, 167.7, 158.0, 142.3, 141.1, 130.4, 128.9, 128.7, 126.6, 120.5, 115.0, 113.8, 107.9, 68.2, 51.6, 47.1, 44.5, 38.5, 32.9, 26.8, 25.3, 23.9, 23.5, 21.6, 9.1. MS(FAB): (M+H)$^+$ 1211.

EXAMPLE 12

3,3'-Diamino-N-methyldipropylamine N,N'-bis[2-(3-((1R)-1-((2S)-(3,3-dimethyl-1,2-dioxopentyl)piperidine-2-carbonyloxo)-3-phenyl)propy)phenoxyacetaride] (42)

Following the same method as in Example 10 except replacing 3,3'-Diamino-N-methyldipropylamine for 1,4-xylyldiamine, obtained 42 (28 mg, 48%) as a colorless gum. $^1$H NMR (CDCl$_3$, 300 MHz) (single diastereomer, mixture of rotamers) 7.50–6.75 (m, 20 H), 5.76 (t, J=5.8 Hz, 2 H), 5.29 (d, J=4.8 Hz, 2 H), 4.45 (s, 4 H), 3.35 (m, 6 H), 3.17 (td, J=12.6, 2.7 Hz, 2 H), 2.60 (m, 4 H), 2.35 (m, 6 H), 2.25 (m, 2 H), 2.05 (m, 5 H), 1.70 (m, 14 H), 1.40 (m, 4 H), 1.20 (s, 6 H), 1.18 (s, 6 H), 0.86 (t, J=7.5 Hz, 6 H); $^{13}$C NMR (CDCl$_3$, 75 MHz) (single diastereomer, mixture of rotamers) 208.2, 170.0, 168.4, 167.7, 158.0, 142.2, 141.1, 130.4, 128.9, 128.7, 126.5, 120.3, 115.0, 114.6, 113.7, 108.0, 67.9, 56.4, 51.6, 47.1, 44.5, 38.4, 33.0, 32.9, 32.1, 26.8, 25.3, 23.9, 23.5, 21.6, 21.4, 9.1. MS(FAB): (M+H)$^+$ 1156, (M+Na)$^+$ 1178.

EXAMPLE 13

1,5-Diaminopentane N,N'-bis[2-(3-((1R)-1-((2S)-(3,3-dimethyl-1,2-dioxopentyl)piperidine-2-carbonyloxo)-3-phenyl)propyl)phenoxyacetamide] (43)

Following the same method as in Example 10 except replacing 1,5-diaminopentane for 1,4-xylyldiamine, obtained 43 (18 mg, 30%) as a colorless gum. $^1$H NMR (CDCl$_3$, 300 MHz) (single diastereomer, mixture of rotamers) 7.40–7.00 (m, 18 H), 6.80 (br. s., NHs, 2 H), 5.85 (m, 2 H), 5.33 (d, J=4.7 Hz, 2 H), 4.50 (s, 4 H), 3.37 (m, 6 H), 3.20 (td, J=12.7, 2.7 Hz, 2 H), 2.65 (m, 4 H), 2.38 (d, J=13.4 Hz, 2 H), 2.28 (m, 2 H), 2.14 (m, 2 H), 1.90–1.40 (m, 20 H), 1.24 (s, 6 H), 1.22 (s, 6 H), 0.90 (t, J=7.4 Hz, 6 H); $^{13}$C NMR (CDCl$_3$, 75 MHz) (single diastereomer, mixture of rotamers) 208.2, 170.0, 168.3, 167.7, 157.8, 142.2, 141.2, 130.4, 128.9, 128.7, 126.5, 120.5, 114.2, 113.9, 67.8, 51.6, 47.1, 44.5, 39.2, 38.4, 32.9, 32.0, 29.6, 26.8, 25.4, 24.4, 23.9, 23.5, 21.6, 9.1. MS(FAB): (M+Na)$^+$ 1135.

EXAMPLE 14

1,5-Diamino-3-oxapetane N,N'-bis[2-(3-((1R)-1-((2S)-(3,3-dimethyl-1,2-dioxopentyl)piperidine-2-carbonyloxo)-3-phenyl)propyl)phenoxyacetamide] (48)

Following the same method as in Example 10 except replacing 1,5-diamino-3-oxapentane dihydrochloride (Aldrich) for 1,4-xylyldiamine, obtained 48 (23 mg, 39%) as a colorless gum. $^1$H NMR (CDCl$_3$, 300 MHz) (single diastereomer, mixture of rotamers) 7.30–6.80 (m, 20 H), 5.80 (m, 2 H), 5.30 (d, J=4.9 Hz, 2 H), 4.48 (s, 4 H), 3.50 (br. s, 8 H), 3.36 (d, J=13.6 Hz, 2 H), 3.16 (td, J=12.6, 2.7 Hz, 2 H), 2.60 (m, 4 H), 2.36 (d, J=13.8 Hz, 2 H), 3.26 (m, 2 H), 2.10 (m, 2 H), 1.80–1.60 (m, 10 H), 1.50 (m, 4 H), 1.20 (s, 6 H), 1.19 (s, 6 H), 0.87 (t, J=7.5 Hz, 6 H); $^{13}$C NMR (CDCl$_3$, 75 MHz) (single diastereomer, mixture of rotamers) 208.2, 170.0, 168.5, 167.7, 157.8, 142.2, 141.1, 130.4, 128.9, 128.7, 126.5, 120.5, 114.6, 113.7, 108.1, 69.9, 67.8, 51.6, 47.1, 44.5, 39.1, 38.4, 32.9, 32.0, 26.8, 25.3, 23.9, 23.5, 21.6, 21.4, 9.1. MS(FAB): (M+Na)$^+$ 1137.

EXAMPLE 15
1,8-Diamino-3,6-dioxaoctane N,N-bis[2-(3-((1R)-1-((2S)-(3,3-dimethyl-1,2-dioxopentyl)piperidine-2-carbonyloxo)-3-phenyl)propyl)phenoxyacetamide] (53)

Following the same method as in Example 10 except replacing 1,8-diamino-3,6-dioxaoctane (Fluka) for 1,4-xylyldiamine, obtained 53 (23 mg, 32%) as a colorless gum. $^1$H NMR (CDCl$_3$, 300 MHz) (single diastereomer, mixture of rotamers) 7.35–6.85 (m, 20 H), 5.80 (t, J=5.7 Hz, 2 H), 5.33 (d, J=4.9 Hz, 2 H), 4.51 (s, 4 H), 3.60 (br. s, 12 H), 3.40 (d, J=12.3 Hz, 2 H), 3.20 (td, J=12.6, 2.8 Hz, 2 H), 2.65 (m, 4 H), 2.40 (d, J=13.4 Hz, 2 H), 2.26 (m, 2 H), 2.10 (m, 2 H), 1.90–1.60 (m, 10 H), 1.50 (m, 4 H), 1.25 (s, 6 H), 1.22 (s, 6 H), 0.90 (t, J=7.4 Hz, 6 H); $^{13}$C NMR (CDCl$_3$, 75 MHz) (single diastereomer, mixture of rotamers) 208.2, 170.0, 168.4, 167.7, 157.8, 142.2, 141.1, 130.4, 128.9, 128.7, 126.5, 120.5, 114.7, 113.6, 70.7, 70.1, 67.8, 51.6, 47.1, 44.5, 39.2, 38.4, 32.9, 32.0, 26.8, 25.3, 23.9, 23.5, 21.6, 21.4, 9.1. MS(FAB): (M+Na)$^+$ 1181.

EXAMPLE 16
1,11-Diamino-3,6,9-trioxaundecane N,N'-bis[2-(3-((1R)-1-((2S)-(3,3-dimethyl-1,2-dioxopentyl)piperidine-2-carbonyloxo)-3-phenyl)propyl)phenoxyacetamide] (59)

Following the same method as in Example 10 except replacing 1,11-Diamino-3,6,9-trioxaundecane (prepared using literature procedure of Dietrich, B.; Lehn, J.-M.; Sauvage, J. P.; Blanzat, J. *Tetrahedron*, 1973, 29, 1628) for 1,4-xylyldiamine, obtained 59 (18 mg, 24%) as a colorless gum. $^1$H NMR (CDCl$_3$, 300 MHz) (single diastereomer, mixture of rotamers) 7.35–6.80 (m, 20 H), 5.77 (t, J=6.0 Hz, 2 H), 5.30 (d, J=4.9 Hz, 2 H), 4.48 (s, 4 H), 3.60 (m, 16 H), 3.35 (d, J=13.5 Hz, 2 H), 3.16 (td, J=12.6, 2.9 Hz, 2 H), 2.65 (m, 4 H), 2.37 (d, J=13.6 Hz, 2 H), 2.25 (m, 2 H), 2.05 (m, 2 H), 1.80–1.60 (m, 12 H), 1.50 (m, 4 H), 1.21 (s, 6 H), 1.19 (s, 6 H), 0.87 (t, J=7.4 Hz, 6 H); $^{13}$C NMR (CDCl$_3$, 75 MHz) (single diastereomer, mixture of rotamers) 208.2, 170.0, 168.4, 167.7, 157.8, 142.2, 141.1, 130.4, 128.9, 128.7, 126.5, 120.5, 114.7, 113.6, 108.0, 70.9, 70.7, 70.1, 67.8, 51.6, 47.1, 44.5, 39.2, 38.4, 32.9, 32.0, 26.8, 25.3, 23.9, 23.5, 21.6, 9.1. MS(FAB): (M+Na)$^+$ 1125.

EXAMPLE 17
1,5-Diaminopentane N,N'-bis[2-(3-((1R)-1-((2S)-(3,3-dimethyl-1,2-dioxopentyl)piperidine-2-carbonyloxo)-3-(3,4-dimethoxyphenyl))propyl)phenoxy-acetamide] (44)

Following the same method as in Example 10 except replacing the acid monomer 26 for 25 and replacing 1,5-diaminopentane for 1,4-xylyldiamine, obtained 44 (58 mg, 49%) as a white foam. $^1$H NMR (CDCl$_3$, 300 MHz) (single diastereomer, mixture of rotamers) 7.35–6.65 (m, 16 H), 5.79 (m, 2 H), 5.33 (d, J=4.8 Hz, 2 H), 4.49 (s, 4 H), 3.87 (s, 6 H), 3.86 (s, 6 H), 3.35 (m, 6 H), 3.20 (m, 2 H), 2.95 (m, 2 H), 2.60 (m, 4 H), 2.38 (d, J=13.4 Hz, 2 H), 2.28 (m, 2 H), 2.10 (m, 2 H), 1.90–1.40 (m, 20 H), 1.23 (s, 6 H), 1.22 (s, 6 H), 0.90 (t, J=7.4 Hz, 6 H); $^{13}$C NMR (CDCl$_3$, 75 MHz) (single diastereomer, mixture of rotamers) 208.2, 170.0, 168.3, 168.2, 167.7, 157.8, 149.3, 147.8, 142.3, 133.8, 130.4, 120.6, 114.2, 113.9, 112.2, 111.8, 108.0, 67.8, 56.3, 56.2, 51.6, 47.1, 44.5, 39.2, 38.6, 38.3, 32.9, 31.6, 29.6, 26.8, 25.3, 24.4, 23.8, 23.6, 9.1. MS(FAB): (M+Na)$^+$ 1255.

EXAMPLE 18
1,5-Diamino-3-oxapetane N,N'-bis[2-(3-((1R)-1-((2S)-(3,3-dimethyl-1,2-dioxopentyl)piperidine-2-carbonyloxo)-3-(3,4-dimethoxyphenyl))propyl)phenoxy-acetamide] (49)

Following the same method as in Example 10 except replacing the acid monomer 26 for 25 and replacing 1,5-diamino-3-oxapentane dihydrochloride (Aldrich) for 1,4-xylyldiamine, obtained 49 (73 mg, 62%) as a white foam. $^1$H NMR (CDCl$_3$, 300 MHz) (single diastereomer, mixture of rotamers) 7.35–6.65 (m, 16 H), 5.79 (m, 2 H), 5.33 (d, J=4.8 Hz, 2 H), 4.51 (s, 4 H), 3.87 (s, 6 H), 3.86 (s, 6 H), 3.55 (br.s, 8 H), 3.35 (m, 2 H), 3.20 (m, 2 H), 2.60 (m, 4 H), 2.38 (d, J=13.4 Hz, 2 H), 2.28 (m, 2 H), 2.10 (m, 2 H), 1.90–1.40 (m, 20 H), 1.23 (s, 6 H), 1.22 (s, 6 H), 0.90 (t, J=7.4 Hz, 6 H); $^{13}$C NMR (CDCl$_3$, 75 MHz) (single diastereomer, mixture of rotamers) 208.2, 170.0, 168.5, 168.4, 167.7, 157.8, 149.3, 147.8, 142.3, 133.7, 130.4, 120.5, 114.6, 113.7, 112.2, 111.8, 69.9, 67.8, 56.3, 56.2, 51.6, 47.1, 44.5, 39.1, 38.6, 32.9, 31.6, 26.8, 25.3, 23.8, 23.6, 21.6, 9.1. MS(FAB): (M+Na)$^+$ 1257.

EXAMPLE 19
1,8-Diamino-3,6-dioxaoctane N,N'-bis[2-(3-((1R)-1-((2S)-(3,3-dimethyl-1,2-dioxopentyl)piperidine-2-carbonyloxo)-3-(3,4-dimethoxyphenyl))propyl)phenoxy-acetamide] (54)

Following the same method as in Example 10 except replacing the acid monomer 26 for 25 and replacing 1,8-diamino-3,6-dioxaoctane (Fluka) for 1,4-xylyldiamine, obtained 54 (54 mg, 49%) as a white foam. $^1$H NMR (CDCl$_3$, 300 MHz) (single diastereomer, mixture of rotamers) 7.35–6.65 (m, 16 H), 5.79 (m, 2 H), 5.33 (d, J=4.8 Hz, 2 H), 4.50 (s, 4 H), 3.87 (s, 6 H), 3.86 (s, 6 H), 3.59 (br.s, 12 H), 3.35 (m, 2 H), 3.20 (m, 2 H), 2.60 (m, 4 H), 2.38 (d, J=13.4 Hz, 2 H), 2.28 (m, 2 H), 2.10 (m, 2 H), 1.90–1.40 (m, 20 H), 1.23 (s, 6 H), 1.22 (s, 6 H), 0.90 (t, J=7.4 Hz, 6 H); $^{13}$C NMR (CDCl$_3$, 75 MHz) (single diastereomer, mixture of rotamers) 208.2, 170.1, 168.4, 167.7, 157.8, 149.3, 147.8, 142.3, 133.7, 130.4, 120.5, 114.7, 113.6, 112.2, 111.8, 70.6, 70.1, 67.8, 56.3, 56.2, 51.6, 47.1, 44.5, 39.2, 38.6, 32.9, 31.6, 26.8, 25.3, 23.8, 23.6, 21.6, 9.1. MS(FAB): (M+Na)$^+$ 1301.

EXAMPLE 20
1,11-Diamino-3,6,9-trioxaundecane N,N'-bis[2-(3-((1R)-1-((2S)-(3,3-dimethyl-1,2-dioxo-pentyl)piperidine-2-carbonyloxo)-3-(3,4-dimethoxyphenyl))propyl)phenoxy-acetamide] (60)

Following the same method as in Example 10 except replacing the acid monomer 26 for 25 and replacing 1,11-Diamino-3,6,9-trioxaundecane (prepared using literature procedure of Dietrich, B.; Lehn, J.-M.; Sauvage, J. P.; Blanzat, J. *Tetrahedron*, 1973, 29, 1628) for 1,4-xylyldiamine, obtained 60 (64 mg, 50%) as a colorless gum. $^1$H NMR (CDCl$_3$, 300 MHz) (single diastereomer, mixture of rotamers) 7.35–6.65 (m, 16 H), 5.79 (m, 2 H), 5.33 (d, J=4.8 Hz, 2 H), 4.50 (s, 4 H), 3.87 (s, 6 H), 3.86 (s, 6 H), 3.61 (m, 16 H), 3.38 (m, 2 H), 3.20 (m, 2 H), 2.60 (m, 4 H), 2.38 (m, 2 H), 2.28 (m, 2 H), 2.10 (m, 2 H), 1.90–1.40 (m, 20 H), 1.23 (s, 6 H), 1.22 (s, 6 H), 0.90 (t, J=7.4 Hz, 6 H); $^{13}$C NMR (CDCl$_3$, 75 MHz) (single diastereom mixture of rotamers) 208.2, 170.1, 168.4, 167.7, 157.8, 149.3, 147.8, 142.3, 133.7, 130.4, 120.5, 114.7, 113.6, 112.2, 111.8, 108.0, 70.6, 70.1, 67.8, 56.3, 56.2, 51.6, 47.1, 44.5, 39.2, 38.6, 32.9, 31.6, 26.8, 25.3, 23.8, 23.5, 21.6, 9.1. MS(FAB): (M+Na)+ 1345.

EXAMPLE 21
1,5-Diaminopentane N,N'-bis[2-(3-((1R)-1-((2S)-(3,3-dimethyl-1,2-dioxopentyl)piperidine-2-carbonyloxo)-3-(3,4,5-trimethoxyphenyl))propyl)phenoxy-acetamide] (45)

Following the same method as in Example 10 except replacing the acid monomer 27 for 25 and replacing 1,5-diaminopentane for 1,4-xylyldiamine, obtained 45 (33 mg, 34%) as a white foam. $^1$H NMR (CDCl$_3$, 300 MHz) and $^{13}$C NMR (CDCl$_3$, 75 MHz) are correct. MS(FAB): (M+Na)+ 1315.

EXAMPLE 22
1,5-Diamino-3-oxapetane N,N'-bis[2-(3-((1R)-1-((2S)-(3,3-dimethyl-1,2-dioxopentyl)piperidine-2-carbonyloxo)-3-(3,4,5-trimethoxyphenyl))propyl)phenoxy-acetamide] (50)

Following the same method as in Example 10 except replacing the acid monomer 27 for 25 and replacing 1,5-diamino-3-oxapentane dihydrochloride (Aldrich) for 1,4-xylyldiamine, obtained 50 (41 mg, 46%) as a white foam. $^1$H NMR (CDCl$_3$, 300 MHz) and $^{13}$C NMR (CDCl$_3$, 75 MHz) are correct. MS(FAB): (M+Na)+ 1317.

EXAMPLE 23
1,8-Diamino-3,6-dioxaoctane N,N'-bis[2-(3-((1R)-1-((2S)-(3,3-dimethyl-1,2-dioxopentyl)piperidine-2-carbonyloxo)-3-(3,4,5-trimethoxyphenyl))propyl)phenoxy-acetamide] (55)

Following the same method as in Example 10 except replacing the acid monomer 27 for 25 and replacing 1,8-diamino-3,6-dioxaoctane (Fluka) for 1,4-xylyldiamine for 1,4-xylyldiamine, obtained 55 (37 mg, 38%) as a white foam. $^1$H NMR (CDCl$_3$, 300 MHz) and $^{13}$C NMR (CDCl$_3$, 75 MHz) are correct. MS(FAB): (M+Na)+ 1361.

EXAMPLE 24
1,11-Diamino-3,6,9-trioxaundecane N,N'-bis[2-(3-((1R)-1-((2S)-(3,3-dimethyl-1,2-dioxopentyl)piperidine-2-carbonyloxo)-3-(3,4,5-trimethoxyphenyl))propyl)phenoxy-acetamide] (61)

Following the same method as in Example 10 except replacing the acid monomer 27 for 25 and replacing 1,11-Diamino-3,6,9-trioxaundecane for 1,4-xylyldiamine, obtained 61 (27 mg, 32%) as a white foam. $^1$H NMR (CDCl$_3$, 300 MHz) and $^{13}$C NMR (CDCl$_3$, 75 MHz) are correct. MS(FAB): (M+Na)+ 1405.

EXAMPLE 25
1,5-Diaminopentane N,N'-bis[2-(3-((1R)-1-((2S)-(3,3-dimethyl-1,2-dioxopentyl)piperidine-2-carbonyloxo)-3-(3,4-methylenedioxyphenyl))propyl)phenoxy-acetamide] (46)

Following the same method as in Example 10 except replacing the acid monomer 28 for 25 and replacing 1,5-diaminopentane for 1,4-xylyldiamine, obtained 46 (42 mg, 42%) as a white foam. $^1$H NMR (CDCl$_3$, 300 MHz) and $^{13}$C NMR (CDCl$_3$, 75 MHz) are correct. MS(FAB): (M+Na)+ 1223.

EXAMPLE 26
5-Diamino-3-oxapetane N,N'-bis[2-(3-((1R)-1-((2S)-(3,3-dimethyl-1,2-dioxopentyl)piperidine-2-carbonyloxo)-3-(3,4-methylenedioxyphenyl))propyl)phenoxy-acetamide] (51)

Following the same method as in Example 10 except replacing the acid monomer 28 for 25 and replacing 1,5-diamino-3-oxapentane dihydrochloride (Aldrich) for 1,4-xylyldiamine, obtained 51 (39 mg, 34%) as a white foam. $^1$H NMR (CDCl$_3$, 300 MHz) and $^{13}$C NMR (CDCl$_3$, 75 MHz) are correct. MS(FAB): (M+Na)+ 1225.

EXAMPLE 27
1,8-Diamino-3,6-dioxaoctane N,N'-bis[2-(3-((1R)-1-((2S)-(3,3-dimethyl-1,2-dioxopentyl)piperidine-2-carbonyloxo)-3-(3,4-methylenedioxyphenyl))propyl)phenoxy-acetamide] (56)

Following the same method as in Example 10 except replacing the acid monomer 28 for 25 and replacing 1,8-diamino-3,6-dioxaoctane (Fluka) for 1,4-xylyldiamine for 1,4-xylyldiamine, obtained 56 (55 mg, 47%) as a white foam. $^1$H NMR (CDCl$_3$, 300 MHz) and $^{13}$C NMR (CDCl$_3$, 75 MHz) are correct. MS(FAB): (M+Na)+ 1269.

EXAMPLE 28
1,11-Diamino-3,6,9-trioxaundecane N,N'-bis[2-(3-((1R)-1-((2S)-(3,3-dimethyl-1,2-dioxopentyl)piperidine-2-carbonyloxo)-3-(3,4-methylenedioxyphenyl))propyl)phenoxy-acetamide] (62)

Following the same method as in Example 10 except replacing the acid monomer 28 for 25 and replacing 1,11-Diamino-3,6,9-trioxaundecane for 1,4-xylyldiamine, obtained 62 (52 mg, 42%) as a colorless gum. $^1$H NMR (CDCl$_3$, 300 MHz) and $^{13}$C NMR (CDCl$_3$, 75 MHz) are correct. MS(FAB): (M+Na)+ 1313.

EXAMPLE 29
1,5-Diaminopentane N,N'-bis[2-(3-((1R)-1-((2S)-(3,3-dimethyl-1,2-dioxopentyl)piperidine-2-carbonyloxo)-3-(3-pyridyl))propyl)phenoxyacetamide] (47)

Following the same method as in Example 10 except replacing the acid monomer 29 for 25 and replacing 1,5-diaminopentane for 1,4-xylyldiamine, obtained 47 (64 mg, 58%) as a white foam. $^1$H NMR (CDCl$_3$, 300 MHz) and $^{13}$C NMR (CDCl$_3$, 75 MHz) are correct. MS(FAB): (M+Na)+ 1137.

EXAMPLE 30
1,5-Diamino-3-oxapetane N,N'-bis[2-(3-((1R)-1-((2S)-(3,3-dimethyl-1,2-dioxopentyl)piperidine-2-carbonyloxo)-3-(3-pyridyl))propyl)phenoxyacetamide] (52)

Following the same method as in Example 10 except replacing the acid monomer 29 for 25 and replacing 1,5-diamino-3-oxapentane dihydrochloride (Aldrich) for 1,4-xylyldiamine, obtained 52 (52 mg, 55%) as a white foam. $^1$H NMR (CDCl$_3$, 300 MHz) and $^{13}$C NMR (CDCl$_3$, 75 MHz) are correct. MS(FAB): (M+Na)+ 1139.

EXAMPLE 31
1,8-Diamino-3,6-dioxaoctane N,N'-bis[2-(3-((1R)-1-((2S)-(3,3-dimethyl-1,2-dioxopentyl)piperidine-2-carbonyloxo)-3-(3-pyridyl))propyl)phenoxyacetamide] (57)

Following the same method as in Example 10 except replacing the acid monomer 29 for 25 and replacing 1,8-diamino-3,6-dioxaoctane (Fluka) for 1,4-xylyldiamine for 1,4-xylyldiamine, obtained 57 (48 mg, 47%) as a white foam. $^1$H NMR (CDCl$_3$, 300 MHz) and $^{13}$C NMR (CDCl$_3$, 75 MHz) are correct. MS(FAB): (M+Na)+ 1183.

EXAMPLE 32
1,11-Diamino-3,6,9-trioxaundecane N,N'-bis[2-(3-((1R)-1-((2S)-(3,3-dimethyl-1,2-dioxopentyl)piperidine-2-carbonyloxo)-3-(3-pyridyl))propyl)phenoxyacetamide] (63)

Following the same method as in Example 10 except replacing the acid monomer 29 for 25 and replacing 1,11-Diamino-3,6,9-trioxaundecane for 1,4-xylyldiamine, obtained 63 (58 mg, 55%) as a colorless gum. $^1$H NMR

EXAMPLE 33
1,8-Diamino-3,6-dioxaoctane N,N'-bis[2-(3-((1R)-1-((2S)-(3,3-dimethyl-1,2-dioxopentyl)piperidine-2-carbonyloxo)-3-(3-indolyl))propyl)phenoxyacetamide] (58)

Following the same method as in Example 10 except replacing the acid monomer 30 for 25 and replacing 1,8-diamino-3,6-dioxaoctane (Fluka) for 1,4-xylyldiamine for 1,4-xylyldiamine, obtained 58 (20 mg, 20%) as a white foam. $^1$H NMR (CDCl$_3$, 300 MHz) and $^{13}$C NMR (CDCl$_3$, 75 MHz) are correct. MS(FAB): (M+Na)$^+$ 1259.

EXAMPLE 34
Ethylenediamine N,N'-bis[2-(3-((1R)-1-((2S)-(3,3-dimethyl-1,2-dioxopentyl)piperidine-2-carbonyloxo)-3-(3,4-dimethoxyphenyl))propyl)phenoxy-acetamide] (64)

Following the same method as in Example 10 except replacing the acid monomer 26 for 25 and replacing ethylenediamine dihydrochloride for 1,4-xylyldiamine, obtained 64 (126 mg, 59%) as a white solid. $^1$H NMR (CDCl$_3$, 300 MHz) and $^{13}$C NMR (CDCl$_3$, 75 MHz) are correct. MS(FAB): (M+Na)$^+$ 1213.

EXAMPLE 35
Ethylenediamine N,N'-bis[2-(3-((1R)-1-((2S)-(3,3-dimethyl-1,2-dioxopentyl)piperidine-2-carbonyloxo)-3-(3-pyridyl))propyl)phenoxyacetamide] (65)

Following the same method as in Example 10 except replacing the acid monomer 29 for 25 and replacing ethylenediamine dihydrochloride for 1,4-xylyldiamine, obtained 65 (79 mg, 42%) as a white solid. $^1$H NMR (CDCl$_3$, 300 MHz) and $^{13}$C NMR (CDCl$_3$, 75 MHz) are correct. MS(FAB): (M+H)$^+$ 1073.

EXAMPLE 36
N,N'-Dimethylethylenediamine N,N'-bis[2-(3-((1R)-1-((2S)-(3,3-dimethyl-1,2-dioxopentyl)piperidine-2-carbonyloxo)-3-(3,4-dimethoxyphenyl))propyl)phenoxyacetamide] (66)

Following the same method as in Example 10 except replacing the acid monomer 26 for 25 and replacing N,N'-dimethylethylenediamine for 1,4-xylyldiamine, obtained 66 (118 mg, 55%) as a white solid. $^1$H NMR (CDCl$_3$, 300 MHz) and $^{13}$C NMR (CDCl$_3$, 75 MHz) are correct. MS(FAB): (M+Na)$^+$ 1241.

EXAMPLE 37
N,N'-Dimethylethylenediamine N,N'-bis[2-(3-((1R)-1-((2S)-(3,3-dimethyl-1,2-dioxopentyl)piperidine-2-carbonyloxo)-3-(3-pyridyl))propyl)phenoxyacetamide] (67)

Following the same method as in Example 10 except replacing the acid monomer 29 for 25 and replacing N,N'-dimethylethylenediamine for 1,4-xylyldiamine, obtained 67 (70 mg, 37%) as a white solid. $^1$H NMR (CDCl$_3$, 300 MHz) and $^{13}$C NMR (CDCl$_3$, 75 MHz) are correct. MS(FAB): (M+H)$^+$ 1101.

Synthetic Overview, Part II:

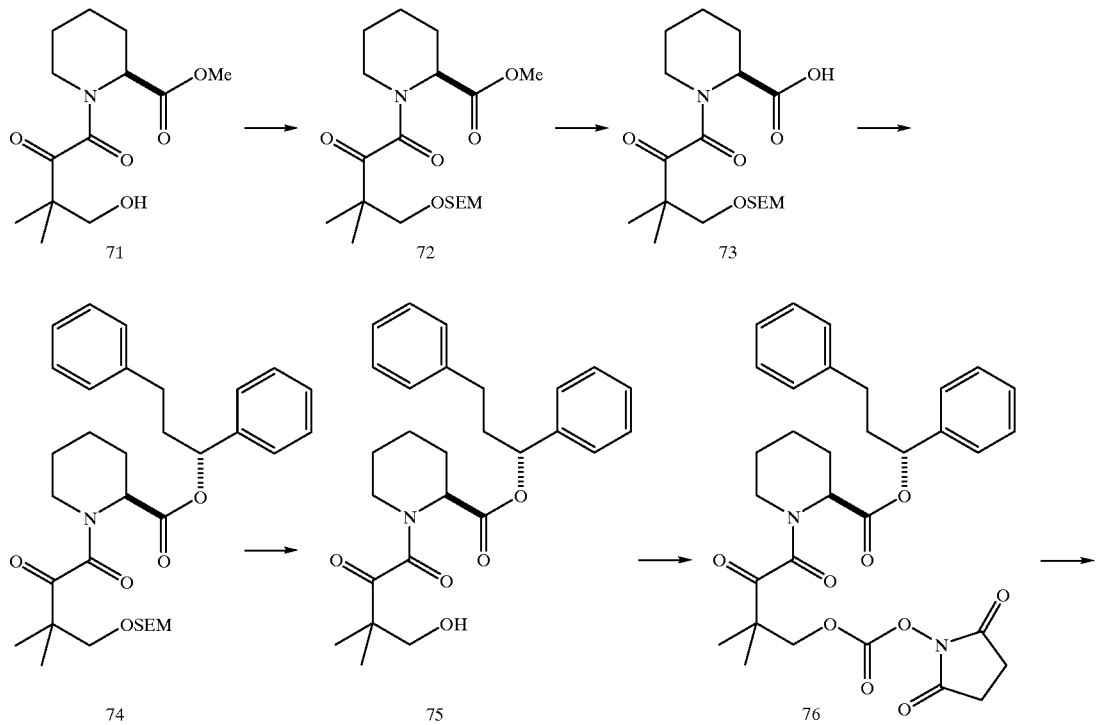

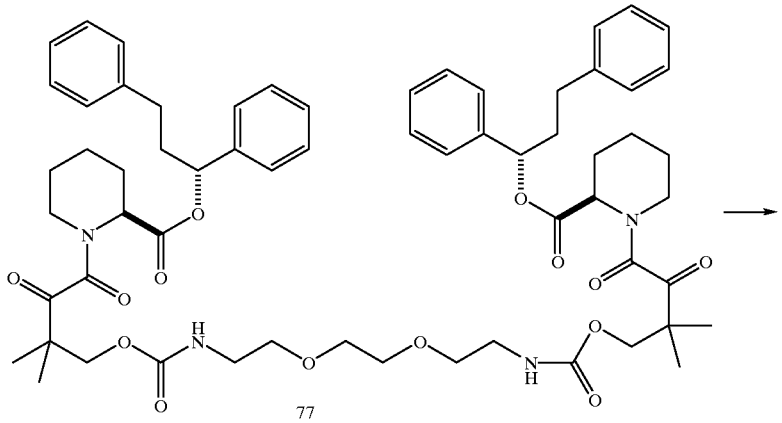

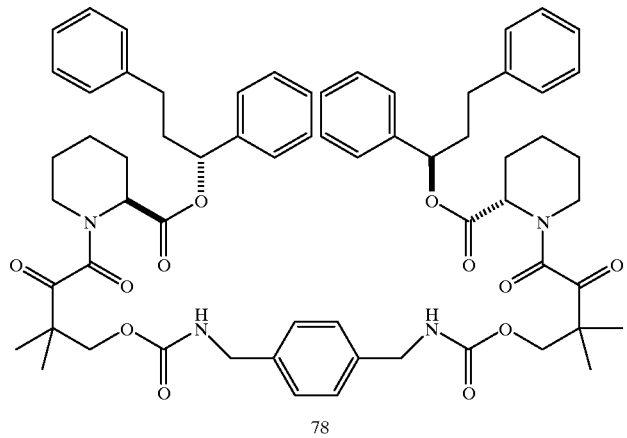

Synthetic Details

Methyl (2S)-1-(3,3-dimethyl-1,2-dioxo-4-hydroxy)butyl-2-piperidinecarboxylate, (71)

Prepared according to the procedure reported by D. A. Holt et al., *J. Am, Chem. Soc.* 1993, 115, 9925–9938 for the ethyl ester analog.

$^1$H NMR (CDCl$_3$) δ 5.25 (dist d, J=5.2 Hz, 1H), 3.78 (s, 3H), 3.59–3.71 (m, 2H), 3.49 (br d, J=13.8 Hz, 1H), 3.37 (t, J=6.4 Hz, 1H), 3.18 (td, J=12.9, 3.3 Hz, 1H), 2.32 (br d, J=14.0 Hz, 1H), 1.25–1.80 (m, 5H), 1.23 (s, 6H). MS (DCI/NaI) m/z 289 (M+NH$_4$), 272 (M+H).

Methyl (2S)-1-{3,3-dimethyl-1,2-dioxo-4-[2-(trimethylsilyl)ethoxy]methoxy}butyl-2-piperidinecarboxylate, (72)

A solution of methyl (2S)-1-(3,3-dimethyl-1,2-dioxo-4-hydroxy)butyl-2-piperidinecarboxylate, 71 (1.80 g, 6.6 mmol), N,N'-diisopropylethylamine (1.03 g, 8.0 mmol), and 2-(trimethylsilyl)ethoxymethyl chloride (1.33 g, 8.0 mmol) in dichloromethane (25 mL) was stirred at room temperature for 21.5 h. The solution was concentrated and the residue was chromatographed (silica-gel, hexanes-ethyl acetate 10:1 to 6:1 gradient) to give the title compound (2.60 g) as a colorless liquid.

$^1$H NMR (CDCl$_3$) δ 5.22 (br d, J=5.1 Hz, 1H), 4.62 (s, 2H), 3.73 (s, 3H), 3.49–3.71 (m, 5H), 3.14 (td, J=13.3, 3.4 Hz, 1H), 2.28 (br d, J=14.0 Hz, 1H), 1.18–1.77 (m, 5H), 1.30 (s, 3H), 1.27 (s, 3H), 0.84–0.94 (m, 2H), 0.00 (s, 9H). MS (FAB$^+$/NaI) m/z

(2S)-1-{3,3-Dimethyl-1,2-dioxo-4-[2-(trimethylsilyl)ethoxy]methoxy}butyl-2-piperidinecarboxylic acid, (73)

A mixture of methyl (2S)-1-{3,3-dimethyl-1,2-dioxo-4-[2-(trimethylsilyl)ethoxy]methoxy}butyl-2-piperidinecarboxylate, 72 (2.50 g, 6.2 mmol), 1N lithium hydroxide (9.3 mL) and methanol (10 mL) was stirred at 0° C. for 30 min and then at room temperature for 7 h. The mixture was acidified with 1N HCl, diluted with water, and extracted with dichloromethane. The organic extract was washed with water, dried over anhydrous sodium sulfate, and concentrated to give a colorless oil (2.11 g) which was used without further purification.

$^1$H NMR (CDCl$_3$) δ 10.25 (br s, 1H), 5.27 (d, J=4.9 Hz, 1H), 4.61 (s, 2H), 3.68 (dis. t, J=9.4, 9.9 Hz, 1H), 3.49–3.60 (m, 4H), 3.11–3.20 (m, 1H), 2.31 (br d, J=13.7 Hz, 1H), 1.36–1.79 (m, 5H), 1.29 (s, 3H), 1.27 (s, 3H), 0.91 (td, J=8.4, 3.0 Hz, 2H), 0.00 (s, 9H). $^{13}$C NMR (CDCl$_3$) δ 207.5, 176.9, 168.7, 96.4, 75.0, 66.6, 52.5, 48.8, 45.3, 27.7, 26.2, 23.9 (2C), 22.6, 19.5, 0.00. MS (FAB$^-$) m/z 386 (M–H)

(1R)-1,3-Diphenyl-1-propyl (2S)-1-{3,3-dimethyl-1,2-dioxo-4-[2-(trimethylsilyl)ethoxy]methoxy}butyl-2-piperidinecarboxylate, (74)

A solution of (2S)-1-{3,3-dimethyl-1,2-dioxo-4-[2-(trimethylsilyl)ethoxy] methoxy }butyl-2-piperidinecarboxylic acid, 73 (1.00 g, 2.6 mmol) and (1R)-1,3-diphenyl-1-propanol (0.72 g, 3.4 mmol) in dichloromethane (10 mL) was treated with N,N-dicyclohexylcarbodiimide (0.70 g, 3.4 mmol) and 4-dimethylaminopyridine (0.22 g, 1.8 mmol). The resulting suspension was stirred at room temperature under a nitrogen atmosphere for 17 h. The mixture was then diluted with a small amount of ethyl acetate, filtered, and concentrated, and the residue was subjected to column chromatography (silica-gel, hexanes-ethyl acetate 8:1) to afford the title compound (1.33 g) as a colorless oil $^1$H NMR (CDCl$_3$) δ 7.14–7.32 (m, 10H), 5.27–5.47 (m, 1H), 5.08 (br d, J=5.2 Hz, 1H), 4.59 (AB q, J$_{AB}$=6.8 Hz, 2H), 3.66 (dd, J=9.2, 8.6 Hz, 1H), 3.48–3.62 (m, 3H), 3.33 (br d, J=13.1 Hz, 1H), 2.70–2.92 (m, 5H), 2.00 (br d, J=11.5 Hz, 1H), 1.21–1.49 (m, 5H), 1.27 (s, 3H), 1.25 (s, 3H), 0.86–0.95 (m, 2H), 0.00 and −0.02 (2×s, 9H). MS (FAB$^+$/NaI) m/z 604 (M+Na). Exact Mass: Calc. (M+Na) for C$_{33}$H$_{47}$NSiO$_6$, 604.3070; found, 604.3073.

(1R)-1,3-Diphenyl-1-propyl (2S)-1-(3,3-dimethyl-1,2-dioxo-4-hydroxy)butyl-2-piperidinecarboxylate, (75)

A solution of (1R)-1,3-diphenyl-1-propyl (2S)-1-{3,3-dimethyl-1,2-dioxo-4-[2-(trimethylsilyl)ethoxy]methoxy }butyl-2-piperidinecarboxylate, 74 (0.75 g, 1.3 mmol) and 48 wt % HF (0.5 mL) in acetonitrile (25 mL) was stirred at room temperature for 4 h, and then partitioned between 10% aqueous sodium bicarbonate and ethyl acetate. The organic layer was decanted, washed with water, dried over anhydrous sodium sulfate, and concentrated, and the residue chromatographed (silica-gel, hexanes-ethyl acetate 4:1 to 2:1 gradient) to afford 75 (0.45 g) as a colorless oil).

$^1$H NMR (CDCl$_3$) δ 7.10–7.27 (m, 10H), 5.38–5.47 (m, 1H), 5.04 (br d, J=5.3 Hz, 1H), 3.47–3.621 (m, 3H), 3.29 (br d, J=13.9 Hz, 1H), 2.67–2.93 (m, 5H), 2.00 (br d, J=12.8 Hz, 1H), 1.17–1.57 (m, 5H), 1.15 (s, 3H), 1.14 (s, 3H). MS (FAB$^+$/NaI) m/z 474 (M+Na). Exact Mass: Calc. (M+Na) for C$_{25}$H$_{33}$NO$_5$, 474.2256; found, 474.2273.

(1R)-1,3-Diphenyl-1-propyl (2S)-1-[3,3-dimethyl-1,2-dioxo-4-(1-succinimidyloxycarbonyl)oxy]butyl-2-piperidinecarboxylate, (76)

A solution of (1R)-1,3-diphenyl-1-propyl (2S)-1-(3,3-dimethyl-1,2-dioxo-4-hydroxy)butyl-2-piperidinecarboxylate, 75 (223 mg, 0.49 mmol) in dichloromethane (13 mL) was treated with N,N-diisopropylethylamine (0.8 mL), and N,N'-disuccinimidyl carbonate (385 mg), and the mixture stirred at room temperature for 66 h. It was then washed with saturated sodium bicarbonate, dried over anhydrous sodium sulfate, and concentrated to afford a yellow oil (280 mg) which was used without further purification.

$^1$H NMR (C$_6$D$_6$) δ 7.11–7.32 (m, 10H), 5.56–5.65 (m, 1H), 5.36 (br d, J=5.1 Hz, 1H), 4.51 (d, J=10.5 Hz, 1H), 4.17 (d, J=10.5 Hz, 1H), 3.52 (br d, J=13.4 Hz, 1H), 2.71–3.11 (m, 5H), 1.99 (br d, J=14.4 Hz, 1H), 1.70 (br s, 4H), 1.01–1.38 (m, 11H). $^{13}$C NMR (C$_6$D$_6$) δ 205.4, 171.0, 169.7, 168.2, 153.5, 139.2 (139.0), 131.2, 130.2, 130.1, 129.8, 129.5, 129.2, 128.3 (128.2), 77.9, 76.9, 53.1, 48.4, 45.3, 41.9, 41.8, 27.7, 26.6 (2C), 26.3, 23.5, 22.5, 22.3. MS (FAB$^+$/NaI) m/z 615 (M+Na), 474, 434. Exact Mass: Calc. (M+Na) for C$_{32}$H$_{36}$N$_2$O$_9$, 615.2319; found, 615.2299.

2,2-(Ethylenedioxy)diethylamine N,N'-{2,2-dimethyl-3,4-dioxo-4-{(2S)-2-[(1R)-1,3-diphenylpropyloxycarbonyl]-1-piperidinyl}butylcarbamate, (77)

A solution of (1R)-1,3-diphenyl-1-propyl-(2S)-1-[3,3-dimethyl-1,2-dioxo-4-(1-succinimidyloxycarbonyl)oxy] butyl-2-piperidinecarboxylate, 76 (75 mg, 0.13 mmol) and N,N-diisopropylethylamine (66.3 μL) in acetonitrile (4 mL) was treated with 2,2'-(ethylenedioxy)diethylamine (9.3 μL), and the mixture stirred at room temperature for 21 h. The solvent was removed and the residue chromatographed (silica-gel, hexanes-ethyl acetate 1:3 to 1:2 gradient) to give the title compound (20 mg) as a colorless oil.

$^1$H NMR (CDCl$_3$) δ 7.10–7.55 (m, 20H), 5.48 (br dd, J=12.2, 6.1 Hz, 2H), 5.20–5.35 (br s, 2H), 5.09–5.18 (m, 2H), 4.22 (AB q, J$_{AB}$=10.6 Hz, 4H), 3.48–3.80 (m, 8H), 3.20–3.45 (m, 6H), 2.80–3.15 (m, 10H), 1.98–2.08 (m, 2H), 1.17–1.68 (m, 22H). $^{13}$C NMR (CDCl$_3$) δ 205.3, 170.1, 166.9, 156.6, 137.6, 137.3, 129.7 (2C), 128.9, 128.8, 127.1, 127.0, 76.9, 70.6, 70.4, (69.9), (60.8), (56.9), 51.6, 47.3, (47.2), 44.0, 41.2, 40.7, 40.5, (40.2), (39.0), (28.1), 26.8, 25.2, (24.7), 22.3, (22.2), 21.8, (21.4), 21.0, (20.8), 14.6. MS (FAB$^+$/NaI) m/z 1125 (M+Na).

p-Xylylenediamine N,N'-{2,2-dimethyl-3,4-dioxo-4-{(2S)-2-[(1R)-1,3-diphenylpropyloxycarbonyl]-1-piperidinyl}butylcarbamate, (78)

A solution of p-xylylenediamine in dimethylformamide (0.1 mM, 0.5 mL) was added dropwise, over a 30 min-period, to a solution of 76 (66 mg, 0.11 mmol) and triethylamine (46 μL) in acetonitrile (1 mL). The mixture was then partitioned between ethyl acetate and water, and the organic layer was decanted, washed with water, dried over anhydrous sodium sulfate, and concentrated to a yellow oil. Column chromatography (silica-gel, hexanes-ethyl acetate 1:1) afforded the title compound (33 mg) as a colorless oil.

$^1$H NMR (C$_6$D$_6$) δ 7.34–7.55 (m, 24H), 5.72–5.85 (m, 2H), 5.64–5.68 (m, 2H), 5.35–5.45 (m, 2H), 4.77 (AB q, J$_{AB}$=10.8 Hz, 4H), 4.46–4.57 (m, 4H), 3.64 (br d, J=12.2 Hz, 2H), 2.92–3.25 (m, 10H), 2.14 (br d, J=13.2 Hz, 2H), 1.20–1.75 (m, 22H). MS (FAB$^+$/NaI) m/z 1113 (M+Na).

Preparation of Bumped Monomers
Illustrative C-9 bumped monomers were prepared by the following scheme:
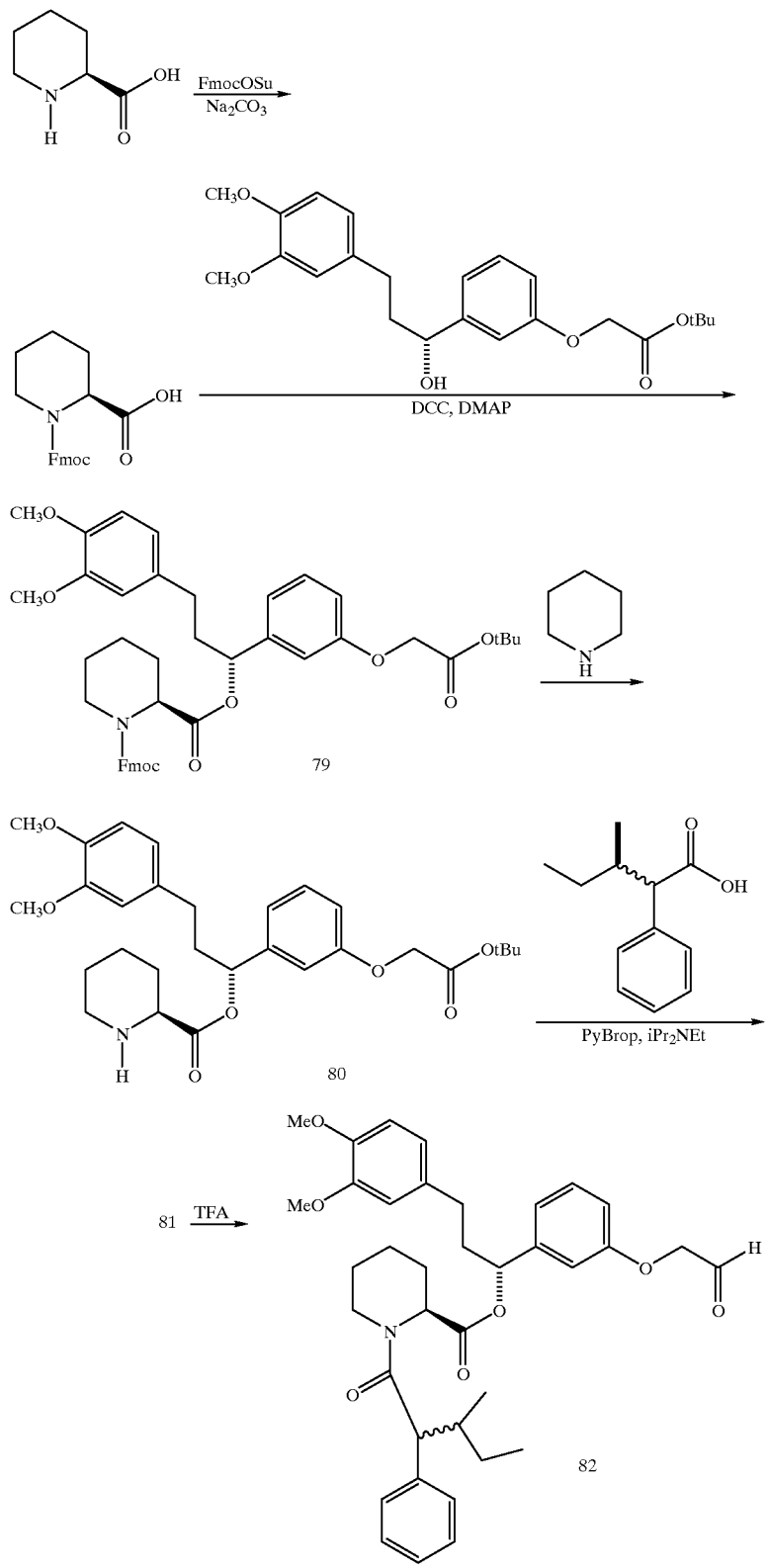

(1R)-3-(3,4-Dimethoxyphenyl)-1-[3-(t-butoxycarbonylmethoxy)phenyl]-1-propyl (2S)-1-(9-fluorenylmethoxycarbonyl)-2-piperidinecarboxylate (79)

A solution of (R) 1-(3-(tert-Butoxycarbonylmethoxy)phenyl)-3-(3,4-dimethoxyphenyl) propan-1-ol (13) (3.1 g, 7.7 mmol) in $CH_2Cl_2$ (40 mL) was treated with Fmoc pepicolic acid (3.0 g, 8.5 mmol) followed by 1,3-dicyclohexyl carbodiimide (DCC, 1.9 g, 9.2 mmol) and 4-(dimethylamino)pyridine (DMAP 560 mg, 4.6 mmol) under a nitrogen atmosphere. The resulting bright white suspension was allowed to stir overnight. The reaction mixture was then filtered, evaporated, and flash chromatographed (silica gel, 15%→20% EtOAc/hexanes) to afford 4.7 g (83%) of a white foam: $^1$H NMR (CDCl$_3$, 300 MHz) 7.73 (m, 2H), 7.59 (t, J=6.6 Hz, 1H), 7.16–7.49 (m, 6H). 6.94 (d, J=7.6 Hz, 1H), 6.89 (s, 1H), 6.72–6.82 (m, 2H), 6.62 (m, 2H), 5.76 (br s, 1H), 5.02 (d, J=3.7 Hz, 1H), 4.25–4.49 (m, 5H), 4.07–4.14 (m, 1H), 3.83 (s, 6H), 3.14 (t, J=11.1 Hz, 1H), 2.46–2.54 (m, 2H), 2.16–2.33 (m, 2H), 2.00–2.07 (m, 1H), 1.68–1.78 (m, 4H), 1.46 (s, 9H), 1.39–1.56 (m, 1H); $^{13}$C NMR (CDCl$_3$, 75 MHz) 174.50, 171.33 168.28, 158.48, 147.73, 144.30, 142.12, 133.90, 130.07, 128.07, 127.45, 125.48, 120.50, 120.35, 114.34, 113.66, 112.12, 111.74, 82.74, 76.82, 76.59, 68.20, 66.16, 56.32, 56.20, 47.63, 38.44, 31.98, 31.54, 28.42, 27.23, 25.18, 21.20.

(1R)-3-(3,4-Dimethoxyphenyl)-1-[3-(t-butoxycarbonylmethoxy)phenyl]-1-propyl (2S)-2-piperidinecarboxylate (80)

A solution of the above Fmoc protected compound (833 mg, 1.13 mmol) in $CH_2Cl_2$ (30 mL) was treated with piperidine (1.12 mL, 11.3 mmol) and the mixture was stirred at room temperature overnight. The reaction mixture was concentrated and flash chromatographed (silica gel, 50%→100% EtOAc/hexanes) to afford 569 mg (98%) of the amine as a white foam: $^1$H NMR (CDCl$_3$, 300 MHz) (single enantiomer, mixture of rotamers) 7.28 (t, J=7.9 Hz, 1H), 6.98 (d, J=7.7 Hz, 1H), 6.93 (s, 1H), 6.84 (m, 2H), 6.71 (d, J=8.3 Hz, 1H), 6.69 (s, 1H), 5.77 (dd, J=6.3, 6.8 Hz, 1H), 4.55 (s, 2H), 3.91 (s, 6H), 3.42 (m, 1H), 3.33 (s, 1H), 3.01 (m, 1H), 2.39–2.63 (m, 3H), 2.11–2.27 (m, 1H), 2.05–2.09 (m, 1H), 1.92 (m, 1H), 1.54 (s, 9H), 1.54–1.74 (m, 4H); $^{13}$C NMR (CDCl$_3$, 75 MHz) 173.42, 168.29, 158.34, 149.20, 147.64, 142.54, 134.06, 129.92, 120.49, 120.19, 114.11, 113.54, 111.99, 111.60, 82.74, 75.21, 66.05, 61.45, 56.30, 56.21, 48.57, 38.55, 31.63, 29.41, 28.44, 25.70, 22.56. MS(FAB): (M+Na)$^+$ 536.

(1R)-3-(3,4-Dimethoxyphenyl)-1-[3-(t-butoxycarbonylmethoxy)phenyl]-1-propyl (2S)-1-(1-oxo-2-phenyl-3-methyl-pentyl)-2-piperidinecarboxylate (81)

A solution of the above amine (484 mg, 0.94 mmol) in $CH_2Cl_2$ (10 mL) was treated with 3-methyl-2-phenyl valeric acid (362 mg, 1.9 mmol) followed by PyBroP (878 mg, 1.9 mmol) and diisopropylethyl amine (819 μL, 4.7 mmol) under a nitrogen atmosphere. The resulting solution was allowed to stir overnight. The reaction mixture was concentrated and flash chromatographed (silica gel, 10%→33% EtOAc/hexanes) to afford 380 mg (55%) of a white foam: $^1$H NMR (CDCl$_3$, 300 MHz) (single enantiomer, mixture of rotamers) 7.18–7.35 (m, 6H), 6.57–7.04 (m, 6H), 5.76–5.80 (m, 1H), 5.52–5.57 (m, 1H), 4.54 (s, 2H), 3.87 (s, 6H), 3.50–3.57 (m, 1H), 3.10 (t, J=13.3 Hz, 1H), 2.04–2.71 (m, 5H), 0.61–1.85 (m, 12H), 1.49 (s, 9H). HRMS(FAB): (M+Na)$^+$ calcd: 710.3669, found: 710.3664.

(1R)-3-(3,4-Dimethoxyphenyl)-1-[3-(hydroxycarbonylmethoxy)phenyl]-1-propyl (2S)-1-(1-oxo-2-phenyl-3-methyl-pentyl)-2-piperidinecarboxylate (82)

A solution of the above t-butyl ester (331 mg, 0.48 mmol) in $CH_2Cl_2$ (4 mL) was treated with trifluoroacetic acid (0.74 mL, 9.6 mmol) and the mixture was stirred at room temperature for 2 hours. The reaction mixture was diluted with toluene(50 mL) and concentrated and flash chromatographed (silica gel, 100% EtOAc) to afford 300 mg (100%) of the acid as a white solid: HRMS(FAB): (M+Na)$^+$ calcd: 654.3043, found: 654.3055.

Additional Synthetic Examples

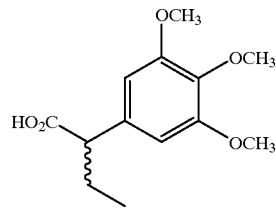

2R/S-(3,4,5-Trimethoxyphenyl)butyric acid

A solution of 3,4,5-trimethoxyphenylacetic acid (32.8 g, 145 mmol) in THF (200 mL) at 0° C. was treated with a 1N solution of sodium bis(trimethylsilyl)amide (325 mL, 325 mmol) followed 15 min later by addition of iodoethane (12.8 mL, 160 mmol). The reaction mixture was allowed to warm to room temperature and stir for 12 h after which time the reaction mixture was diluted with EtOAc (1.5 L) and poured onto a mixture of ice (500 g) and acidified to a pH of 3 by careful addition of 1N aqueous HCl solution. The aqueous phase was extracted with EtOAc (500 mL) which were then combined and washed with water (250 mL) followed by a saturated aqueous NaCl solution (100 mL). The organic extract was then dried over MgSO$_4$, filtered, evaporated, and chromatographed (silica gel, 2.5% HOAc/48.75% EtOAc/48.75% hexanes) to afford product (33.92 g, 92%): $^1$H NMR (CDCl$_3$, 300 MHz) 6.53 (s, 2 H), 3.85 (s, 6 H), 3.83 (s, 3 H), 3.38 (t, J=7.6 Hz, 1 H), 2.13–2.04 (m, 1 H), 1.84–1.75 (m, 1 H), 0.93 (t, J=7.4 Hz, 3 H); $^{13}$C NMR (CDCl$_3$, 75 MHz) 179.9, 153.7, 137.8, 134.3, 105.6, 61.2, 56.6, 53.9, 26.8, 12.5.

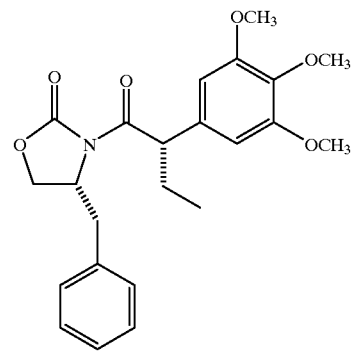

(4R-Benzyl-2-oxazolidinonyl) 2S-(3,4,5-Trimethoxyphenyl)butyrimide

A solution of 2R/S-(3,4,5-Trimethoxyphenyl)butyric acid (33.9 g, 133 mmol) in $CH_2Cl_2$ (350 mL) at room temperature was treated with thionyl chloride (50.0 mL, 685 mmol) and allowed to stir for 16 h. The reaction mixture was then concentrated and dissolved in THF (250 mL) and added to a solution of the sodium oxazolidinonide prepared by addition of n-BuLi (108 mL of 1.6N hexanes solution, 172.8 mmol) to a THF (600 mL) solution of R-4-benzyl-2-oxazolidinone (29.46 g, 166.3 mmol) at −78° C. which was allowed to warm to 0° C. and stir for 30 min. After addition of the chloride, the reaction mixture was allowed to warm to room temperature and stir for 1.5 h after which time was poured onto a saturated aqueous NH₄Cl solution (1 L) and the resulting slurry extracted with CH₂Cl₂ (3×1 L). The combined organic extracts were washed with a 1N aqueous NaOH solution (1 L) followed by water (1 L) and a saturated aqueous NaCl solution (750 mL). The organic extract was then dried over MgSO₄, filtered, evaporated, and chromatographed (silica gel, 5% EtOAc/5% hexanes/90% CH₂Cl₂) to afford product (12.65 g, 23%) as the less polar diastereomer.

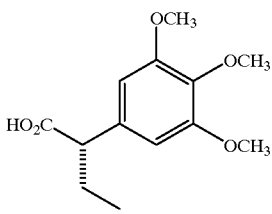

2S-(3,4,5-Trimethoxyphenyl)butyric acid

A solution of (4R-benzyl-2-oxazolidinonyl) 2S-(3,4,5-Trimethoxyphenyl)butyrimide (12.6 g, 30.6 mmol) in THF (75 mL) at 0° C. was slowly added to a slurry containing LiOH monohydrate (12.84, 306 mmol) and hydrogen peroxide (34.7 mL of a 30% aqueous solution, 306 mmol) in a THF/water (2:1) solution at 0° C. The reaction mixture was allowed to stir for 30 min after which time EtOAC (1 L) was added and the solution slowly acidified to a pH of 3 with a 1N aqueous solution of HCl. The organic phase was washed with water (500 mL) followed by a saturated aqueous NaCl solution (250 mL), then dried over MgSO₄, filtered, evaporated, and chromatographed (silica gel, 2.5% HOAc/48.75% EtOAc/48.75% hexanes) to afford product (5.99 g, 77%).

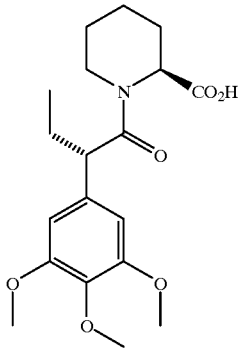

N-2S-(3,4,5-Trimethoxyphenyl)butyryl -2S-piperdinecarboxylic acid

A solution of 2S-(3,4,5-trimethoxyphenyl)butyric acid (5.99 g, 23.6 mmol) in CH₂Cl₂ (175 mL) at room temperature was treated with methyl 2S-piperdinecarboxylate (4.66 g, 26 mmol) followed by triethylamine (10.9 mL, 78 mmol) and 2-chloro-1-methylpyridinium iodide (8.95 g 35 mmol). The reaction mixture was stirred for 2 h after which time it was concentrated and chromatographed (silica gel, 50% EtOAc/hexanes) to afford product (6.72 g, 75%).

A solution of the methyl ester (7.39 g, 19.5 mmol) in a MeOH/water solution (1.5 L/15 mL) at room temperature was treated with LiOH monohydrate (8.20 g, 195.4 mmol). The reaction mixture was stirred for 4 h, diluted with EtOAc (1 L) then poured onto a mixture of ice (200 g) and a 1N aqueous solution of HCl (225 mL). The organic portion was then washed with water (300 mL) followed by a saturated aqueous NaCl solution (250 mL), then dried over MgSO₄, filtered, and evaporated to a powder which was recrystallized from EtOAc to afford product (6.42 g, 90%) as a white crystalline solid: ¹H NMR (CDCl₃, 300 MHz) 8.17 (br s, 1 H), 6.43 (s, 2 H), 5.36 (d, J=3.9 Hz, 1 H), 4.70 (d, J=5.4 Hz, 1 H), 3.84–3.81 (m, 9H), 3.58 (t, J=6.9 Hz, 1 H), 2.85 (t, J=12.0 Hz, 1 H), 2.27 (t, J=13.5 Hz, 1 H), 2.12–2.05 (m, 1 H), 1.78–1.52 (m, 4 H), 1.48–1.30 (m, 2 H), 0.92 (t, J=7.3 Hz, 3 H); ¹³C NMR (CDCl₃, 75 MHz) 174.4, 172.4, 152.1, 135.6, 133.9, 103.7, 59.6, 55.1, 51.0, 49.9, 42.4, 42.4, 27.1, 25.1, 23.9, 19.5, 11.3; MS (ES+): (M+H)⁺ 366; (ES-): (M-H)⁻ 364.

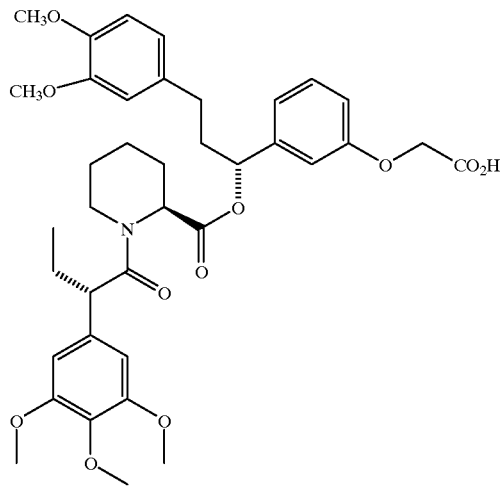

A solution of (R)-1-(3-(tert-butoxycarbonylmethoxy) phenyl)-3-(3,4-dimethoxyphenyl)propan-1-ol (13) (220 mg, 0.547 mmol) in CH₂Cl₂ (0.5 mL) at 0° C. was treated with (2S)-1-((3,4,5-trimethoxyphenyl)butyryl)-2-piperdinecarboxylic acid (210 mg, 0.574 mmol) followed by 4-(dimethylamino)-pyridine (2 mg) and 1,3-dicyclohexylcarbodiimide (113 mg, 0.574 mmol). The resulting suspension was allowed to warm to room temperature and stir 16 h after which time it was diluted with EtOAc (3 mL) and filtered through a plug of Celite. The evaporated residue was chromatographed (silica gel, 40%→50% EtOAc/hexanes) to afford (1R)-1-(3-(tert-butoxycarbonylmethoxy)phenyl)-3-(3,4-dimethoxyphenyl) propan-1-yl (2S)-1-((2S)-(3,4,5-trimethoxyphenyl)butyryl)-2-piperdine carboxylate (295 mg, 72%) as a colorless foam: TLC (EtOAc/hexanes, 2:3) Rf=0.20; MS (ES+): (M+H)⁺ 750, (M+Na)⁺ 772.

A solution of the above tert-butyl ester (250 mg, 0.362 mmol) in CH₂Cl₂ (10.0 mL) was cooled to 0° C. and treated with a steam of hydrogen chloride for 10 min. The reaction mixture was allowed to warm to room temperature and stir for 2 h after this time the reaction was evaporated for a solid white foam (245 mg, 90%): MS (ES+): (M+NH₄)⁺ 711, (M+Na)⁺ 716; (ES-): (M-H)⁻ 692.

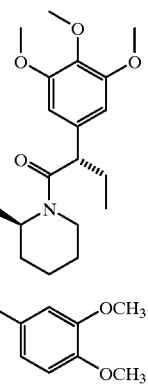

AP1903

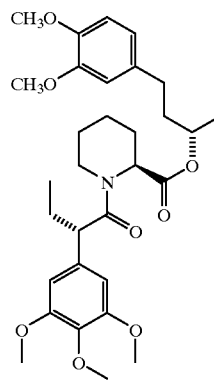

A solution of AP1867 (8.2 g, 11.82 mmol) in CH$_2$Cl$_2$ (100 ML) at 0° C. was treated sequentially with benzotriazol-1-yloxytris-(dimethylamino)phosphonium hexafluorophosphate (7.3 g 14.0 mmol), duisopropylethylamine (5.50 mL, 31.6 mmol), and ethylenediamine (395 uL, 5.91 mmol). The reaction mixture was allowed to stir at room temperature for 16 h after which time was diluted with EtOAc (150 mL) and washed with water (3×50 mL) followed by a saturated aqueous NaCl solution (25 mL). The organic solution was dried over MgSO4, filtered, and evaporated to afford a residue which was chromatographed (silica gel, EtOAc) to afford product. The product was then dissolved in MeOH (10 mL) and water added until the solution became turbid. Freezing of the aqueous methanolic solution (dry ice/acetone bath) followed by lyophilization at 100 mtorr afforded AP1903 (5.49 g, 61%) as a white powder: MS (ES+): (M+Na)$^+$ 1434; (ES−): (M−H)$^-$ 1410.

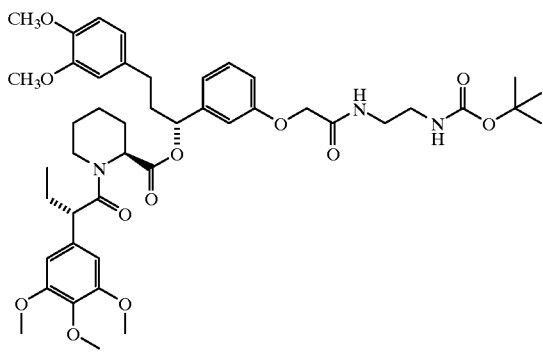

The acid AP 1867 (245 mg, 0.353 mmol) was dissolved in CH$_2$Cl$_2$ (1.0 mL), cooled to 0° C., and treated 4-(dimethylamino)-pyridine (2 mg) followed by 1,3-dicyclohexylcarbodiimide (77 mg, 0.371 mmol). The reaction mixture was allowed to stir for 5 min after which time tert-butyl N-(2-aminoethyl)-carbamate (61 uL, 0.388 mmol) was added. The resulting suspension was allowed to stir for 16 h after which time it was diluted with EtOAc (3 mL), filtered through a plug of Celite, evaporated, and chromatographed (silica gel, EtOAc) to afford product (266 mg, 90%) as a colorless foam: TLC (EtOAc) Rf=0.36; MS (ES+): (M+H)$^+$ 836, (M+Na)$^+$ 858.

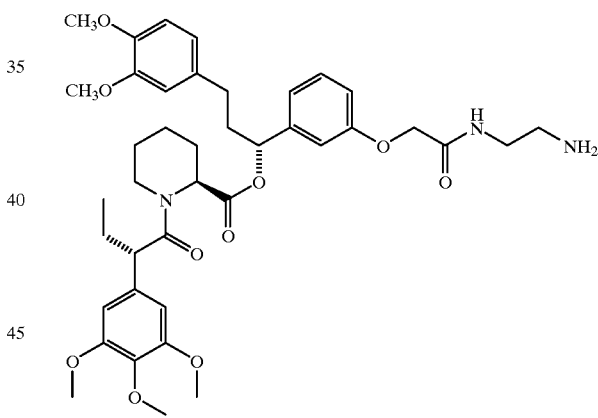

A solution of the above tert-butyl carbamate (266 mg, 0.318 mmol) in CH$_2$Cl$_2$ (10.0 mL) was cooled to 0° C. and treated with a steam of hydrogen chloride for 10 min. The reaction mixture was allowed to warm to room temperature and stir for 2 h after which time was evaporated to afford a solid white foam which was partitioned between CH$_2$Cl$_2$ (15 mL) and a saturated aqueous NaHCO$_3$ solution (10 mL). The layers were separated and the aqueous layer washed with CH$_2$Cl$_2$ (5 mL) and the combined organic extracts washed with a saturated aqueous NaCl solution (10 mL) then dried over Na$_2$SO$_4$, filtered, and evaporated to afford product (203 mg, 87%) as a colorless sticky foam: MS (ES+): (M+H)$^+$ 736.

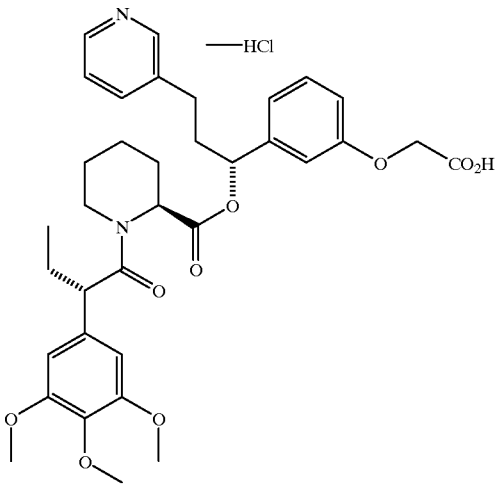

(1R)-1-(3-(Carboxymetboxy)phenyl)-3-(3-pyridyl)-1-propyl (2S)-1-((2S)-(3,4,5-trimethoxyphenyl)butyryl)-2-piperdinecarboxylate hydrochloride (AP14252)

diluted with EtOAc (3 mL) and filtered through a plug of Celite. The evaporated residue was chromatographed (silica gel, EtOAc) to afford product (303 mg, 84%) as a colorless foam: TLC (EtOAc) Rf=0.44; IR (neat) 2940, 1750, 1640, 1590, 1455, 1240, 1155 cm$^{-1}$; MS (ES+): (M+Na)$^+$ 691.

A solution of the above tert-butyl ester (250 mg, 0.362 mmol) in CH$_2$Cl$_2$ (10.0 mL) was cooled to 0° C. and treated with a steam of hydrogen chloride for 10 min. The reaction mixture was allowed to warm to room temperature and stir for 2 h. After this time the reaction was evaporated for a solid white foam: MS (ES+): (M+H)$^+$ 635; (ES-): (M-H)$^-$ 633.

The acid hydrochloride AP14252 was dissolved in CH$_2$Cl$_2$ (1.0 mL), cooled to 0° C., and treated with triethylamine (48 uL, 0.362 mmol), 4-(dimethylamino)-pyridine (2 mg), and 1,3-dicyclohexylcarbodiimide (90 mg, 0.434 mmol). The reaction mixture was allowed to stir for 5 min after which time a CH$_2$Cl$_2$ solution (100 uL) containing ethylenediamine (9.7 uL, 0.145 mmol) was added. The resulting suspension was allowed to warm to room tempera-

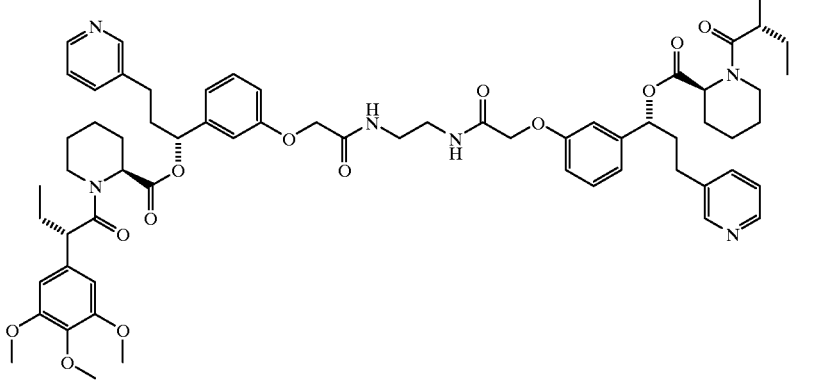

AP14290

A solution of (R)-1-(3-(tert-butoxycarbonylmethoxy)phenyl)-3-(3-pyridyl)propan-1-ol (21) (179 mg, 0.521 mmol) in CH$_2$Cl$_2$ (0.5 mL) at 0° C. was treated with (2S)-1-((2S)-(3,4,5-trimethoxyphenyl)butyryl)-2-piperdinecarboxylic acid (200 mg, 0.547 mmol) followed by 4-(dimethylamino)-pyridine (2 mg) and 1,3-dicyclohexylcarbodiimide (113 mg, 0.547 mmol). The resulting bright yellow suspension was allowed to warm to room temperature and stir for 16 h after which time it was ture and stir for 16 h after which time it was diluted with EtOAc (3 mL), filtered through a plug of Celite, evaporated, and chromatographed (silica gel, 2"×0.5" column, 10% MeOH/EtOAc) to afford product (102 mg, 54% from tert-butyl ester) as a colorless foam: TLC (MeOH/EtOAc, 5:95) Rf=0.28; IR (neat) 3345, 2940, 1740, 1680, 1650, 1540, 1505, 1455, 1425, 1245, 1130, 1015 cm$^{-1}$; MS (ES+): (M+H)$^+$ 1293.

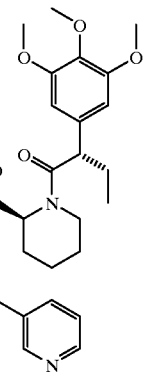

AP14283

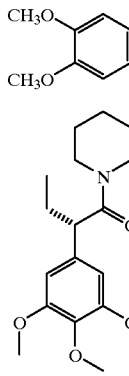

The acid (1R)-1-(3-(carboxymethoxy)phenyl)-3-(3-pyridyl)-1-propyl (2S)-1-((2S)-(3,4,5-trimethoxyphenyl) butyryl)-2-piperdinecarboxylate hydrochloride (AP14252) (28.5 mg, 0.0425 mmol) was dissolved in $CH_2Cl_2$ (0.5 mL), cooled to 0° C., and treated with a $CH_2Cl_2$ solution (100 uL) containing triethylamnine (5.6 uL, 0.0425 mmol) followed by 4-(dimethylamino)-pyridine (catalytic amount) and 1,3-dicyclohexylcarbodiimide (9.1 mg, 0.0442 mmol). The reaction mixture was allowed to stir for 5 min after which time the solid amine (25 mg, 0.034 mmol) was added. The resulting suspension was allowed to warm to room temperature and stir for 16 h after which time was diluted with EtOAc (3 mL), filtered through a plug of Celite, evaporated, and chromatographed (silica gel, 5→10% MeOH/EtOAc) to afford product (28 mg, 61%) as a colorless foam: TLC (MeOH/CHCl$_3$, 1:9) Rf=0.28; IR (neat) 3445, 2940, 1740, 1675, 1645, 1590, 1515, 1455, 1420, 1240, 1130, 1015 cm$^{-1}$; MS (ES+): (M+H)$^+$ 1352.

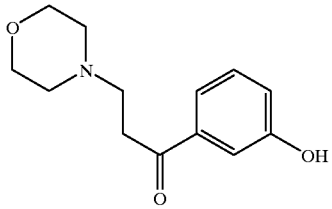

1-(3-Hydroxyphenyl)-3-(1-morpholino)propan-1-one

A solution of morpholine (1.0 mL, 11.5 mmol) in EtOH (10 mL) was treated with 3-hydroxyacetaphenone (1.56 g, 11.5 mmol) and paraformaldehyde (340 mg, 11.5 mmol) followed by acetic acid (1.3 mL, 23 mmol). The resulting mixture was heated at reflux for 16 h then cooled and evaporated. The residue was then diluted with a 5% aqueous HCl solution (10 mL) then washed with diethyl ether (2×10 mL) followed by neutralization by addition of solid NaHCO$_3$. The neutralized aqueous solution was extracted with diethyl ether (2×10 mL) which was then dried over MgSO$_4$, filtered, and concentrated to a residue. The residue was chromatographed (silica gel, 5% MeOH/CH$_2$Cl$_2$) to afford product (680 mg, 25%) as a brownish oil: TLC (MeOH/CH$_2$Cl$_2$, 5:95) Rf=0.22; IR (neat) 2960, 2855, 1685, 1585, 1450, 1360, 1275, 1115, 995, 865 cm$^{-1}$; $^1$H NMR (CDCl$_3$, 300 MHz) 7.48 (d, J=7.8 Hz, 1 H), 7.42 (t, J=2.0 Hz, 1 H), 7.32 (t, J=7.9 Hz, 1 H),7.05 (m, 1 H), 3.75 (t, J=4.7 Hz, 4 H), 3.25 (t, J=7.3 Hz, 2 H), 2.87 (t, J=7.3 Hz, 2 H), 2.57 (t, J=4.5 Hz, 4 H),; MS (ES–): (M–H)$^-$ 234.

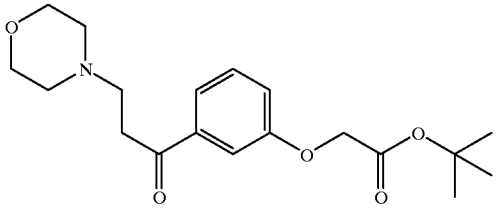

1-(3-(tert-Butoxycarbonylmethoxy)phenyl)-3-(1-morpholino)propan-1-one

A 60% mineral oil suspension of NaH (1.97 g, 49 mmol) in anhydrous DMF (20 mL) was cooled to 0° C. in an ice bath and a DMF solution (10 mL) of 1-(3-Hydroxyphenyl)-3-(1-morpholino)propan-1-one (10.5 g, 45 mmol) added. The resulting yellow solution was stirred for 15 min followed by addition of tert-butylbromoacetate (7.26 mL, 49 mmol). The reaction mixture was stirred at 0° C. for 15 min, allowed to warm to room temperature, and partitioned between EtOAc (50 mL) and water (150 mL). The aqueous portion was washed with EtOAc (2×50 mL) and the combined organic extracts washed with a saturated aqueous NaCl solution (2×50 mL), dried over Na$_2$SO$_4$, filtered, evaporated, and flash chromatographed (silica gel, 1% MeOH/EtOAc) to afford product (10.5 g, 67%) as an oil: TLC (MeOH/CH$_2$Cl$_2$, 5:95) Rf=0.39; IR (neat) 2975, 1750, 1685, 1585, 1445, 1370, 1225, 1155, 1120 cm$^{-1}$; $^1$H NMR (CDCl$_3$, 300 MHz) 7.57 (d, J=7.7 Hz, 1 H), 7.46 (s, 1 H), 7.38 (t, J=8.0 Hz, 1 H), 7.13 (d, J=8.2 Hz, 1 H), 4.57 (s, 2H), 3.71 (t, J=4.7 Hz, 4 H), 3.15 (t, J=7.3 Hz, 2 H), 2.82 (t, J=7.3 Hz, 2 H), 2.50 (t, J=4.6 Hz, 4 H), 1.49 (s, 9H); MS (ES+): (M+H)$^+$ 350.

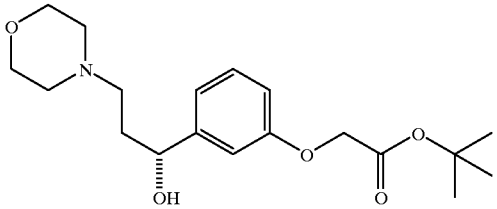

1R-(3-(tert-Butoxycarbonylmethoxy)phenyl)-3-(1-morpholino)propan-1-ol

A solution of 1-(3-(tert-butoxycarbonylmethoxy)phenyl)-3-(1-morpholino)propan-1-one (1.0 g, 2.86 mmol) in THF (5 mL) at −78° C. was treated with a solution of (+)-β-chlorodiisopinocamphenylborane (2.76 g, 8.59 mmol) in THF (10 mL) at −78° C. The resulting mixture was allowed to stand in a −20° C. freezer for 48 h after which time the mixture was evaporated and treated with diethyl ether (40 mL) followed by diethanolamine (5 mL). The viscous mixture was allowed to stir at room temperature for 4 h followed by filtration through a pad of Celite with the aid of ethyl acetate. The cloudy filtrate was evaporated and flash chromatographed (silica gel, 5% MeOH/EtOAc) to afford 270 mg (27%) of an oil that solidified to a waxy solid on standing: TLC (MeOH/CH$_2$Cl$_2$, 5:95) Rf=0.33; IR (neat) 2955, 1750, 1585, 1455, 1370, 1225, 1155, 1120, 1075 cm$^{-1}$; $^1$H NMR (CDCl$_3$, 300 MHz) 7.57 (d, J=7.9 Hz, 1 H), 6.97 (m, 2 H), 6.78 (d, J=8.1 Hz, 1 H), 4.91 (t, J=5.7 Hz, 1 H), 4.52 (s, 2H), 3.75 (t, J=4.6 Hz, 4 H), 2.70–2.40 (m, 6 H), 1.85 (m, 2 H), 1.49 (s, 9H); MS (ES+): (M+H)$^+$ 352.

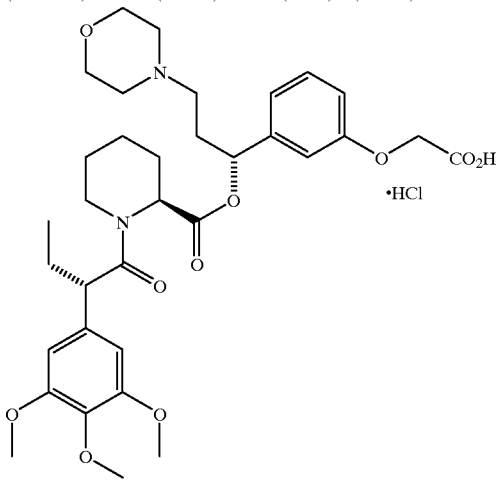

(1R)-1-(3-(carboxymethoxy)phenyl)-3-(morpholino)-1-propyl (2S)-1-((2S)-(3,4,5-trimethoxyphenyl)butyryl)-2-piperdine carboxylate (AP14246)

A solution of (R)-1-(3-(tert-butoxycarbonylmethoxy) phenyl)-3-(1-morpholino)propan-1-ol (96 mg, 0.274 mmol) in CH$_2$Cl$_2$ (2.0 mL) at 0° C. was treated with (2S)-1-((2S)-(3,4,5-trimethoxyphenyl)butyryl)-2-piperdinecarboxylic acid (100 mg, 0.274 mmol) followed by 4-(dimethylamino)-pyridine (2 mg) and 1,3-dicyclohexylcarbodiimide (59 mg, 0.287 mmol). The resulting suspension was allowed to warm to room temperature and stir 16 h after which time was diluted with EtOAc (5 mL) and filtered through a plug of Celite. The evaporated residue was chromatographed (silica gel, 3% MeOH/EtOAc) to afford product (154 mg, 81%) as a colorless foam: TLC (MeOH/CHCl$_3$, 5:95) Rf=0.28; IR (neat) 2940, 1750, 1645, 1590, 1455, 1245, 1155, 1130 cm$^{-1}$; MS (ES+): (M+H)$^+$ 699.

A solution of the above tert-butyl ester in CH$_2$Cl$_2$ (10.0 mL) was cooled to 0° C. and treated with a steam of hydrogen chloride for 10 min. The reaction mixture was allowed to warm to room temperature and stir for 2 h, after this time the reaction was evaporated for a solid white foam: MS (ES+): (M+H)$^+$ 643, (ES−): (M−H)$^-$ 641.

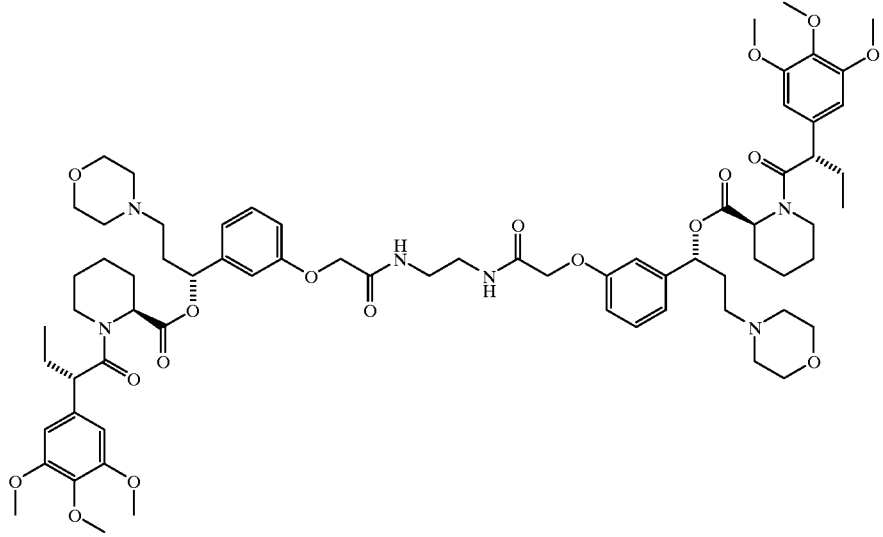

Hz, 4 H), 3.25 (t, J=7.3 Hz, 2 H), 2.87 (t, J=7.3 Hz, 2 H), 2.57 The acid hydrochloride AP14246 (50.6 mg 0.0745 mmol) was dissolved in $CH_2Cl_2$ (0.25 mL), cooled to 0° C., and treated with a $CH_2Cl_2$ solution (100 uL) containing triethylamine (9.8 uL, 0.0745 mmol) followed by 4-(dimethylamino)-pyridine (catalytic amount) and 1,3-dicyclohexylcarbodiimide (18.4 mg, 0.0894 mmol). The reaction mixture was allowed to stir for 5 min after which time a $CH_2Cl_2$ solution (100 uL) containing ethylenediamine (2.0 uL, 0.0298 mmol) was added. The resulting suspension was allowed to warm to room temperature then diluted with EtOAc (3 mL), filtered through a plug of Celite, evaporated, and chromatographed (silica gel, 2"×0.5" column, 20% MeOH/EtOAc) to afford product (25 mg, 64%) as a colorless foam: TLC (MeOH/EtOAc, 1:4) Rf=0.19; IR (neat) 2940, 1730, 1680, 1650, 1590, 1455, 1245, 1130 $cm^{-1}$; MS (ES+): $(M+H)^+$ 1310.

The acid hydrochloride, (1R)-1-(3-(carboxymethoxy)phenyl)-3-(morpholino)-1-propyl (2S)-1-((2S)-(3,4,5-trimethoxyphenyl)butyryl)-2-piperdinecarboxylate hydrochloride (AP14246), (100 mg mg, 0.147 mmol) was dissolved in $CH_2Cl_2$ (0.5 mL), cooled to 0° C., and treated with triethylamine (20 uL, 0.147 mmol) followed by 4-(dimethylamino)-pyridine (2 mg) and 1,3-dicyclohexylcarbodiimide (33 mg, 0.162 mmol). The reaction mixture was allowed to stir for 5 min after which time the solid amine was added (108 mg, 0.147 mmol) was added. The resulting suspension was allowed to stir overnight (16 h) then diluted with EtOAc (3 mL), filtered through a plug of Celite, evaporated, and chromatographed (silica gel, 5→10% MeOH/EtOAc) to afford product (170 mg, 85%) as a colorless foam: TLC (MeOH/EtOAc, 5:95) Rf=0.19; IR (neat) 3355, 2940, 1740, 1670, 1645, 1590, 1515, 1240, 1130, 1020 $cm^{-1}$; MS (ES+): $(M+H)^+$ 1361.

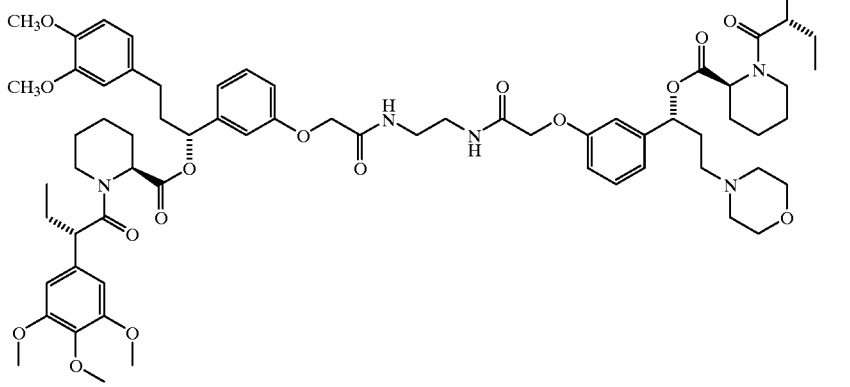

50

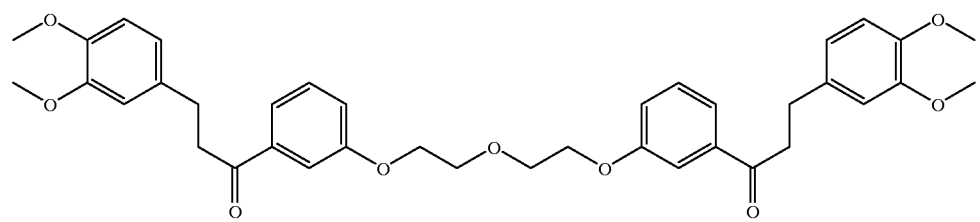

2-[1-(3-(3,4-Dimethoxyphenyl)propan-1-one)-3'-phenoxy] ethyl ether

A 60% mineral oil suspension of NaH (1.40 g, 3.49 mmol) in anhydrous DMF (25 mL) was cooled to 0° C. in an ice bath and solid 3-(3,4-dimethoxyphenyl)-1-(3-hydroxyphenyl)propan-1-one (10 g, 3.49 mmol) added portionwise. The resulting yellow solution was stirred for 15 min followed by addition of 2-iodoethyl ether (5.42 g, 1.02 mmol). The reaction mixture was stirred at 0° C. for 15 min and allowed to warm to room temperature and stir for 16 h. After this time the reaction mixture was partitioned between EtOAc (200 mL) and water (250 mL). The organic layer was washed with a saturated aqueous NaCl solution (3×200 mL), dried over $MgSO_4$, filtered, evaporated, and flash chromatographed (silica gel, 40→50→80% EtOAc/hexanes) to afford product (6.76 g, 63%) of a clear yellowish oil: TLC (ethyl acetate/hexanes, 1:1) Rf=0.28 ; IR (neat) 2935, 1685, 1515, 1460, 1260, 1140, 1030 $cm^{-1}$; $^1H$ NMR ($CDCl_3$, 300 MHz) 7.54–7.36 (m, 2 H), 7.33 (t, J=7.9 Hz, 1 H), 7.11 (d, J=8.1 Hz, 1 H), 6.81–6.77 (m, 3 H), 4.19 (t, J=4.1 Hz, 2 H), 3.94 (t, J=4.4 Hz, 2 H), 3.86 (s, 3 H), 3.84 (s, 3 H), 2.45 (t, J=7.3 Hz, 2 H), 3.00 (t, J=7.5 Hz, 2 H),; $^{13}C$ NMR ($CDCl_3$, 75 MHz) 199.6, 159.6, 149.5, 148.0, 138.8, 134.5, 130.1, 121.4, 120.8, 120.6, 113.8, 112.5, 112.0, 70.4, 68.3, 56.5, 56.4, 41.3, 30.4; MS (ES+): $(M+H)^+$ 643, $(M+Na)^+$ 665.

2-[1-(3-(3,4-Dimethoxyphenyl)propan-1-ol)-3'-phenoxy] ethyl ether

A solution of 2-[1-(3-(3,4-Dimethoxyphenyl)propan-1-one)-3'-phenoxy] ethyl ether (2.70 g, 4.20 mmol) in THF (10 mL) at −20° C. was treated with a solution of (+)-β-chlorodiisopinocamphenylborane (4.04 g, 12.6 mmol) in THF (10 mL) at −20° C. The resulting mixture was allowed to stand in a −20° C. freezer for 72 h after which time the mixture was evaporated and treated with diethyl ether (300 mL) followed by diethanolamine (10 mL). The viscous mixture was allowed to stir at room temperature for 6 h followed by filtration through a pad of Celite with the aid of ethyl acetate. The cloudy filtrate was evaporated and flash chromatographed (silica gel, 50→80→100% EtOAc/hexanes) to afford product (1.25 g, 46%) as a solid material: TLC (EtOAc/hexanes, 3:1) Rf=0.22; IR (neat) 3505, 2935, 1590, 1515, 1451, 1260, 1140, 1030 $cm^{-1}$; $^1H$ NMR ($CDCl_3$, 300 MHz) 7.26–7.20 (m, 1 H), 6.92–6.70 (m, 6 H), 4.64–4.60 (m, 1 H), 4.15 (t, J=4.4 Hz, 2 H), 3.92 (t, J=5.0 Hz, 2 H), 3.84 (s, 6 H), 2.73–2.54 (m, 2 H), 2.13–1.91 (m, 2 H); $^{13}C$ NMR ($CDCl_3$, 75 MHz) 159.4, 149.3, 147.6, 146.8, 134.8, 129.9, 120.6, 118.9, 114.0, 112.8, 112.3, 111.8, 74.1, 70.4, 67.9, 56.3, 56.2, 41.0, 32.0; MS (ES+): $(M+NH_4)^+$ 664, $(M+Na)^+$ 669.

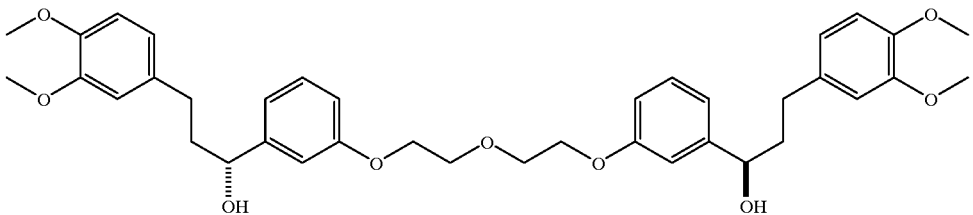

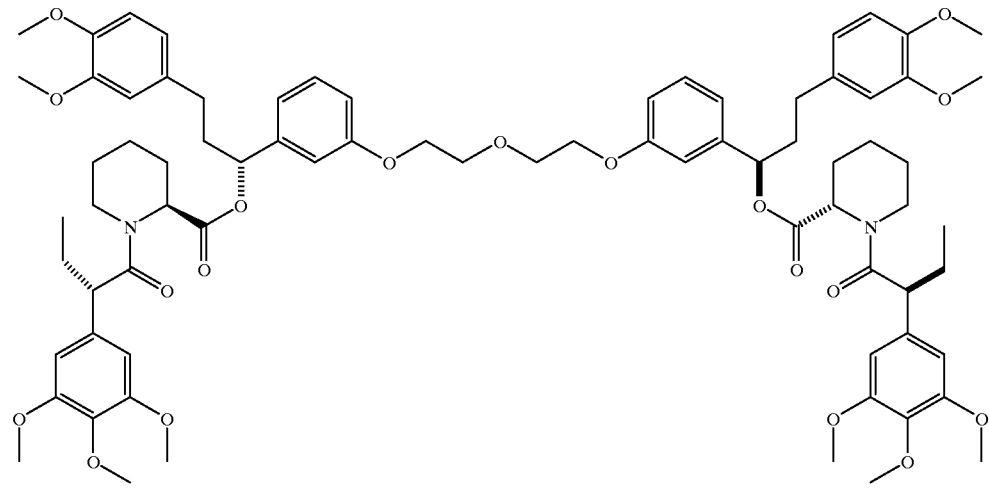

A solution of 2-[1-(3-(3,4-Dimethoxyphenyl)propan-1-ol)-3'-phenoxy]ethyl ether (100 mg, 0.155 mmol) in CH$_2$Cl$_2$ (2.0 mL) at 0° C. was treated with (2S)-1-((2S)-(3,4,5-trimethoxyphenyl)butyryl)-2-piperdinecarboxylic acid (181 mg, 0.495 mmol) followed by 4-(dimethylamino)-pyridine (2 mg) and 1,3-dicyclohexylcarbodiimide (102 mg, 0.495 mmol). The resulting bright yellow suspension was allowed to warm to room temperature and stir for 16 h after which time was diluted with EtOAc (5 mL) and filtered through a plug of Celite. The evaporated residue was chromatographed (silica gel, 5% EtOAc/hexanes) to afford product (101 mg, 49%) as a colorless foam: TLC (MeOH/CHCl$_3$, 5:95) Rf=0.38; IR (neat) 2940, 1740, 1645, 1590, 1515, 1455, 1240, 1130, 1030 cm$^{-1}$; MS (ES+): (M+NH$_4$)$^+$ 1358, (M+Na)$^+$ 1363.

3.84 (m, 3 H), 3.82 (m, 3 H), 3.24 (t, J=7.3 Hz, 1 H), 2.98 (t, J=7.8 Hz, 1 H); $^{13}$C NMR (CDCl$_3$, 75 MHz) 199.6, 173.6, 158.2, 149.3, 147.9, 138.8, 134.2, 130.3, 122.4, 120.7, 120.4, 113.7, 112.4, 112.0, 65.2, 56.4, 56.3, 41.1, 30.2; MS (ES+): (M+H)$^+$ 345, (M+Na)$^+$ 367; (ES−): (M−H)$^-$ 343.

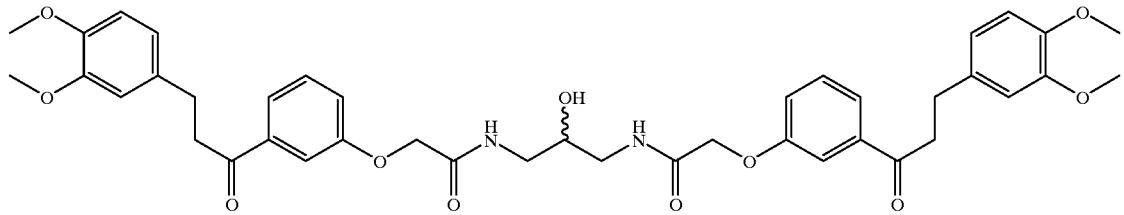

A solution of the previous acid (500 mg, 1.45 mmol) in CH$_2$Cl$_2$ (2.0 mL) at 0° C. was treated with 4-(dimethylamino)-pyridine (2 mg) followed by 1,3-dicyclohexylcarbodiimide (329 mg, 1.60 mmol). The resulting suspension was allowed to stir for 15 min then treated with a CH$_2$Cl$_2$ (2.0 mL) solution of 1,3-diamino-2-propanol (52.3 mg, 0.581 mmol). The reaction mixture was allowed to warm to room temperature and stir for 2 h after which time the reaction was diluted with EtOAc (10 mL) and filtered through a plug of Celite. The evaporated residue was chromatographed (silica gel, 100% EtOAc→5% MeOH/EtOAc) to afford product (299 mg, 69%): TLC (EtOAc) Rf=0.35; IR (neat) 3355, 2930, 1680, 1515, 1440, 1260, 1155, 1030 cm$^{-1}$; $^1$H NMR (CDCl$_3$, 300 MHz) 7.56 (d, J=7.7 Hz, 2 H), 7.47 (d, J=7.5 Hz, 2 H), 7.36 (t, J=8.0 Hz, 2 H), 7.26 (d, J=6.1 Hz, 2 H), 7.11 (d, J=8.0, 2.5 Hz, 2 H), 6.75–6.73 (m, 6H), 4.50 (s, 4 H), 3.82 (s, 6 H), 3.81 (br, 1 H), 3.80 (s, 6 H), 3.43–3.39 (m, 4 H), 3.22 (t, J=7.3 Hz, 4 H), 2.96 (t, J=7.7 Hz, 4 H); $^{13}$C NMR (CDCl$_3$, 75 MHz) 199.2, 169.8, 157.8, 149.4, 147.9, 139.0, 134.1, 130.4, 122.4, 120.6, 120.1, 114.1, 112.4, 111.9, 70.5, 67.7, 56.4, 56.3, 42.8, 41.2, 30.2; MS (ES+): (M+H)$^+$ 743; (ES−): (M−H)$^-$ 741.

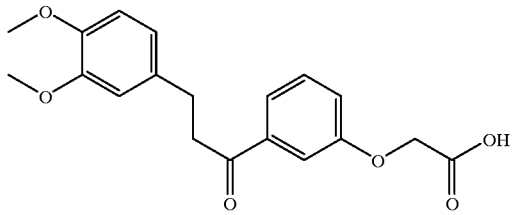

(R) 1-(3-(Carboxymethoxy)phenyl)-3-(3,4-dimethoxyphenyl)propan-1-ol

A solution of (R) 1-(3-(tert-Butoxycarbonylmethoxy)phenyl)-3-(3,4-dimethoxyphenyl)propan-1-ol (13) (5.0 g, 12.5 mmol) in CH$_2$Cl$_2$ (25 mL) was cooled to 0° C. and treated with trifluoroacetic acid (10 mL). The reaction mixture was allowed to warm to room temperature and stir for 1 h after which time the mixture was evaporated and treated twice with benzene (30 mL) and evaporated to remove traces of trifluoroacetic acid. The crude material was placed on a vacuum pump for 4 h and then triturated with diethyl ether to afford product (3.4 g, 79%) as a white solid: IR (neat) 2935, 1745, 1680, 1590, 1515, 1445, 1260, 1155, 1025 cm$^{-1}$; $^1$H NMR (CDCl$_3$, 300 MHz) 9.54 (br s, 1 H), 7.57 (d, J=7.7 Hz, 1 H), 7.48 (s, 1H), 7.36 (d, J=8.0 Hz, 1 H), 7.14–7.10 (m, 1 H), 6.77–6.74 (m, 3 H), 4.70 (s, 2 H),

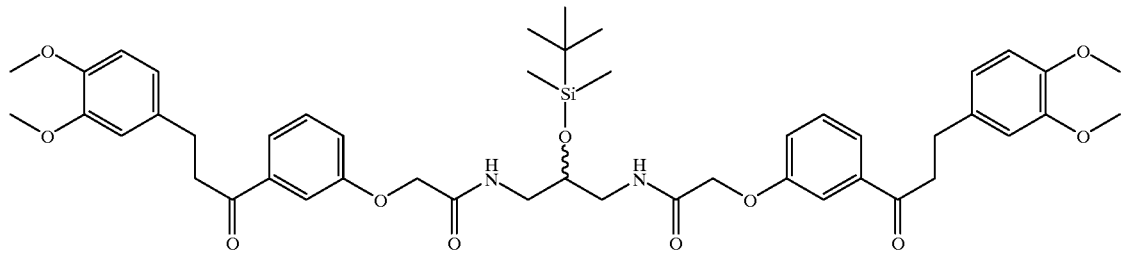

A solution of alcohol prepared above (950 mg, 1.28 mmol) in DMF (6.0 mL) was treated with imidazole (131 mg, 1.92 mmol) followed by tert-butyldimethylsilyl chloride (289 mg, 1.92 mmol) and allowed to stir for 3 h after which time an additional amount of imidazole (43 mg, 0.64 mmol) followed by tert-butyldimethylsilyl chloride (64 mg, 0.64 mmol) was added. The reaction mixture was stirred for a further 3 h and poured onto a biphasic mixture of EtOAc (25 mL) and water (50 mL). The organic layer was washed with a saturated aqueous NaCl solution (4×50 mL) then dried over NaSO₄, filtered, evaporated, and chromatographed (silica gel, 100% EtOAc→5% MeOH/EtOAc) to afford product (709 mg, 65%) as well as recovered starting material (265 mg, 31%): TLC (EtOAc/hexanes, 3:1) Rf=0.56; IR (neat) 3440, 3355, 2935, 1680, 1590, 1515, 1440, 1260, 1155, 1030 cm⁻¹; ¹H NMR (CDCl₃, 300 MHz) 7.53 (d, J=7.7 Hz, 2 H), 7.46 (s, 2 H), 7.33 (t, J=8.0 Hz, 2 H), 7.09–7.05 (m, 4 H), 6.72–6.70 (m, 6 H), 4.47 (s, 4 H), 3.87 (t, J=4.6 Hz, 6 H), 3.79 (s, 6 H), 3.77 (s, 6 H), 3.60–3.52 (m, 2 H), 3.19 (t, J=7.2 Hz, 4 H), 3.05–2.99 (m, 2 H), 2.94 (t, J=7.8 Hz, 4 H), 0.80 (s, 9 H), 0.30 (s, 6H); ¹³C NMR (CDCl₃, 75 MHz) 199.0, 168.6, 157.9, 149.4, 147.9, 139.0, 134.2, 130.4, 122.3, 120.6, 120.0, 114.1, 112.4, 111.9, 69.3, 67.7, 56.3, 41.9, 41.2, 30.2, 26.1, 18.3, −4.4; MS (ES+): (M+H)⁺ 857, (M+NH₄)⁺ 874; (ES−): (M−H)⁻ 855.

ture was allowed to stir at room temperature for 2 h followed by filtration through a pad of Celite with the aid of ethyl acetate. The cloudy filtrate was evaporated and flash chromatographed (silica gel, 75→100% EtOAc/hexanes) to afford product (487 mg, 63%) as a sticky solid: TLC (EtOAc/hexanes, 3:1) Rf=0.44; IR (neat) 3430, 2935, 1670, 1515, 1440, 1260, 1155, 1030 cm⁻¹; ¹H NMR (CDCl₃, 300 MHz) 7.21–7.16 (m, 2 H), 6.92–6.83 (m, 6 H), 6.74–6.62 (m, 8 H), 4.58 (dd, J=7.6, 5.3 Hz, 2 H), 4.40 (s, 4 H), 3.80 (br s, 1 H), 3.76 (s, 6 H), 3.75 (s, 6 H), 3.44–3.33 (m, 2 H), 3.01–2.92 (m, 2 H), 2.68–2.48 (m, 4 H), 2.03–1.85 (m, 4 H), 0.79 (s, 9 H), 0.00 (s, 6 H); ¹³C NMR (CDCl₃, 75 MHz) 169.3, 157.8, 149.3, 147.6, 134.8, 130.2, 120.6, 120.2, 114.0, 112.6, 112.5, 111.8, 106.8, 73.8, 69.2, 67.6, 56.3, 56.2, 41.9, 41.1, 32.1, 26.1, 18.3, −4.4; MS (ES+): (M+H)⁺ 861.

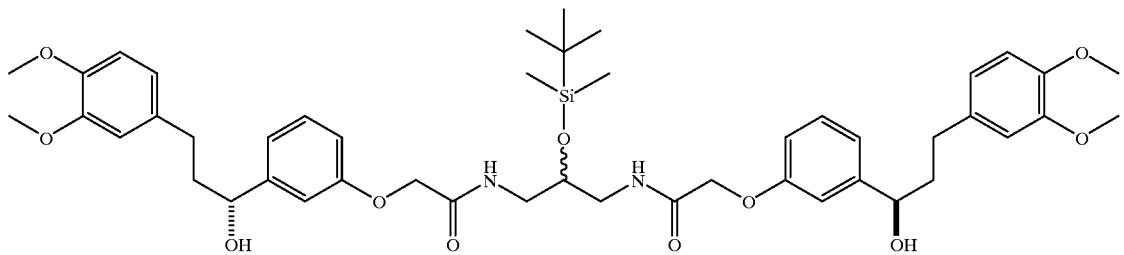

A solution of ketone (775 mg, 0.904 mmol) in THF (3 mL) at −20° C. was treated with a solution of (+)-β-chlorodiisopinocamphenylborane (1.16 g, 12.6 mmol) in THF (12 mL) at −20° C. The resulting mixture was allowed to stand in a −20° C. freezer for 64 h after which time the mixture was evaporated and treated with diethyl ether (20 mL) followed by diethanolamine (2 mL). The viscous mix-

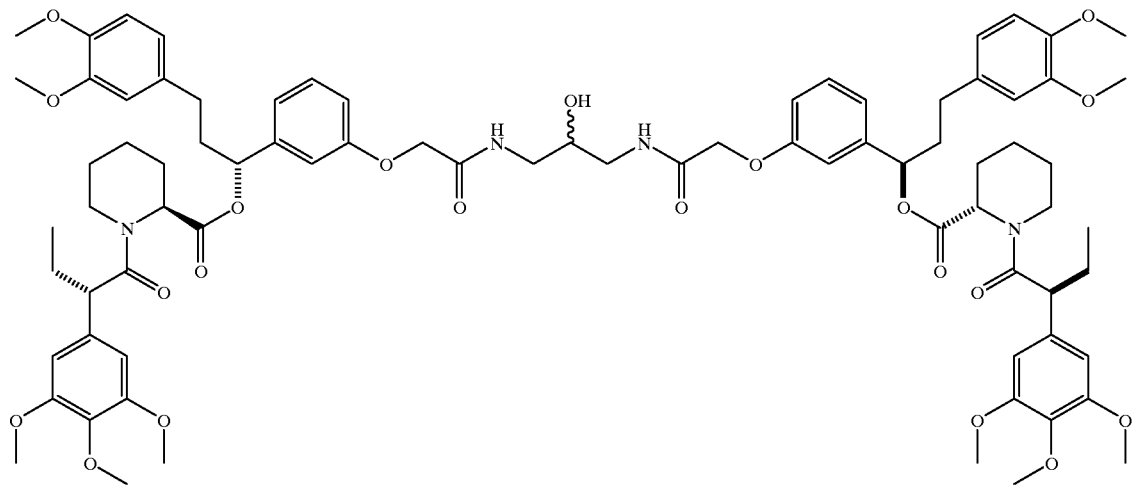

A solution of alcohol (100 mg, 0.116 mmol) in CH$_2$Cl$_2$ (3.0 mL) at 0° C. was treated with (2S)-1-((2S)-(3,4,5-trimethoxyphenyl)butyryl)-2-piperdinecarboxylic acid (136 mg, 0.371 mmol) followed by 4-(dimethylamino)-pyridine (2 mg) and 1,3-dicyclohexylcarbodiimide (77 mg, 0.371 mmol). The resulting suspension was allowed to stir for 16 h then diluted with EtOAc (5 mL) and filtered through a plug of Celite. The evaporated residue was chromatographed (silica gel, EtOAc) to afford product (68 mg, 38%) as a colorless foam: TLC (EtOAc/hexanes, 3:1) Rf=0.26, (MeOH/EtOAc, 3:97) Rf=0.39; IR (neat) 3440, 2935, 1740, 1680, 1645, 1590, 1515, 1455, 1260, 1130, 1030 cm$^{-1}$.

The ester (65 mg, 0.418 mmol) in acetonitrile (1.5 mL) at 0° C. was treated with a 5% HF/acetonitrile solution (1 mL) and allowed to warm to room temperature and stir for 30 min. The reaction mixture was poured onto a biphasic mixture of EtOAc (15 mL) and a saturated aqueous NaHCO$_3$ solution (10 mL). The organic portion was washed with an additional amount of base followed by a saturated aqeuous NaCl solution (2×10 mL). The organic solution was then dried over MgSO$_4$, filtered, evaporated, and chromatographed (silica gel, EtOAc→3% MeOH/EtOAc) to afford product (38 mg, 68%) as a colorless foam: TLC (MeOH/ethyl acetate, 3:97) Rf=0.24; IR (neat) 3360, 2940, 1740, 1645, 1590, 1515, 1455, 1240, 1130, 1030 cm$^{-1}$; MS (ES+): (M+H)$^+$ 1441, (M+NH$_4$)$^+$ 1458, (M+Na)$^+$ 1463.

Assay of binding of bumped synthetic FKBP ligands to FKBP mutants bearing compensatory mutations Affinities of bumped synthetic ligands for FKBP were determined using a competitive assay based on fluorescence polarization (FP). A fluorescein-labelled FK506 probe (4) was synthesized, and the increase in the polarization of its fluorescence used as a direct readout of % bound probe in an equilibrium binding experiment containing sub-saturating FKBP and variable amounts of bumped ligand as competitor. The assay yields IC50 values that are related to the affinity of the competitive ligand for the protein.

(i) Synthesis of fluoresceinated FK506 probe (4)

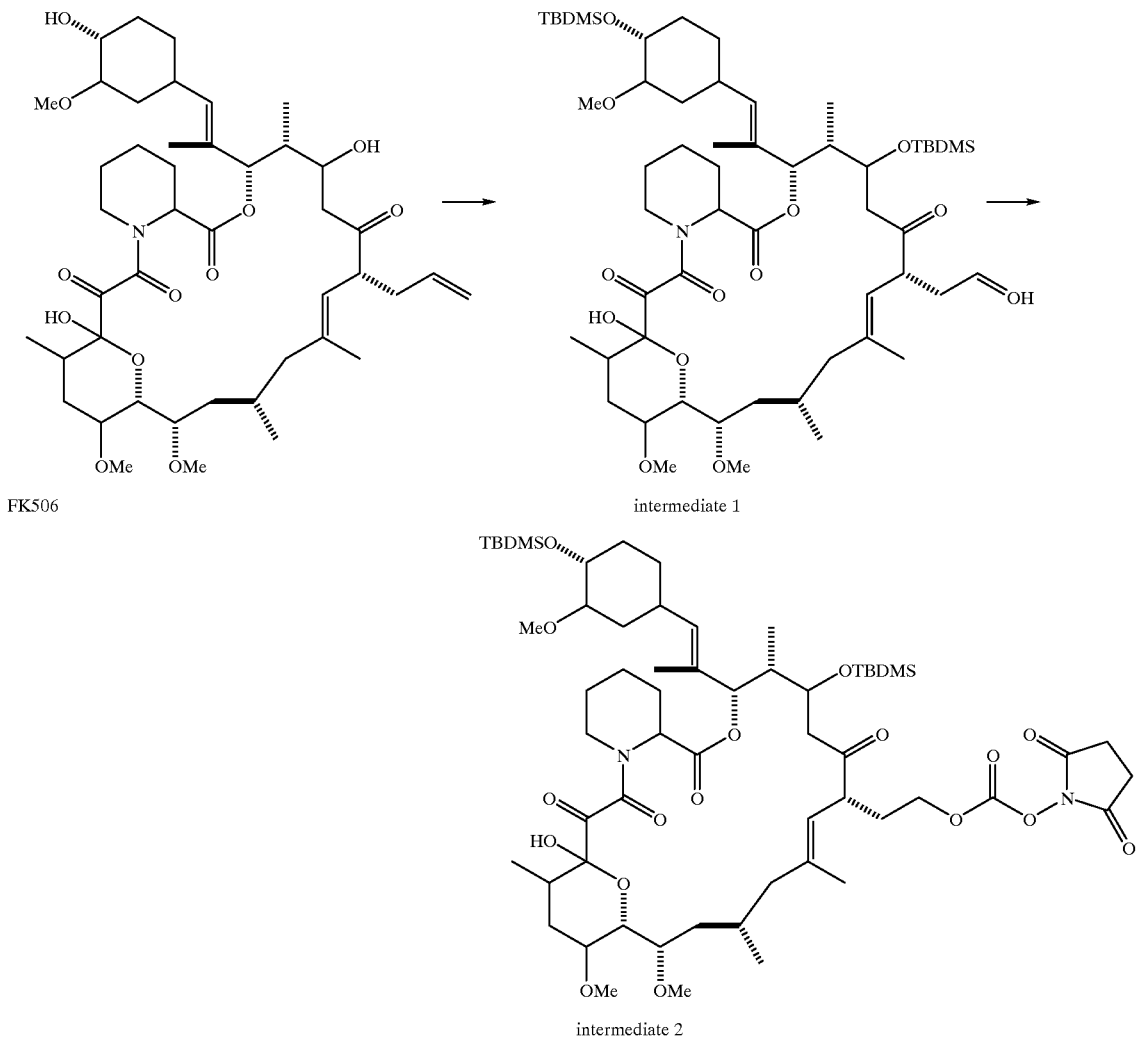

FK506 intermediate 1 intermediate 2

-continued

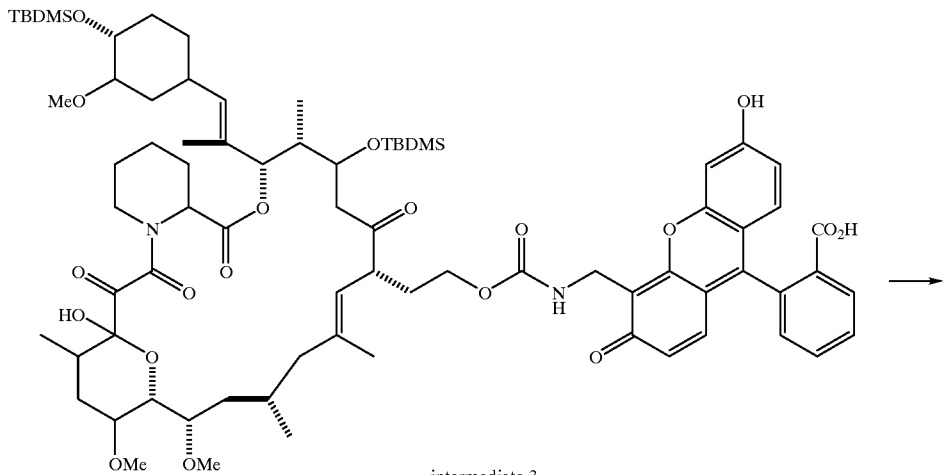

intermediate 3

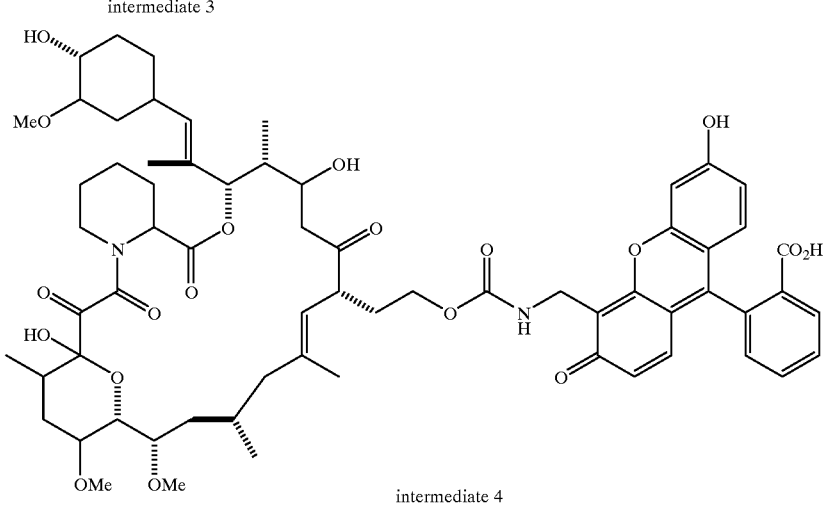

intermediate 4

24, 32-Bis(tert-Butyldimethylsilyl)ether of FK506 tert-Butyldimethylsilyl trifluoromethanesulfonate (108 µL, 470 µmol) was added dropwise to a stirred solution of FK506 (103 mg, 128 µmol) and 2,6-lutidine (89.5 µL, 768 µmol) in dichloromethane (3 mL) at 0° C. The resulting solution was stirred at 0° C. for 2 h, and then treated with MeOH (0.5 mL) and ether (15 mL). The mixture was washed with 10% aqueous NaHCO$_3$ (3 mL) and brine (3 mL). The organic layer was decanted, dried over anhydrous Na$_2$SO$_4$, filtered, and concentrated to a yellow oil. Column chromatography (silica-gel, hexanes-EtOAc 3:1) gave the title compound as a colorless oil (104 mg).

Intermediate 1

To a solution of 24,32-bis(tert-butyldimethylsilyl)ether of FK506 (100 mg, 97 µmol) in THF (2.5 mL) was added morpholine N-oxide (68 mg, 580 µmol), followed by water (60 µL), and a 4% aqueous solution of osmium tetroxide (123 µL, 20 µmol). The resulting mixture was stirred at room temperature for 4.5 h. It was then treated with 50% aqueous MeOH (1.5 mL) and sodium periodate (207 mg, 970 µmol), and the suspension stirred for an additional 1 h. The mixture was diluted with ether (10 mL) and washed with saturated aqueous NaHCO$_3$ (2×4 mL). The organic layer was decanted, dried over anhydrous sodium sulfate containing a small amount of sodium sulfite, filtered, and concentrated. The residue was dissolved in anhydrous THF (2.8 mL), cooled to −78° C. under nitrogen, and treated with a 0.5 M solution of lithium tris [(3-ethyl-3-pentyl)oxy]aluminum hydride in THF (282 µL). The resulting solution was stirred at −78° C. for 1.75 h, and then quenched by addition of ether (6 mL) and saturated ammonium chloride solution (250 µL). The mixture was allowed to warm up to room temperature and treated with anhydrous sodium sulfate. Filtration and concentration under reduced pressure afforded a pale yellow oil (97 mg), which was purified by column chromatography (silica-gel, hexanes-EtOAc 3:1) to afford 1 as a colorless oil.

Intermediate 2

A solution of the above alcohol (300 mg, 290 µmol) in acetonitrile (10 mL) was treated with 2,6-lutidine (338 µL, 2.9 mmol) and N,N'-disuccinimidylcarbonate (371 mg, 1.45 mmol). The resulting suspension was stirred at room temperature for 14.5 h, and then concentrated under reduced pressure. The residue was chromatographed (silica-gel, hexanes-EtOAc 2:1 to 100% EtOAc gradient) to afford the mixed carbonate 2 as a pale yellow oil (127 mg).

Intermediate 3

A solution of the above carbonate (30 mg, 26 µmol) and triethylamine (36 µL, 260 µmol) in acetonitrile (1 mL) was treated with 4'-(aminomethyl)fluorescein (13.5 mg, 34 µmol). The resulting bright orange suspension was stirred at room temperature for 1 h, and then concentrated under reduced pressure. The residue was chromatographed (silica-gel, hexanes-EtOAc 1:1 to 100% EtOAc to EtOAc-MeOH 1:1 gradient) to give 3 (20.5 mg) as a bright yellow solid.

Intermediate 4

A solution of bis-silyl ether 3 (35 mg, 25 μmol) in acetonitrile (2 mL) was treated with 48% (w/w) HF in water (250 μL). The resulting mixture was stirred at room temperature for 5.5 h. It was then diluted with dichloromethane (10 mL) and washed with water (2×2 mL). The organic layer was decanted, dried over anhydrous sodium sulfate, and concentrated under reduced pressure. The residue was chromatographed (silica-gel, 100% EtOAc) to afford 4 (13 mg) as a bright yellow solid.

(ii) Determination of sub-saturating concentration of FKBP mutant by direct binding Genes encoding mutant FKBPs were engineered using standard methods [F. M. Ausubel et al., Eds., Current Protocols in Molecular Biology (John Wiley & Sons, New York, 1994)]. Recombinant pure wild-type and mutant FKBPs were expressed and purified by standard methods (see eg. Wiederrecht, G. et al. 1992. *J. Biol. Chem.* 267, 21753–21760).

For competition FP assays, the appropriate protein concentration (giving ~90% binding of probe) was first determined by direct binding of probe to protein (see eg. Beacon FP System Applications Guide, Panvera Corp, Madison, Wis.). All binding assay procedures were performed at room temperature. Serial dilutions of each protein were prepared in 50 mM potassium phosphate pH 7.8/150 mM NaCl/100 μg/ml bovine gamma globulin ("FP buffer": prepared using only low-fluorescence reagents from Panvera), and 100 μl volumes transferred to wells of a Dynatech micro-fluor black 96-well fluorescence plate. 100 μl of 10 nM 4 in FP buffer plus 2% ethanol (prepared from an ethanol stock of the probe) was then added to each well with mixing. Duplicate control wells contained FP buffer instead of FKBP (for 0% probe binding) or 10 μM wild-type FKBP (for 100% binding).

The plates were stored covered in the dark for approximately 30 min to permit equilibration and then the fluorescence polarization of the sample in each well was read on a Jolley FPM-2 FP plate reader (Jolley Consulting and Research, Inc., Grayslake, Ill.) in accordance with the manufacturer's recommnendations. Polarization (mP units) for each protein concentration was plotted (y axis) vs. final concentration of FKBP (x axis). Concentrations were determined by OD280 measurements. Arbitrary units were used for non-quantitated proteins. Non-linear least square analysis was used to fit the curve and extract the $K_d$ of the protein for the probe (in cases where the protein concentration was known) using the following four-parameter equation:

$$y=M3+(((x+M1+M2)-\mathrm{SQRT}(((x+M1+M2)^{\wedge}2)-(4*x*M1)))/(2*(M1)))*(M4-M3)$$

where M1 is the probe concentration, M2 the $K_d$, and M3 and M4 the minimum and maximum mP values respectively. The M3 and M4 fitted values were used to calculate the concentration of FKBP mutant that gives 90% probe binding, and this value was then used in subsequent competition experiments.

(iii) Determination of binding affinities (IC50s) of synthetic FKBP ligands using competition FP Serial 10-fold dilutions of each synthetic ligand were prepared in 100% ethanol in glass vials and stored on ice. All other manipulations were performed at room temperature. Purified recombinant wild-type or mutant FKBP was diluted to (200/98)×the concentration predetermined to give 90% probe binding, and 98 μl aliquots transferred to wells of a Dynatech micro-fluor black 96-well fluorescence plate. 2.0 μl samples of the synthetic ligands were then transferred in duplicate to the wells with mixing. Finally, a probe solution was prepared containing 10 nM 4 in 0.1% ethanol/FP buffer, and 100 μl added to each well with mixing. Duplicate control wells contained ethanol instead of FKBP ligand (for 100% probe binding) or ethanol instead of FKBP ligand and FP buffer instead of FKBP (0% binding).

The plates were stored covered in the dark for approximately 30 min to permit equilibration and then the fluorescence polarization of the sample in each well read on a Jolley FPM-2 FP plate reader (Jolley Consulting and Research, Inc., Grayslake, Ill.) in accordance with the manufacturer's recommendations. The mean polarization (mP units) for each competitor concentration, in some cases converted to % total binding by reference to the control values, was plotted (y axis) vs. log molar final concentration of competitor (x axis). Non-linear least square analysis was used to fit the curve and extract the IC50 using the following equation:

$$y=M1+(M4-M1)/(1+\exp(M2*(M3-x)))$$

where M3 is the IC50. For incomplete curves the IC50 was determined by interpolation. FK506 was included as a control in each case.

The table below provides a sample of comparative IC50 values (nM) for a series of monomers with respect to human FKBP 12 and mutants thereof. The monomers were tested in linkered and biotinylated form. The FKBP mutants were all point mutants or double point mutants in which phenylalanine 36 (F36) and/or phenylalanine 99 is replaced with a substitute amino acid (valine, alanine, serine, methionine or glycine). These data illustrate distinct binding preferences between pairs of synthetic compounds and mutant FKBPs. A graph is also provided (FIG. 1) illustrating competition FP analysis of the binding of wild-type and mutant (F36V) FKBP to the synthetic ligand shown in column 3 of the IC50 Table, with FK506 as a control.

Cell-based transfection assay

Dimerizers may also be assayed for their ability to activate transcription of a reporter gene linked to a regulatory sequence responsive to the dimerization of FKBP-containing fusion proteins containing one or more transcription regulatory domains (e.g. DNA binding domains and transcription activation domains). We have made use of such as system as follows. Human 293 cells were transiently transfected by calcium phosphate procedure with plasmids PCGNNGF3 and PCGNNF3VP16, expressing Gal4 DNA binding domain (aa 1–147) fused to 3 copies of FKBP12 and 3 copies of FKBP12 fused to the VP16 activation domain (aa 411–490), respectively. The reporter plasmid (G5IL2-SEAP) used in these assays contains a gene that encodes for secreted alkaline phosphatase (SEAP) under the control of the minimal IL2 promoter and 5XGAL4 binding sites placed upstream of the promoter. In all cases, a plasmid expressing growth hormone was used as an internal control to moniter transfection efficiency.

Approximately, 16 hrs after transfection, the media was removed and the cells were washed twice with PBS. Cells were refed with 2.5 ml of DMEM containing 10% serum and two hours later, synthetic dimerizers were added directly to the medium at appropriate concentrations in 5 ul of ethanol carrier solution. Approximetely, 24 hrs after the addition of the drugs, 100 ul of the media was removed and assayed for SEAP activity and another 100 ul of the media was used to assay for growth hormone activity (to normalize for transfection efficiency).

Results for a sample of our multimerizers in that system are shown below (see Dimerizer Assay Worksheet) at multimerizer concentrations from 0.1 to $10^4$ nM, as indicated, normalized for hGH expression, and expressed as a % of maximal transcriptional activity observed with the prototype multimerizer, FK1012 (see Spencer et al, Science, supra).

Analogous assays have also been conducted using cell lines such as 1080 cells in place of 293 cells; activation domains such as the NF-kB p65 activation domain in place of VP16; and the composite DNA binding domain, ZFHD1 (see Pomerantz, J. L., et al. 1995. *Science*. 267:93–96.) in place of GAL4 (with the reporter gene linked to a DNA sequence recognized by ZFHD1 in place of a GAL4 site).

Table comparing binding affinities (nM) of various monomers for human FKBP12 and mutants thereof

| column–> | (1) | (2) | (3) | (4) |
|---|---|---|---|---|
| wt. FKBP | 11 | 400 | >10000 | >10000 |
| F36V | 70 | 380 | 114 | |
| F36A | 127 | | 144 | 190 |
| F36S/F99A | 15 | | 19 | 112 |
| F36M/F99G | 6 | | 11 | 30 |
| F36S/99G | 18 | | 55 | 64 |
| F36M | 52 | | 102 | 352 |
| F36V/99G | 6 | | 14 | 36 |
| F36V/99A | 13 | | 48 | 60 |

| column–> | (5) | (6) | (7) | (8) |
|---|---|---|---|---|
| wt. FKBP | >10000 | >10000 | >10000 | >10000 |
| F36V | | | | |
| F36A | 295 | 210 | | 210 |
| F36S/F99A | | | | 31 |
| F36M/F99G | 100 | 100 | 300 | |
| F36S/99G | 63 | 71 | 854 | 20 |
| F36M | 460 | 208 | >6000 | 122 |
| F36V/99G | 31 | 31 | 540 | |
| F36V/99A | 60 | 60 | 800 | 25 |

-continued

Table comparing binding affinities (nM) of various monomers for human FKBP12 and mutants thereof

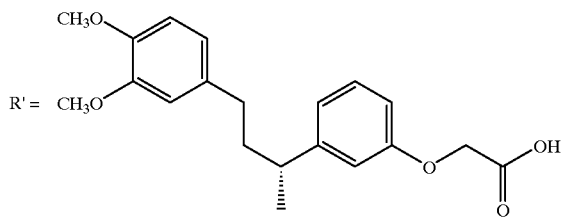

It should be appreciated that multimerizers of this invention will vary somewhat in their observed activity, depending on the particular chimeric proteins and other components of such systems. We recommend that the practitioner select multimerizers based on their performance in the particular system of interest.

What is claimed is:

1. A compound of a formula selected from the group consisting of:

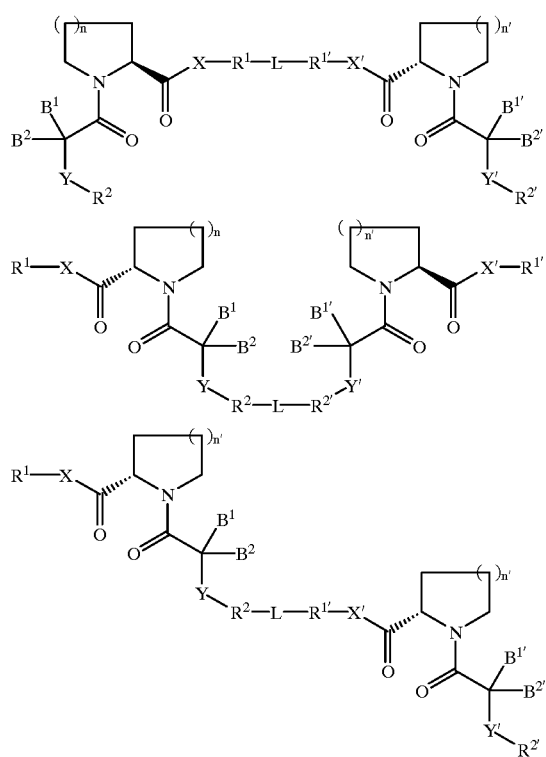

wherein:
n and n' are each independently 1 or 2;
$B^1$, $B^2$, $B^{1'}$ and $B^{2'}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl, or heteroaryl moeities;
Y and Y' are each independently O, S, NH, —NH(C=O)—, NH(C=O)—O—, NH(SO$_2$)—, NR$^3$, or a covalent bond;
X and X' are each independently O, S, or CH$_2$;
$R^1$, $R^2$, $R^{1'}$, $R^{2'}$ and $R^3$ are the same or different and are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl, or heteroaryl moeities; and
L is a covalent linker moiety.

2. A compound of claim 1, wherein the compound is represented by the formula below:

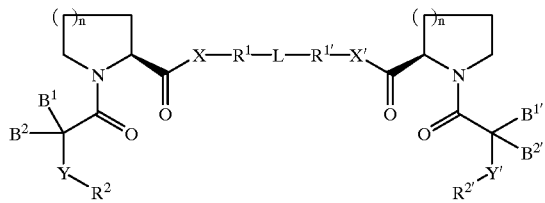

3. A compound represented by the formula:

M—L—Q wherein
M comprises a moeity of the formula below

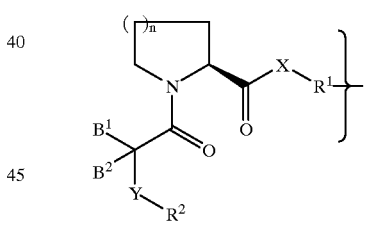

Q is another moiety of formula M above or a moeity of the formula:

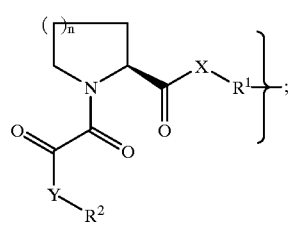

n is 1 or 2;
$B^1$ and $B^2$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl, or heteroaryl moeities;

Y is O, S, NH, —NH(C=O)—, NH(C=O)—O—, NH(SO$_2$)—, NR$^3$, or a covalent bond;

X is O, S, or CH$_2$;

R$^1$, R$^2$ and R$^3$ are the same or different and are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl, or heteroaryl moeities; and L is a covalent linker moiety.

4. A compound of claims 1, 2 or 3 which selectively binds to an FKBP mutant over the wild type human FKBP 12.

5. A compound of claim 3, which binds to a FKBP mutant at a rate at least ten times greater than the rate of binding to wild type human FKBP 12.

6. A compound of claim 5, wherein said rate of binding to a FKBP mutant is at least a hundred times greater than the rate of binding to wild type human FKBP12.

7. A compound of claims 1, 2, or 3 which has a binding affinity (IC50) to wild type human FKBP greater than 10,000 nM.

8. A compound of claim 7, wherein said binding affinity is greater than 100,000 nM.

* * * * *